United States Patent
Bossmann et al.

(10) Patent No.: US 9,216,154 B2
(45) Date of Patent: Dec. 22, 2015

(54) PROTEASE SELECTIVE SUPRAMOLECULAR ASSEMBLIES

(71) Applicant: Kansas State University Research Foundation, Manhattan, KS (US)

(72) Inventors: Stefan H. Bossmann, Manhattan, KS (US); Deryl L. Troyer, Manhattan, KS (US); Matthew T. Basel, Manhattan, KS (US); Tej B. Shrestha, Manhattan, KS (US); Hongwang Wang, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 43 days.

(21) Appl. No.: 13/800,456

(22) Filed: Mar. 13, 2013

(65) Prior Publication Data
US 2013/0183702 A1    Jul. 18, 2013

Related U.S. Application Data

(63) Continuation-in-part of application No. PCT/US2011/053711, filed on Sep. 28, 2011.

(60) Provisional application No. 61/387,870, filed on Sep. 29, 2010.

(51) Int. Cl.
*C12Q 1/37* (2006.01)
*C12N 11/06* (2006.01)
(Continued)

(52) U.S. Cl.
CPC ........... *A61K 9/127* (2013.01); *A61K 47/48238* (2013.01); *A61K 47/48815* (2013.01)

(58) Field of Classification Search
CPC ............ A61K 9/127; A61K 47/48238; A61K 47/48815
USPC ............................................ 435/23, 181, 183
See application file for complete search history.

(56) References Cited

U.S. PATENT DOCUMENTS 4,708,861 A * 11/1987 Popescu et al. ............... 424/1.21
6,592,847 B1    7/2003 Weissleder et al.
(Continued)

FOREIGN PATENT DOCUMENTS

WO    0200265    1/2002
WO    0241760    5/2002
(Continued)

OTHER PUBLICATIONS

Lee et al., Polymer-caged liposomes: a pH-responsive delivery system with high stability. Journal of American Chemical Society, vol. 129 (2007) pp. 15096-15097.*

(Continued)

*Primary Examiner* — Laura Schuberg
*Assistant Examiner* — Kara Johnson
(74) *Attorney, Agent, or Firm* — Crissa A. Cook

(57) ABSTRACT

Supramolecular assemblies for delivering active agents to cancerous or precancerous tissues in a subject are provided. These supramolecular assemblies are also useful in assays for detecting and imaging of cancerous and precancerous cells. The assemblies are protease-sensitive and comprise a peptide linkage containing a protease consensus sequence. The assemblies can be selectively targeted to cancerous tissue where the protease enzymes degrade the peptide linkage thereby releasing the active agents which were physically or mechanically contained in or retained by the supramolecular assembly.

24 Claims, 26 Drawing Sheets

(51) Int. Cl.
*C12N 9/00* (2006.01)
*A61K 9/127* (2006.01)
*A61K 47/48* (2006.01)

(56) References Cited

U.S. PATENT DOCUMENTS

| | | |
|---|---|---|
| 2002/0035082 A1 | 3/2002 | Grinstaff et al. |
| 2004/0180094 A1 | 9/2004 | Joyce |
| 2005/0123563 A1 | 6/2005 | Doranz et al. |
| 2005/0239170 A1 | 10/2005 | Hedley et al. |

FOREIGN PATENT DOCUMENTS

| | | |
|---|---|---|
| WO | 2007109364 | 9/2007 |
| WO | 2009111470 | 9/2009 |

OTHER PUBLICATIONS

Allen and Cleland, Serum-induced leakage of liposome contents. Biochimica et Biophysica Acta, vol. 597 (1980) pp. 418-426.*

DiTizio et al., Localized drug delivery using cross-linked gelatin gels containing liposomes: factors influencing liposome stability and drug release. Journal of Biomedical Materials Research, vol. 51, No. 1 (May 11, 2000) pp. 96-106.*

Xu et al., Contributions of the MMP-2 collagen binding domain to gelatin cleavage: substrate binding via the collagen binding domain is required for hydrolysis of gelatin but not short peptides. Matrix Biology, vol. 23, No. 3 (Jun. 2004) pp. 171-181.*

Matthew T. Basel et al., "Protease-Sensitive, Polymer-Caged Liposomes: A Method for Making Highly Targeted Liposomes Using Triggered Release." ACS NANO, vol. 5, No. 3, Feb. 11, 2011.

Sarkar, Nihar et al. "Matrix Metalloproteinase-Assisted Triggered Release of Liposomal Contents" Biocanjugate Chem., 19 (1), 57-64, Dec. 14, 2007.

Elegbede, Adekunle et al. "Mechanistic Studies of the Triggered Release of Liposomal Contents by Matrix Metalloproteinase-9," J. Am. Chem. Soc., 120 (32) 10633-10642, Jul. 22, 2008.

Wang, Xiao-Yang "Matrilysin-1 Mediates Bronchiolization of Alveoli, a Potential Premalignant Change in Lung Cancer," The American Journal of Pathology, vol. 175, No. 2, Aug. 2009.

Strandvik, G. F. "Hypertonic Saline in Critical Care: A Review of the Literature and Guidelines for Use in Hypotensive States and Raised Intracranial Pressure," Journal of the Association of Anaesthetists of Great Britain and Ireland, 64, 990-1003, 2009.

The International Search Report and Written Opinion dated April 24, 2012 in the correspondent PCT/US2011/053711 filed Sep. 28, 2011.

* cited by examiner

Fluorescence versus Concentration

SEQUENCE LISTING

<160> NUMBER OF SEQ ID NOS: 82

<210> SEQ ID NO 1
<211> LENGTH: 5
<212> TYPE: PRT
<213> ORGANISM: Homo sapiens

<400> SEQUENCE: 1

Ser Gly Arg Ser Ala
1               5

<210> SEQ ID NO 2
<211> LENGTH: 8
<212> TYPE: PRT
<213> ORGANISM: Homo sapiens

<400> SEQUENCE: 2

Val Pro Met Ser Met Arg Gly Gly
1               5

<210> SEQ ID NO 3
<211> LENGTH: 8
<212> TYPE: PRT
<213> ORGANISM: Homo sapiens

<400> SEQUENCE: 3

Ile Pro Val Ser Leu Arg Ser Gly
1               5

<210> SEQ ID NO 4
<211> LENGTH: 8
<212> TYPE: PRT
<213> ORGANISM: Homo sapiens

<400> SEQUENCE: 4

Arg Pro Phe Ser Met Ile Met Gly
1               5

<210> SEQ ID NO 5
<211> LENGTH: 8
<212> TYPE: PRT
<213> ORGANISM: Homo sapiens

<400> SEQUENCE: 5

Val Pro Leu Ser Leu Thr Met Gly
1               5

<210> SEQ ID NO 6
<211> LENGTH: 8
<212> TYPE: PRT
<213> ORGANISM: Homo sapiens

<400> SEQUENCE: 6

Val Pro Leu Ser Leu Tyr Ser Gly
1               5

<210> SEQ ID NO 7
<211> LENGTH: 31
<212> TYPE: PRT
<213> ORGANISM: Homo sapiens

<400> SEQUENCE: 7

His Gly Pro Glu Gly Leu Arg Val Gly Phe Tyr Glu Ser Asp Val Met
1               5                   10                  15

```
Gly Arg Gly His Ala Arg Leu Val His Val Glu Glu Pro His Thr
            20                  25                  30
```

<210> SEQ ID NO 8
<211> LENGTH: 8
<212> TYPE: PRT
<213> ORGANISM: Homo sapiens

<400> SEQUENCE: 8

```
Gly Ala Ala Asn Leu Val Arg Gly
1               5
```

<210> SEQ ID NO 9
<211> LENGTH: 12
<212> TYPE: PRT
<213> ORGANISM: Homo sapiens

<400> SEQUENCE: 9

```
Gly Pro Gln Gly Leu Ala Gly Gln Arg Gly Ile Val
1               5                   10
```

<210> SEQ ID NO 10
<211> LENGTH: 8
<212> TYPE: PRT
<213> ORGANISM: Homo sapiens

<400> SEQUENCE: 10

```
Ile Pro Glu Ser Leu Arg Ala Gly
1               5
```

<210> SEQ ID NO 11
<211> LENGTH: 12
<212> TYPE: PRT
<213> ORGANISM: Homo sapiens

<400> SEQUENCE: 11

```
Ser Leu Leu Lys Ser Arg Met Val Pro Asn Phe Asn
1               5                   10
```

<210> SEQ ID NO 12
<211> LENGTH: 4
<212> TYPE: PRT
<213> ORGANISM: Homo sapiens

<400> SEQUENCE: 12

```
Asp Ala Phe Lys
1
```

<210> SEQ ID NO 13
<211> LENGTH: 12
<212> TYPE: PRT
<213> ORGANISM: Homo sapiens

<400> SEQUENCE: 13

```
Ser Leu Leu Ile Phe Arg Ser Trp Ala Asn Phe Asn
1               5                   10
```

<210> SEQ ID NO 14
<211> LENGTH: 10
<212> TYPE: PRT
<213> ORGANISM: Homo sapiens

<400> SEQUENCE: 14

```
Ser Gly Lys Pro Ile Leu Phe Phe Arg Leu
1               5                   10
```

<210> SEQ ID NO 15
<211> LENGTH: 11
<212> TYPE: PRT
<213> ORGANISM: Homo sapiens

<400> SEQUENCE: 15

Ser Gly Ser Pro Ala Phe Leu Ala Lys Asn Arg
1               5                   10

<210> SEQ ID NO 16
<211> LENGTH: 10
<212> TYPE: PRT
<213> ORGANISM: Homo sapiens

<400> SEQUENCE: 16

Ser Gly Lys Pro Ile Ile Phe Phe Arg Leu
1               5                   10

<210> SEQ ID NO 17
<211> LENGTH: 5
<212> TYPE: PRT
<213> ORGANISM: Homo sapiens

<400> SEQUENCE: 17

Pro Arg Ala Gly Ala
1               5

<210> SEQ ID NO 18
<211> LENGTH: 12
<212> TYPE: PRT
<213> ORGANISM: Homo sapiens

<400> SEQUENCE: 18

Ser Gly Val Val Ile Ala Thr Val Ile Val Ile Thr
1               5                   10

<210> SEQ ID NO 19
<211> LENGTH: 8
<212> TYPE: PRT
<213> ORGANISM: Homo sapiens

<400> SEQUENCE: 19

Gly Pro Leu Gly Met Leu Ser Gln
1               5

<210> SEQ ID NO 20
<211> LENGTH: 8
<212> TYPE: PRT
<213> ORGANISM: Artificial Sequence
<220> FEATURE:
<223> OTHER INFORMATION: Peptide linkage with protease consensus
      sequence.

<400> SEQUENCE: 20

Gly Ser Gly Arg Ser Ala Gly Cys
1               5

<210> SEQ ID NO 21
<211> LENGTH: 8
<212> TYPE: PRT
<213> ORGANISM: Artificial Sequence
<220> FEATURE:
<223> OTHER INFORMATION: Peptide linkage with protease consensus
      sequence.

```
<400> SEQUENCE: 21

Gly Ser Gly Arg Ser Ala Gly Lys
1               5

<210> SEQ ID NO 22
<211> LENGTH: 13
<212> TYPE: PRT
<213> ORGANISM: Artificial Sequence
<220> FEATURE:
<223> OTHER INFORMATION: Peptide linkage with protease consensus
      sequence.

<400> SEQUENCE: 22

Lys Gly Gly Gly Ser Gly Arg Ser Ala Gly Gly Gly Cys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Peptide linkage with protease consensus
      sequence.

<400> SEQUENCE: 23

Cys Gly Gly Gly Ser Gly Arg Ser Ala Gly Gly Cys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Peptide linkage with protease consensus
      sequence.

<400> SEQUENCE: 24

Cys Gly Gly Gly Ser Gly Arg Ser Ala Gly Gly Gly Cys
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Peptide linkage with protease consensus
      sequence.

<400> SEQUENCE: 25

Asp Gly Gly Ser Gly Arg Ser Ala Gly Gly Lys
1               5                   10

<210> SEQ ID NO 26
<211> LENGTH: 19
<212> TYPE: PRT
<213> ORGANISM: Artificial Sequence
<220> FEATURE:
<223> OTHER INFORMATION: Peptide linkage with protease consensus
      sequence.

<400> SEQUENCE: 26

Ser Arg Ser Arg Ser Arg Ser Arg Ser Arg Gly Arg Ser Ala Gly
1               5                   10                  15

Gly Gly Cys

<210> SEQ ID NO 27
```

```
<211> LENGTH: 11
<212> TYPE: PRT
<213> ORGANISM: Artificial Sequence
<220> FEATURE:
<223> OTHER INFORMATION: Peptide linkage with protease consensus
      sequence.

<400> SEQUENCE: 27

Lys Gly Gly Ser Gly Arg Ser Ala Gly Gly Asp
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Peptide linkage with protease consensus
      sequence.

<400> SEQUENCE: 28

Cys Gly Gly Gly Ser Gly Arg Ser Ala Gly Gly Gly
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Peptide linkage with protease consensus
      sequence.

<400> SEQUENCE: 29

Asp Gly Gly Gly Ser Gly Arg Ser Ala Gly Gly Gly Asp
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Peptide linkage with protease consensus
      sequence.

<400> SEQUENCE: 30

Asp Gly Ala Gly Ser Gly Arg Ser Ala Gly Ala Gly Asp
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Peptide linkage with protease consensus
      sequence.

<400> SEQUENCE: 31

Lys Gly Gly Ser Gly Arg Ser Ala Gly Gly Gly
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Peptide linkage with protease consensus
      sequence.

<400> SEQUENCE: 32
```

Asp Gly Gly Ser Gly Arg Ser Ala Gly Gly Gly Cys
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Peptide linkage with protease consensus
      sequence.

<400> SEQUENCE: 33

His His His Gly Ala Gly Ser Gly Arg Ser Ala Gly Ala Gly
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Peptide linkage with protease consensus
      sequence.

<400> SEQUENCE: 34

Lys Gly Gly Val Pro Met Ser Met Arg Gly Gly Gly Cys
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Peptide linkage with protease consensus
      sequence.

<400> SEQUENCE: 35

His His His Gly Ala Gly Val Pro Met Ser Met Arg Gly Ala Gly
1               5                   10                  15

<210> SEQ ID NO 36
<211> LENGTH: 13
<212> TYPE: PRT
<213> ORGANISM: Artificial Sequence
<220> FEATURE:
<223> OTHER INFORMATION: Peptide linkage with protease consensus
      sequence.

<400> SEQUENCE: 36

Lys Gly Gly Ile Pro Val Ser Leu Arg Ser Gly Gly Cys
1               5                   10

<210> SEQ ID NO 37
<211> LENGTH: 16
<212> TYPE: PRT
<213> ORGANISM: Artificial Sequence
<220> FEATURE:
<223> OTHER INFORMATION: Peptide linkage with protease consensus
      sequence.

<400> SEQUENCE: 37

His His His Gly Ala Gly Ile Pro Val Ser Leu Arg Ser Gly Ala Gly
1               5                   10                  15

<210> SEQ ID NO 38
<211> LENGTH: 16
<212> TYPE: PRT
<213> ORGANISM: Artificial Sequence
<220> FEATURE:

<223> OTHER INFORMATION: Peptide linkage with protease consensus
      sequence.

<400> SEQUENCE: 38

His His His Gly Ala Gly Arg Pro Phe Ser Met Ile Met Gly Ala Gly
1               5                   10                  15

<210> SEQ ID NO 39
<211> LENGTH: 13
<212> TYPE: PRT
<213> ORGANISM: Artificial Sequence
<220> FEATURE:
<223> OTHER INFORMATION: Peptide linkage with protease consensus
      sequence.

<400> SEQUENCE: 39

Lys Gly Gly Val Pro Leu Ser Leu Thr Met Gly Gly Cys
1               5                   10

<210> SEQ ID NO 40
<211> LENGTH: 16
<212> TYPE: PRT
<213> ORGANISM: Artificial Sequence
<220> FEATURE:
<223> OTHER INFORMATION: Peptide linkage with protease consensus
      sequence.

<400> SEQUENCE: 40

His His His Gly Ala Gly Val Pro Leu Ser Leu Thr Met Gly Ala Gly
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Peptide linkage with protease consensus
      sequence.

<400> SEQUENCE: 41

His His His Gly Ala Gly Val Pro Leu Ser Leu Tyr Ser Gly Ala Gly
1               5                   10                  15

<210> SEQ ID NO 42
<211> LENGTH: 17
<212> TYPE: PRT
<213> ORGANISM: Artificial Sequence
<220> FEATURE:
<223> OTHER INFORMATION: Peptide linkage with protease consensus
      sequence.

<400> SEQUENCE: 42

His His His Gly Ala Gly Gly Ala Ala Asn Leu Val Arg Gly Gly Ala
1               5                   10                  15

Gly

<210> SEQ ID NO 43
<211> LENGTH: 20
<212> TYPE: PRT
<213> ORGANISM: Artificial Sequence
<220> FEATURE:
<223> OTHER INFORMATION: Peptide linkage with protease consensus
      sequence.

<400> SEQUENCE: 43

His His His Gly Ala Gly Pro Gln Gly Leu Ala Gly Gln Arg Gly Ile
1               5                   10                  15

Val Gly Ala Gly
            20

<210> SEQ ID NO 44
<211> LENGTH: 21
<212> TYPE: PRT
<213> ORGANISM: Artificial Sequence
<220> FEATURE:
<223> OTHER INFORMATION: Peptide linkage with protease consensus
      sequence.

<400> SEQUENCE: 44

His His His Gly Ala Gly Ser Leu Leu Lys Ser Arg Met Val Pro Asn
1               5                   10                  15

Phe Asn Gly Ala Gly
            20

<210> SEQ ID NO 45
<211> LENGTH: 21
<212> TYPE: PRT
<213> ORGANISM: Artificial Sequence
<220> FEATURE:
<223> OTHER INFORMATION: Peptide linkage with protease consensus
      sequence.

<400> SEQUENCE: 45

His His His Gly Ala Gly Ser Leu Leu Ile Phe Arg Ser Trp Ala Asn
1               5                   10                  15

Phe Asn Gly Ala Gly
            20

<210> SEQ ID NO 46
<211> LENGTH: 21
<212> TYPE: PRT
<213> ORGANISM: Artificial Sequence
<220> FEATURE:
<223> OTHER INFORMATION: Peptide linkage with protease consensus
      sequence.

<400> SEQUENCE: 46

His His His Gly Ala Gly Ser Gly Val Val Ile Ala Thr Val Ile Val
1               5                   10                  15

Ile Thr Gly Ala Gly
            20

<210> SEQ ID NO 47
<211> LENGTH: 12
<212> TYPE: PRT
<213> ORGANISM: Artificial Sequence
<220> FEATURE:
<223> OTHER INFORMATION: Peptide linkage with protease consensus
      sequence.

<400> SEQUENCE: 47

His His His Gly Ala Gly Pro Arg Ala Gly Ala Gly
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Synthetic tumor-homing peptide

<400> SEQUENCE: 48

Cys Arg Gly Asp Lys Gly Pro Asp Cys
1               5

<210> SEQ ID NO 49
<211> LENGTH: 31
<212> TYPE: PRT
<213> ORGANISM: Artificial Sequence
<220> FEATURE:
<223> OTHER INFORMATION: Synthetic tumor-homing peptide

<400> SEQUENCE: 49

Lys Asp Glu Pro Gln Arg Arg Ser Ala Arg Leu Ser Ala Lys Pro Ala
1               5                   10                  15

Pro Pro Lys Pro Glu Pro Lys Pro Lys Lys Ala Pro Ala Lys Lys
            20                  25                  30

<210> SEQ ID NO 50
<211> LENGTH: 9
<212> TYPE: PRT
<213> ORGANISM: Artificial Sequence
<220> FEATURE:
<223> OTHER INFORMATION: Synthetic tumor-homing peptide

<400> SEQUENCE: 50

Cys Gly Asn Lys Arg Thr Arg Gly Cys
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic tumor-homing peptide

<400> SEQUENCE: 51

His Ala Ile Tyr Pro Arg His
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic tumor-homing peptide

<400> SEQUENCE: 52

Ala Thr Trp Leu Pro Pro Arg
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic tumor-homing peptide

<400> SEQUENCE: 53

Arg Arg Lys Arg Arg Arg
1               5

<210> SEQ ID NO 54
<211> LENGTH: 13
<212> TYPE: PRT
<213> ORGANISM: Artificial Sequence
<220> FEATURE:
<223> OTHER INFORMATION: Synthetic tumor-homing peptide

```
<400> SEQUENCE: 54

Glu Glu Glu Ala Ala Gly Arg Lys Arg Lys Lys Arg Thr
1               5                   10

<210> SEQ ID NO 55
<211> LENGTH: 36
<212> TYPE: PRT
<213> ORGANISM: Artificial Sequence
<220> FEATURE:
<223> OTHER INFORMATION: Synthetic tumor-homing peptide
<220> FEATURE:
<221> NAME/KEY: MISC_FEATURE
<222> LOCATION: (11)..(11)
<223> OTHER INFORMATION: Xaa is 3,5 diiodotyrosine

<400> SEQUENCE: 55

Ala Glu Gln Asn Pro Ile Tyr Trp Ala Arg Xaa Ala Asp Trp Leu Phe
1               5                   10                  15

Thr Thr Pro Leu Leu Leu Asp Leu Ala Ala Leu Leu Val Asp Ala
            20                  25                  30

Asp Glu Gly Thr
        35

<210> SEQ ID NO 56
<211> LENGTH: 29
<212> TYPE: PRT
<213> ORGANISM: Artificial Sequence
<220> FEATURE:
<223> OTHER INFORMATION: Synthetic tumor-homing peptide
<220> FEATURE:
<221> NAME/KEY: MISC_FEATURE
<222> LOCATION: (15)..(15)
<223> OTHER INFORMATION: Xaa is 3,5 diiodotyrosine

<400> SEQUENCE: 56

Trp Glu Ala Ala Leu Ala Glu Ala Leu Ala Glu Ala Leu Ala Xaa His
1               5                   10                  15

Leu Ala Ala Leu Ala Glu Ala Leu Glu Ala Leu Ala Ala
            20                  25

<210> SEQ ID NO 57
<211> LENGTH: 7
<212> TYPE: PRT
<213> ORGANISM: Artificial Sequence
<220> FEATURE:
<223> OTHER INFORMATION: Synthetic tumor-homing peptide

<400> SEQUENCE: 57

Ala Pro Ser Pro Met Ile Trp
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic tumor-homing peptide

<400> SEQUENCE: 58

Leu Gln Asn Ala Pro Arg Ser
1               5

<210> SEQ ID NO 59
<211> LENGTH: 10
<212> TYPE: PRT
<213> ORGANISM: Artificial Sequence
```

```
<220> FEATURE:
<223> OTHER INFORMATION: Synthetic tumor-homing peptide

<400> SEQUENCE: 59

Cys Gly Leu Ile Ile Gln Lys Asn Glu Cys
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic tumor-homing peptide

<400> SEQUENCE: 60

Cys Asn Ala Gly Glu Ser Ser Lys Asn Cys
1               5                   10

<210> SEQ ID NO 61
<211> LENGTH: 5
<212> TYPE: PRT
<213> ORGANISM: Artificial Sequence
<220> FEATURE:
<223> OTHER INFORMATION: Synthetic tumor-homing peptide

<400> SEQUENCE: 61

Cys Arg Glu Lys Ala
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic tumor-homing peptide

<400> SEQUENCE: 62

Cys Gly Lys Arg Lys
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic tumor-homing peptide

<400> SEQUENCE: 63

Cys Gly Ser Leu Val Arg Cys
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic tumor-homing peptide

<400> SEQUENCE: 64

Cys Pro Gly Pro Glu Gly Ala Gly Cys
1               5

<210> SEQ ID NO 65
<211> LENGTH: 5
<212> TYPE: PRT
<213> ORGANISM: Artificial Sequence
<220> FEATURE:
```

```
<223> OTHER INFORMATION: Synthetic tumor-homing peptide

<400> SEQUENCE: 65

Cys Asp Thr Arg Leu
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic tumor-homing peptide

<400> SEQUENCE: 66

Arg Arg Pro Tyr Ile Leu
1               5

<210> SEQ ID NO 67
<211> LENGTH: 12
<212> TYPE: PRT
<213> ORGANISM: Artificial Sequence
<220> FEATURE:
<223> OTHER INFORMATION: Synthetic tumor-homing peptide

<400> SEQUENCE: 67

Glu Asp Tyr Glu Leu Met Asp Leu Leu Ala Tyr Leu
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Synthetic tumor-homing peptide

<400> SEQUENCE: 68

Ala Thr Trp Leu Pro Pro Arg
1               5

<210> SEQ ID NO 69
<211> LENGTH: 13
<212> TYPE: PRT
<213> ORGANISM: Artificial Sequence
<220> FEATURE:
<223> OTHER INFORMATION: Synthetic tumor-homing peptide

<400> SEQUENCE: 69

Cys Gly Gly Lys Leu Lys Ser Gln Leu Val Lys Arg Lys
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic tumor-homing peptide

<400> SEQUENCE: 70

Cys Gly Gly Lys Asn Gly Arg Tyr Ser Ile Ser Arg
1               5                   10

<210> SEQ ID NO 71
<211> LENGTH: 16
<212> TYPE: PRT
<213> ORGANISM: Artificial Sequence
<220> FEATURE:
<223> OTHER INFORMATION: Synthetic tumor-homing peptide
```

<400> SEQUENCE: 71

Cys Gly Gly Arg Asp Gly Thr Arg Tyr Val Gln Lys Gly Glu Tyr Arg
1               5                   10                  15

<210> SEQ ID NO 72
<211> LENGTH: 14
<212> TYPE: PRT
<213> ORGANISM: Artificial Sequence
<220> FEATURE:
<223> OTHER INFORMATION: Synthetic tumor-homing peptide

<400> SEQUENCE: 72

Cys Gly Gly Ala His Trp Gln Phe Asn Ala Leu Thr Val Arg
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Synthetic tumor-homing peptide

<400> SEQUENCE: 73

Gly Arg Lys Lys Arg Arg Gln Arg Arg Arg Pro Gln Cys
1               5                   10

<210> SEQ ID NO 74
<211> LENGTH: 5
<212> TYPE: PRT
<213> ORGANISM: Homo sapiens

<400> SEQUENCE: 74

Asp Glu Val Asp Gly
1               5

<210> SEQ ID NO 75
<211> LENGTH: 4
<212> TYPE: PRT
<213> ORGANISM: Homo sapiens

<400> SEQUENCE: 75

Val Glu Ile Asp
1

<210> SEQ ID NO 76
<211> LENGTH: 7
<212> TYPE: PRT
<213> ORGANISM: Artificial Sequence
<220> FEATURE:
<223> OTHER INFORMATION: Peptide linkage with consensus sequence and
      crosslinkable unit
<220> FEATURE:
<221> NAME/KEY: REPEAT
<222> LOCATION: (7)..(7)
<223> OTHER INFORMATION: 3 to 30 lysine residues

<400> SEQUENCE: 76

Cys Asp Glu Val Asp Gly Lys
1               5

<210> SEQ ID NO 77
<211> LENGTH: 7
<212> TYPE: PRT
<213> ORGANISM: Artificial Sequence
<220> FEATURE:
<223> OTHER INFORMATION: Peptide linkage with consensus sequence and

```
        crosslinkable unit
<220> FEATURE:
<221> NAME/KEY: REPEAT
<222> LOCATION: (7)..(7)
<223> OTHER INFORMATION: 3 to 30  aspartic acid residues

<400> SEQUENCE: 77

Cys Asp Glu Val Asp Gly Asp
1               5

<210> SEQ ID NO 78
<211> LENGTH: 7
<212> TYPE: PRT
<213> ORGANISM: Artificial Sequence
<220> FEATURE:
<223> OTHER INFORMATION: Peptide linkage with consensus sequence and
      crosslinkable unit
<220> FEATURE:
<221> NAME/KEY: REPEAT
<222> LOCATION: (7)..(7)
<223> OTHER INFORMATION: 3 to 30 glutamic acid residues

<400> SEQUENCE: 78

Cys Asp Glu Val Asp Gly Glu
1               5

<210> SEQ ID NO 79
<211> LENGTH: 6
<212> TYPE: PRT
<213> ORGANISM: Artificial Sequence
<220> FEATURE:
<223> OTHER INFORMATION: Peptide linkage with consensus sequence and
      crosslinkable unit
<220> FEATURE:
<221> NAME/KEY: REPEAT
<222> LOCATION: (6)..(6)
<223> OTHER INFORMATION: 3 to 30 lysine residues

<400> SEQUENCE: 79

Cys Val Glu Ile Asp Lys
1               5

<210> SEQ ID NO 80
<211> LENGTH: 6
<212> TYPE: PRT
<213> ORGANISM: Artificial Sequence
<220> FEATURE:
<223> OTHER INFORMATION: Peptide linkage with consensus sequence and
      crosslinkable unit
<220> FEATURE:
<221> NAME/KEY: REPEAT
<222> LOCATION: (6)..(6)
<223> OTHER INFORMATION: 3 to 30 aspartic acid residues

<400> SEQUENCE: 80

Cys Val Glu Ile Asp Asp
1               5

<210> SEQ ID NO 81
<211> LENGTH: 6
<212> TYPE: PRT
<213> ORGANISM: Artificial Sequence
<220> FEATURE:
<223> OTHER INFORMATION: Peptide linkage with consensus sequence and
      crosslinkable unit
<220> FEATURE:
<221> NAME/KEY: REPEAT
<222> LOCATION: (6)..(6)
<223> OTHER INFORMATION: 3 to 30 glutamic acid residues

<400> SEQUENCE: 81
```

```
Cys Val Glu Ile Asp Glu
1               5

<210> SEQ ID NO 82
<211> LENGTH: 8
<212> TYPE: PRT
<213> ORGANISM: Homo sapiens

<400> SEQUENCE: 82

Ala Arg Val Leu Ala Glu Ala Met
1               5
```

PROTEASE SELECTIVE SUPRAMOLECULAR ASSEMBLIES

CROSS-REFERENCE TO RELATED APPLICATIONS

The present application is a continuation-in-part of International Application Serial No. PCT/US2011/053711, filed Sep. 28, 2011, which claims the priority benefit of U.S. Provisional Patent Application Ser. No. 61/387,870, filed Sep. 29, 2010, entitled Protease Selective Liposomes, which are both incorporated by reference in their entirety herein.

SEQUENCE LISTING

The following application contains a sequence listing in computer readable format (CRF), submitted as a text file in ASCII format entitled "SequenceListing," created on Mar. 12, 2013, as 19 KB. The content of the CRF is hereby incorporated by reference.

BACKGROUND OF THE INVENTION

1. Field of the Invention

The present invention relates to supramolecular assemblies as delivery vehicles for detecting, imaging, and treating target tissues, such as cancerous or precancerous tissue.

2. Description of Related Art

A number of proteases are associated with disease progression in cancer, and are known to be over-expressed by various cancer cell lines, as shown in FIG. 1. Examples include Matrix Metalloproteinases (MMPs), Tissue Serine Proteases, and the Cathepsins. Many of these proteases are either upregulated in the cancer cells (i.e., have a much higher activity in the tumor than in healthy tissue), mis-expressed (i.e., are found in compartments where they should not be found), or are involved in embryonic development (but should not be found to any significant extent in an adult cell). As shown in FIG. 1, the stages of disease progression are separated into four events: initial mutation, cell survival/tumor progression, angiogenesis (development of new blood vessels), and invasion/tissue remodeling. The array of proteases associated with each stage can give a good picture of how far the cancer has progressed and what the prognosis will be.

There are 21 different known MMPs that are grouped into families based on their substrates: collagenases, gelatinases, stromelysins, matrilysin, metalloelastase, enamelysin, and membrane-type MMPs. MMPs are usually produced by stromal cells surrounding a tumor, and although not produced by the cancerous cells themselves, are vital to cancer survival and progression for several reasons. First, they cleave cell surface bound growth factors from the stromal and epithelial cells and release them to interact with the cancer cells to stimulate growth. Second, they play a role in angiogenesis by opening the extracellular matrix (ECM) to new vessel development as well as by releasing pro-angiogenic factors and starting pro-angiogenic protease cascades. MMPs play a major role in tumor metastasis by degrading the ECM and the basement membrane (BM), allowing the cancer cells to pass through tissue barriers, leading to cell invasion. They also release ECM and BM fragments, which stimulates cell movement.

Several serine proteases have well-documented roles in cancer as well, especially urokinase plasminogen activator (uPA) and plasmin Elevated expression levels ofurokinase and several other components of the plasminogen activation system have been found to be correlated with tumor malignancy. uPA is a very specific protease that binds to its receptor, uPAR, and cleaves the inactive plasminogen (a zymogen) to the active plasmin. This is the first step in a well-known cascade that causes angiogenesis in tumors. It is believed that the tissue degradation that follows plasminogen activation facilitates tissue invasion and contributes to metastasis. Plasmin is a somewhat non-specific protease that goes on to cleave proteins or peptides including activating procollagenases, degrading the ECM, and releasing/activating growth factors. Although plasmin is somewhat non-specific and a consensus sequence is hard to determine, uPA does have a well-defined consensus sequence (SEQ ID NO: 1).

Cathepsins, with a few exceptions, are cysteine proteases. Often found in the lysosomal/endosomal pathway, cathepsins usually operate at low pH values, but some are still active at neutral pH. Three of the cathepsins, B, D, and L, are active at neutral pH and are often misexpressed in cancer, causing activation outside of the cells. This activation outside of the cell can cause ECM degradation.

A major reason cancer therapy fails is that the undesired side effects of most cancer drugs limit the amount of the drug that can be delivered systemically and thus the amount of drug that is ultimately delivered to the tumor. A more specific method of delivery would decrease systemic delivery (and thus unwanted side effects) and increase tumor delivery (increasing effectiveness of the drug). Such a therapy would be much less likely to fail because of low dosages or be stopped by the patient due to overwhelming side effects. In addition, despite recent advances, there remains a need for improved detection and imaging of cancerous tissues.

SUMMARY OF THE INVENTION

The present invention is broadly concerned with protease-sensitive supramolecular assemblies. In one aspect, the supramolecular assembly comprises a liposome comprising a membrane defining an interior space; a crosslinked, polymeric coating adjacent the membrane, the coating comprising a protease consensus sequence; and an active agent encapsulated in the liposome, wherein the active agent is dissolved or dispersed in a pharmaceutically-acceptable carrier or excipient.

The invention is also concerned with diagnostic and/or therapeutic compositions comprising a plurality of protease-sensitive supramolecular assemblies according to the various embodiments described herein, optionally dispersed in a pharmaceutically-acceptable carrier or excipient.

A dried composition comprising a plurality of protease-sensitive supramolecular assemblies is also provided. The assemblies comprise a liposome comprising a membrane defining an interior space; a crosslinked, polymeric coating adjacent the exterior surface of the membrane, wherein the coating comprises a protease consensus sequence; and an active agent encapsulated in the liposome, wherein the active agent is dissolved or dispersed in a pharmaceutically-acceptable carrier or excipient in the interior space.

A method of detecting the activity of a protease associated with a cancerous or precancerous cell or cancer stem cell in a subject is also provided. The method comprises contacting a sample comprising biological fluid from the subject with a diagnostic assay, wherein the assay comprises a supramolecular assembly as described herein, and wherein the active agent is a salt; and detecting a change in the electrical current of the sample, wherein the change correlates to the protease activity which releases the salt from the supramolecular assembly.

The invention also provides a further method of detecting the activity of a protease associated with a cancerous or precancerous cell or cancer stem cell in a subject. The method comprises contacting a sample comprising biological fluid from the subject with a diagnostic assay, wherein the assay comprises a supramolecular assembly as described herein, and wherein the active agent is a (self-quenched) dye; and detecting the emission spectrum of the dye, wherein the emission spectrum correlates to the protease activity which releases the previously-quenched dye from the supramolecular assembly.

A further method of detecting the activity of a protease associated with a cancerous or precancerous cell or cancer stem cell or imaging cancerous tissue in a subject is also provided. The method comprises administering to the subject a supramolecular assembly as described herein, wherein the active agent is a self-quenched dye; and detecting the emission spectrum of the dye, wherein the emission spectrum correlates to the protease activity which releases the previously-quenched dye from the supramolecular assembly.

The invention also provides a method of treating a disease or condition associated with protease activity in a subject. The method comprises administering to the subject a therapeutically effective amount of a supramolecular assembly as described herein, wherein the active agent is a therapeutic agent, and wherein the supramolecular assembly accumulates in and near the protease activity in the subject to deliver the therapeutic agent thereto.

A kit for detection or treatment of a disease or condition associated with protease activity in a subject is also provided. The kit comprises a composition comprising a plurality of protease-sensitive supramolecular assemblies; and instructions for the administration thereof. The assemblies comprise a liposome comprising a membrane defining an interior space; a crosslinked, polymeric coating adjacent the membrane, wherein the coating comprises a protease consensus sequence; and an active agent encapsulated in the liposome, wherein the active agent is dissolved or dispersed in a pharmaceutically-acceptable carrier or excipient.

The invention also provides a composition comprising a first supramolecular assembly as described herein comprising a first protease consensus sequence and a first active agent; and a second supramolecular assembly as described herein comprising a second protease consensus sequence and a second active agent, the second protease consensus sequence and the second active agent being different from the first protease consensus sequence and the first active agent.

A method of detecting the activity of a first protease associated with a cancerous or precancerous cell in a subject and a second protease associated with a cancerous or precancerous cell in a subject is also provided. The method comprises administering to a subject a composition as described immediately above, wherein the first protease consensus sequence corresponds to the first protease and the second protease consensus sequence corresponds to the second protease, wherein the first active agent is a first dye and the second active agent is a second dye; and detecting the emission spectrum of the composition, wherein the emission spectrum of the first dye indicates activity of the first protease and the emission spectrum of the second dye indicates activity of the second protease, the emission spectrum of the first dye being different from the second dye.

The invention is also concerned with a protease-sensitive supramolecular assembly comprising a first macrocycle comprising a dye and a peptide linkage, wherein the peptide linkage comprises a protease consensus sequence; a second macrocycle mechanically interlocked with the first macrocycle, wherein the second macrocycle also comprises a dye; and a targeting moiety attached to either of the first or second macrocycles, wherein the emission spectrum of the dyes is self-quenched in the assembly.

A further protease-sensitive supramolecular assembly is also provided. The assembly comprises a linear molecule having respective ends and comprising a peptide linkage, wherein the peptide linkage comprises a protease consensus sequence; a plurality of macrocycles, the linear molecule being threaded through the macrocycles, wherein the macrocycles each comprises a respective dye; and a stopper molecule at each of the ends, wherein each stopper molecule is larger than the interior diameter of each of the macrocycles such that the macrocycles are mechanically interlocked with the linear molecule, and wherein the emission spectrum of the dyes is self-quenched.

BRIEF DESCRIPTION OF THE DRAWINGS

Figure (FIG.) 1 is a flow-chart showing the progression of cancer and associated proteases.

DETAILED DESCRIPTION

Figure 1:
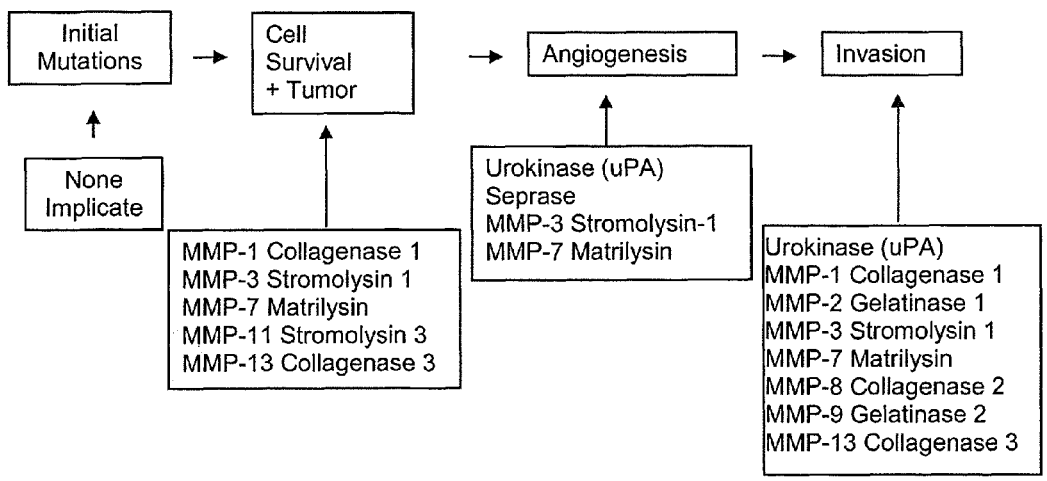

The present invention is concerned with delivery vehicles (i.e., supramolecular "assemblies" or "containers") and methods of using the same to quickly release active agents in the presence of target tissue, while remaining stable until the point of release. More specifically, these supramolecular assemblies (used interchangeably herein with the terms vehicle or container) are designed to release their contents or cargo (i.e., the active agents) upon interaction with a specific protease associated with cancer allowing the active agent to be targeted to the cancerous tissue. These supramolecular assemblies also permit selective imaging and detection of cancerous tissue, including the diagnosis of cancer progression. In addition, diagnosis and therapeutic treatment of target tissue can be carried out simultaneously ("theranostics"). The term "supramolecular," as used herein, refers to nano-sized delivery vehicles in which, or on which, the active agents to be delivered are not covalently (or otherwise chemically) bound to the delivery vehicle structure, but are instead physically or mechanically contained within or retained by the delivery vehicle structure. Upon degradation of some portion of the supramolecular assembly by a protease, the active agents are released.

In one aspect of the invention, there is provided polymer-caged liposomes for delivering active agents to cancerous tissue. Liposomes have the ability to fuse membranes with a target cell, releasing their contents directly into the cell. The inventive liposomes comprise a membrane, defining a liquid-receiving or liquid-containing interior space (cavity) in which the active agents are contained, and a crosslinked, polymeric coating adjacent the membrane. The liposome membrane comprises phospholipids and cholesterol and is preferably unilamellar (i.e., single bilayer, as opposed to multiple bilayers). Suitable phospholipids for use in forming the liposome membrane include natural and synthetic phospholipids, as well as phospholipid derivatives. Particularly preferred phospholipids are selected from phosphatidylcholines, such as L-α-lysophosphatidylcholine 1,2-dipalmitoyl-sn-glycero-3-phosphocholine (DOPC), 1,2-dioleoyl-sn-glycero-3-phosphocholine (DPPC), 1,2-dilauroyl-sn-glycero-3-phosphocholine (DLPC), 1,2-dimyristoyl-sn-glycero-3-phosphocholine (DMPC), 1,2-distearoyl-sn-glycero-3-phosphocholine (DSPC), 1,2-diarachidoyl-sn-glycero-3-phosphocholine (DAPC), 1,2-dierucoyl-sn-glycero-3-phosphocholine (DEPC), and/or 1-palmitoyl-2-oleoyl-sn-glycero-3-phosphocholine (POPC). Combinations of one or more of the above phospholipids can also be used. The amount of phospholipid in the membrane preferably ranges from about 20 to about 99% by weight, more preferably from about 40 to about 80% by weight, and even more preferably from about 45% to about 65% by weight, based upon the total weight of the membrane constituents taken as 100% by weight. When present, the amount of DOPC preferably ranges from about 40 to about 90% by weight, more preferably from about 35 to about 70% by weight, and even more preferably from about 40 to about 60% by weight, based upon the total weight of the membrane constituents taken as 100% by weight. When present, the amount of DPPC preferably ranges from about 1 to about 25% by weight, more preferably from about 3 to about 15% by weight, and even more preferably from about 5 to about 10% by weight, based upon the total weight of the membrane constituents taken as 100% by weight. The amount of cholesterol in the membrane preferably ranges from about 10 to about 60% by weight, more preferably from about 20 to about 50% by weight, and even more preferably from about 25 to about 45% by weight, based upon the total weight of the membrane constituents taken as 100% by weight. The ratio of total phospholipid to cholesterol is preferably from about 1:2 to about 10:1, more preferably from about 1:1 to about 5:1, and even more preferably from about 5:3 to about 5:1.

The membrane thickness will depend upon the constituents, but will preferably be from about 1 nm to about 10 nm and more preferably about from about 4 nm to about 5 nm. The liposomes are preferably generally spherical in shape. The liposomes preferably have an average maximum surface-to-surface dimension (i.e., diameter in the case of spherical-shaped liposomes) of from about 50 nm to about 1 μm, more preferably from about 100 nm to about 500 nm, and even more preferably from about 125 nm to about 200 nm.

The crosslinked, polymeric coating adjacent the lipo some membrane comprises a protease consensus sequence and is formed from a polymer crosslinked via a crosslinking agent. The protease consensus sequence can be present as part of the polymer and/or as part of the crosslinking agent, and in either case is generally provided in a peptide linkage. Peptide linkages will comprise a consensus sequence for a cancer-associated protease to permit selective degradation of the crosslinked, polymeric coating in the presence of cancerous tissue. Preferably, the consensus sequence used in the peptide linkage is selected from the group consisting of serine protease cleavage sequences, aspartyl protease cleavage sequences, cysteine protease cleavage sequences, and metalloprotease cleaveage sequences. Even more preferably, the consensus sequence comprises a cleavage/consensus sequence for a protease selected from the group consisting of urokinase, matrix metallopeptidase, cathepsin, and gelatinase. Particularly preferred proteases and their corresponding consensus sequences are listed in Table I below.

TABLE I

Protease Sequences

| Protease | Consensus Sequence (Cleavage Sequence) |
|---|---|
| uPA | SGRSA (SEQ ID NO: 1) |
| MMP-1 | VPMSMRGG (SEQ ID NO: 2 and variants thereof which may be deleted at the C-terminus by 1 residue) |
| MMP-2 | IPVSLRSG (SEQ ID NO: 3) |
| MMP-3 | RPFSMIMG (SEQ ID NO: 4) |
| MMP-7 | VPLSLTMG (SEQ ID NO: 5) |
| MMP-9 | VPLSLYSG (SEQ ID NO: 6) |
| MMP-11 | HGPEGLRVGFYESDVMGRGHARLVHVEEPHT (SEQ ID NO: 7)<br>GAANLVRG (SEQ ID NO: 8) |
| MMP-13 | GPQGLAGQRGIV (SEQ ID NO: 9) |
| MMP-14 | IPESLRAG (SEQ ID NO: 10) |
| Cathepsin B | SLLKSRMVPNFN (SEQ ID NO: 11)<br>DAFK (SEQ ID NO: 12) |
| Cathepsin D | SLLIFRSWANFN (SEQ ID NO: 13)<br>SGKPILFFRL (SEQ ID NO: 14) |
| Cathepsin E | SGSPAFLAKNR (SEQ ID NO: 15)<br>SGKPIIFFRL (SEQ ID NO: 16) |
| Cathepsin K | PRAGA (SEQ ID NO: 17) |
| Cathepsin L | SGVVIATVIVIT (SEQ ID NO: 18) |
| Gelatinase | GPLGMISQ (SEQ ID NO: 19) |

TABLE I-continued

Protease Sequences

| Protease | Consensus Sequence (Cleavage Sequence) |
|---|---|
| Caspases 3, 7 | DEVDG (SEQ ID NO: 74) |
| Caspase 6 | DEVDG (SEQ ID NO: 74)<br>VEID (SEQ ID NO: 75) |

Combinations of consensus sequences can be used in the crosslinked, polymeric coating, either as part of the same peptide linkage, or as different peptide linkages. Similarly, one type of consensus sequence can be provided as part of the polymer, while another consensus sequence can be provided as part of the crosslinking agent. The peptides can be purchased, or they can be synthesized using known methods (e.g., modified Merrifield synthesis). The most preferred peptide sequences for select proteases are listed in the table below with the point of cleavage indicated by "-".

TABLE II

Peptide Linkages

| Protease | Preferred Oligopeptide with Consensus Sequence |
|---|---|
| uPA | GSGR-SAGC (SEQ ID NO: 20)<br>GSGR-SAGK (SEQ ID NO: 21)<br>KGGGSGR-SAGGGC (SEQ ID NO: 22)<br>CGGGSGR-SAGGC (SEQ ID NO: 23)<br>CGGGSGR-SAGGGC (SEQ ID NO: 24)<br>DGGSGR-SAGGK (SEQ ID NO: 25)<br>SRSRSRSRSRSGR-SAGGGC (SEQ ID NO: 26)<br>KGGSGR-SAGGD (SEQ ID NO: 27)<br>CGGGSGR-SAGGG (SEQ ID NO: 28)<br>DGGGSGR-SAGGGD (SEQ ID NO: 29)<br>DGAGSGR-SAGAGD (SEQ ID NO: 30 and variants thereof, which may be deleted at the N-terminus by 1 residue and C-terminus by 1 or 2 residues)<br>KGGSGR-SAGGG (SEQ ID NO: 31)<br>DGGSGR-SAGGGC (SEQ ID NO: 32)<br>HHHGAGSGR-SAGAG (SEQ ID NO: 33)* |
| MMP-1 | KGGVPMS-MRGGGC (SEQ ID NO: 34)<br>HHHGAGVPMS-MRGAG (SEQ ID NO: 35)* |
| MMP-2 | KGGIPVS-LRSGGC (SEQ ID NO: 36)<br>HHHGAGIPVS-LRSGAG (SEQ ID NO: 37)* |
| MMP-3 | HHHGAGRPFS-MIMGAG (SEQ ID NO: 38)* |
| MMP-7 | KGGVPLS-LTMGGC (SEQ ID NO: 39)<br>HHHGAGVPLS-LTMGAG (SEQ ID NO: 40)* |
| MMP-9 | HHHGAGVPLS-LYSGAG (SEQ ID NO: 41)* |
| MMP-11 | HHHGAGGAAN-LVRGAG (SEQ ID NO: 42)* |
| MMP-13 | HHHGAGPQGLA-GQRGIVGAG (SEQ ID NO: 43)* |
| Cathepsin B | HHHGAGSLLKSR-MVPNFNGAG (SEQ ID NO: 44)* |
| Cathepsin D | HHHGAGSLLIFR-SWANFNGAG (SEQ ID NO: 45)* |
| Cathepsin L | HHHGAGSGVVIA-TVIVITGAG (SEQ ID NO: 46)* |
| Cathepsin K | HHHGAGPR-AGAG (SEQ ID NO: 47)* |

TABLE II-continued

Peptide Linkages

| Protease | Preferred Oligopeptide with Consensus Sequence |
|---|---|
| Caspases 3, 7 | CDE-VDG(K)$_x$ (SEQ ID NO: 76)<br>CDE-VDG(D)$_x$ (SE IQ DNO: 77)<br>CDE-VDG(E)$_x$ (SEQ ID NO: 78),<br>where x is 3-30. |
| Caspase 6 | CDEVD-G(K)$_x$ (SEQ ID NO: 76)<br>CDEVD-G(D)$_x$ (SE IQ DNO: 77)<br>CDEVD-G(E)$_x$ (SEQ ID NO: 78),<br>where x is 3-30.<br>CVE-ID(K)$_x$ (SEQ ID NO: 79)<br>CVE-ID(D)$_x$ (SE IQ DNO: 80)<br>CVE-ID(E)$_x$ (SEQ ID NO: 81),<br>where x is 3-30 |

*(including variants thereof, which may be deleted at the N-terminus by 1, 2, or 3 residues)

The polymer generally comprises a membrane anchor, a crosslinkable unit, and optionally a peptide linkage comprising a protease consensus sequence. In one or more embodiments, the polymer comprises an anchor end and a crosslinkable end remote from the anchor end, with the peptide linkage in between. In one or more embodiments, the crosslinkable unit is between the anchor end and the peptide linkage. In some embodiments, the polymers are individual linear chains, wherein the membrane anchor, crosslinkable unit, and optional peptide linkage make up the chain (backbone). In other embodiments branched polymers can be used. In one or more embodiments, the membrane anchor is embedded in the liposome membrane. Suitable anchors include cholesterol, cholesterol derivatives, and other steroids (e.g., prednisone, estradiol, testosterone, dexamethasone, cholestane, etc.), $C_{16}$ and higher fatty acids preferably containing at least one double-bond, and/or cell-penetrating peptides (e.g., Penetratin™). Exemplary fatty acids suitable for use as anchors are listed in the table below.

TABLE III

Fatty Acid Anchors

| Common name | C's | Double bonds | IUPAC name |
|---|---|---|---|
| Palmitoleic Acid | 16 | 1 | 9-hexadecenoic acid |
| Oleic Acid | 18 | 1 | 9-octadecenoic acid |
| Ricinoleic acid | 18 | 1 | 12-hydroxy-9-octadecenoic acid |
| Vaccenic Acid | 18 | 1 | 11-octadecenoic acid |
| Linoleic Acid | 18 | 2 | 9,12-octadecadienoic acid |
| Alpha-Linolenic Acid (ALA) | 18 | 3 | 9,12,15-octadecatrienoic acid |
| Gamma-Linolenic Acid (GLA) | 18 | 3 | 6,9,12-octadecatrienoic acid |
| Gadoleic Acid | 20 | 1 | 9-eicosenoic acid |
| Arachidonic Acid (AA) | 20 | 4 | 5,8,11,14-eicosatetraenoic acid |
| EPA | 20 | 5 | 5,8,11,14,17-eicosasentaenoic acid |
| Erucic acid | 22 | 1 | 13-docosenoic acid |
| DHA | 22 | 6 | 4,7,10,13,16,19-docosahexaenoic acid |

Other suitable anchors and their associated coupling reagent(s) are shown in the table below.

TABLE IV

Additional Membrane Anchors

| Membrane Anchor | Coupling Reagent |
|---|---|
| Cholesterol derivative (n = 0-10) featuring a terminal carboxylic acid | ECD$^a$/HBTU$^b$ in DMF$^c$/DIEA$^d$ |

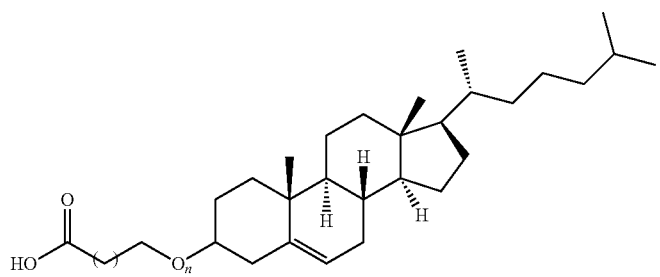

| | |
|---|---|
| Isoprenyl (e.g., Farnesyl-group, Geranylgeranyl-group) | CDI$^e$ in DMF |

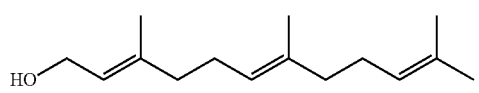

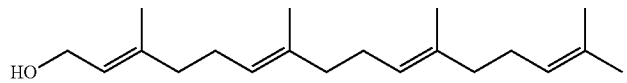 [SMILES: CC(C)=CCC/C(C)=C/CC/C(C)=C/CC/C(C)=C/CO]

TABLE IV-continued

Additional Membrane Anchors

| Membrane Anchor | Coupling Reagent |
|---|---|
| Myrsitoyl 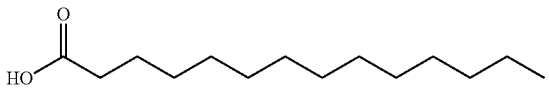 | EDC/HBTU in DMF/DIEA |
| Palmitoyl 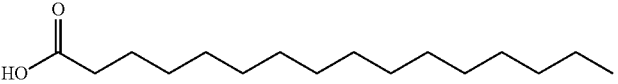 | EDC/HBTU in DMF/DIEA |

[a]1-ethyl-3-(3-dimethylaminopropyl)carbodiimide (EDC).
[b]O-Benzotriazole-N,N,N',N'-tetramethyl-uronium-hexafluoro-phosphate (HBTU).
[c]Dimethylformamide (DMF).
[d]N,N-Diisopropylethylamine (DIEA).
[e]CarbonyldiImidazole (CDI).

The anchor can be embedded in the membrane via known methods, including allowing the anchor to diffuse into the membrane (e.g., via hydrophobic interactions) or adding anchors to the lipid mixture used to form the liposome (described below), such that the anchors will already be present in the membrane once the liposome is formed. The crosslinkable unit and optional peptide linkage can be attached to the anchor before making the liposomes or after the liposomes have been formed. In one or more embodiments, the polymer will be present in the assembly at a level of from about 1% to about 50% by weight, and more preferably from about 5 to about 25% by weight, based upon the total weight of the caged liposome taken as 100% by weight. Regardless, once the polymer is anchored into the liposome membrane, it is crosslinked via the crosslinkable unit.

Exemplary crosslinkable units will include functional groups selected from the group consisting of carboxylic acids (e.g., as functional groups of polyacrylic acid, methacrylic acid, poly-N-isopropyl-acrylamide, copolymers of substituted acrylates and methacrylates), hydroxyl groups (e.g., in polyvinylacohol, ethylene glycol and higher aliphatic and aromatic diols, glycerol, oligoethylene glycol), epoxides (e.g, epichlorhydrin and epichlorhydrin-modified polymers), amines (e.g., the terminal ends of polycondensation polymers, such as polyamides, amino-functionalized oligoethylene glycol, polyethylene-imine), thiols (e.g., cysteine-containing oligopeptides), haloalkanes (e.g., in polyvinylchloride and organic dihalides), and systems capable of cyloaddition (or "click chemistry," e.g., diazo-compounds and ethynes (1,3-dipolar cycloaddition) or azide alkyne Huisgen cycloaddition). Crosslinkable units can also be formed using positively- and negatively-charged amino acids in the polymer chain, as discussed in more detail below. The molar ratio of crosslinker to the polymer's or copolymer's repeating units preferably ranges from about 1:2 to about 1:50, more preferably from about 1:4 to about 1:25, and even more preferably from about 1:5 to 1:10.

In one or more embodiments, the polymer preferably comprises an anchor, a peptide linkage, and a crosslinkable polymeric unit, with the peptide linkage being between the anchor and crosslinkable polymeric unit. In the polymer, the peptide linkage is adjacent the anchor, with the anchor being attached to the N-terminal end of the peptide linkage. The anchor preferably comprises an acidic terminal end, or is acid-functionalized to facilitate attachment to the peptide linkage. The anchor and peptide linkage can be attached using any suitable method, including EDC coupling as described herein, or any of the other coupling mechanisms mentioned in Table IV above. The crosslinkable polymeric unit is adjacent the C-terminal end of the peptide linkage. The polymeric unit is preferably amine-terminated or amine-functionalized on one end to facilitate attachment to the peptide linkage. Suitable crosslinkable polymeric units will be hydrophilic, water-soluble, and capable of being crosslinked, such as polyacrylic acid. The term "polymeric," as used herein with respect to the crosslinkable polymeric unit, is intended to encompass monomers, oligomers, and/or polymers. The weight average molecular weight (Mw) of the polymeric unit is preferably from about 1,000 to about 100,000 Daltons, more preferably from about 5,000 to about 75,000 Daltons, and even more preferably from about 8,000 to about 25,000 Daltons. The crosslinkable polymeric unit and peptide linkage can be attached using any suitable method, including EDC coupling, as described herein. Thus, in one or more embodiments, the polymer is a cholesterol-anchored, di-block (peptide linkage and acrylic acid) copolymer.

In one or more embodiments, the polymer is an oligopeptide comprising (consisting essentially or even consiting of) a membrane anchor as described above, a crosslinkable unit, and a peptide linkage comprising a protease consensus sequence, with the crosslinkable unit between (and immediately adjacent to) the anchor and peptide linkage, respectively. The peptide linkage will comprise a consensus sequence such as those described herein, and may further include a terminal cysteine group. The crosslinkable unit comprises repeating amino acids having either a positive or negative charge in buffered aqueous solution (e.g., PBS, HEPES buffer, with pH from about 6 to about 8). Positively-charged amino acid chains include lysine chains having from about 3 to about 30 sequential lysine residues. Negatively-charged amino acid chains include glutamic acid or aspartic acid chains having from about 3 to about 30 sequential amino acid residues. A mixture of positively- and negatively-charged polymers can be used to create a supramolecular network at the liposome surface due to the charge-attraction between the two types of polymers. Thus, in forming the caged liposomes, positively-charged polymers and negatively-charged polymers are preferably mixed in a ratio of 1 molecule positively-charged polymer to 1 molecule negatively-charged polymer. The total amount of positively- and negatively-charged polymer will depend on the size of the liposome. In general, about 1 positively-charged molecule and 1 negatively-charged molecule can be used for every 10 to about 500 phospholipid molecules (used in forming the liposome membrane, as described below). The mixture can then be incubated for about 1 to about 24 hours to allow the positively- and negatively-charged polymers to associate into the supramolecular network before crosslinking.

In one or more embodiments, the polymer is a branched polymer, and preferably a tri-functional branched polymer. Branched polymers can be formed by attaching respective (linear) polymer chains, described above, to a tri-functional core, with the polymer chains radiating outwards therefrom. Thus, in one or more embodiments, suitable polymers for use in the invention will comprise (consist essentially or even consist of) a membrane anchor, a crosslinkable unit, a peptide linkage comprising a protease consensus sequence, and a tri-functional core. The tri-functional core will generally comprise a central monomer, compound, or molecule with three arms radiating therefrom, which typically terminate in respective reactive groups (e.g., carboxylic acid, alcohol, amine, etc.) to facilitate bonding to the polymer chain. Suitable cores will include derivatives of nitriloacetic acid, and other trifunctional carboxylic acids (e.g. methanetricarboxylic acid, cyclohexane-1,3,5-tricarboxylic acid, 2,2',2''-(benzene-1,3,5-triyl)iacetic acid, benzene-1,3,5-tricarboxylic acid), trifunctional amines (e.g., 2-(aminomethyl)propane-1, 3-diamine, benzene-1,3,5-triamine, benzene-1,3,5-triyltrimethanamine, benzene-1,3,5-triamine, 1,3,5-triazine-2,4,6-triamine, adamantane-2,4,9-triamine), and the like. The core may further comprise spacer moieties attached via the terminal reactive groups to facilitate suitable spacing of the polymer chains when attached. Exemplary spacer moieties include maleimides, active esters of carboxylic acids, thiols, and the like. In some embodiments, maleimide spacers are particularly preferred for their ability to react with thiol from the terminal cysteine of the peptide linkage under Michael addition. Thus, the attachment point to the tri-functional core is preferably through the peptide linkage in some embodiments. Once the polymer chains are attached to the tri-factional core, each arm of the branched polymer will comprise a peptide linkage, crosslinkable unit, and terminate in a respective membrane anchor.

Regardless of the embodiment, the anchor end of the polymer is embedded in the liposome membrane. Essentially, the membrane anchors ensure that the polymers remain adsorbed at the outer phospholipid/water interface on the liposome outer membrane. Thus, in one aspect, the liposome comprises a plurality of polymers embedded in the liposome membrane. The polymers are crosslinked via their respective crosslinkable units with a crosslinking agent. In the case of positively- and negatively-charged branched polymers, the polymers will associate into a network having hexagonal geometry. The opposing positively- and negatively-charged crosslinkable units can then be crosslinked using a suitable crosslinking agent, such as EDC. Regardless of the embodiment, crosslinking results in a crosslinked "cage" surrounding the liposome that is also covalently bound to the liposome membrane. The cage spacing (i.e., distance between bars of the crosslinked network) will depend up on the polymer concentration, crosslinker, and relative concentrations of polymer to crosslinker, but will usually range from about 1 nm to about 20 nm. The desired spacing will also depend upon the active agent to be contained within the liposome. For example, in the case of smaller active agents, such as salts and ions, the spacing is preferably from about 1 to about 5 nm, and more preferably about 3 nm. In the case of most small molecule drugs, the spacing is preferably from about 2 to about 8 nm, and more preferably from about 4 to about 5 nm. For larger active agents, including certain types of biologics, such as DNA and RNA, the spacing can range from about 5 to about 20 nm, and more preferably from about 10 to about 15 nm.

Suitable crosslinking agents will depend upon and preferably correspond to the functionalization of the crosslinkable unit. For example, amine-based crosslinking agents are particularly preferred for use with crosslinkable polymeric units comprising carboxylic acids or hydroxy groups (reaction with EDC or other carbodiimides). Other pairings are known in the art, including without limitation, amine-amine (reaction with carbonyl-bis-imidazole (CDI), amine-hydroxy (CDI), hydroxy-hydroxy (CDI) or thiol-thiol (air-oxidation or reaction with choramine T), etc., and can be selected accordingly. In one or more embodiments, the crosslinking agent is a diamine (e.g., ethylenediamine, propylenediamine, butylenediamine, lysine, etc.). To further facilitate degradation of the polymer cage, the crosslinking agent itself can include (or even consist of) a peptide linkage comprising a protease consensus sequence, such as the sequences described above. In the case of diamine crosslinkers, a suitable peptide can be modified to include an N-terminal amine and C-terminal lysine amine. Other suitable crosslinking agents include peptides having an N-terminal amine and C-terminal cysteine. In general, suitable crosslinking agents are selected from the group consisting of amines, hydroxys, thiols, and carboxylic acids. Combinations of crosslinking agents can also be used to make liposomes react with more than one protease.

Thus, in some embodiments, such as embodiments where the polymer comprises a consensus sequence, the crosslinked, polymeric coating can comprise a separate crosslinking agent, such as ethylenediamine and/or a further peptide linkage, mentioned above. In other embodiments, the polymer comprises an anchor and crosslinkable unit, with the crosslinking agent being the peptide linkage itself. In this embodiment, the peptide linkage is attached at one end to the crosslinkable end of a first polymer (which is embedded in the membrane of the liposome) and attached at the other end to the crosslinkable end of a second polymer (which is also embedded in the membrane of the liposome). In this way, a plurality of polymers and peptide linkages can be used to form a network or cage around the liposome. It will be appreciated that regardless of the embodiment, the crosslinkable unit of the polymer can include multiple crosslinkable functional groups, such that more than one crosslinking agent can be attached to the crosslinkable unit of each polymer.

Figure 2:
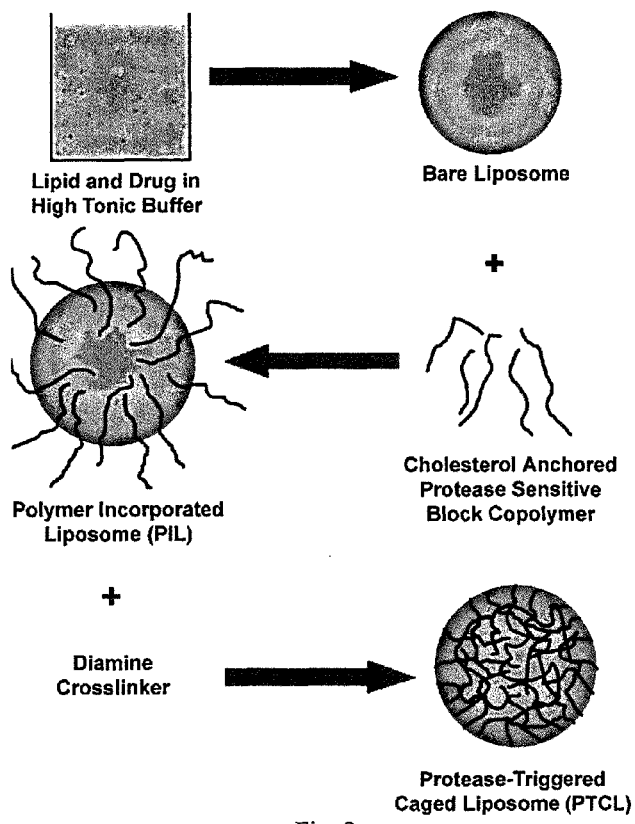
FIG. 2 is a schematic illustrating formation of liposome supramolecular assemblies according to one embodiment of the invention.

The liposomes are formed by dissolving the membrane components (e.g., phospholipids and cholesterol) in an organic solvent in the desired ratios or amounts, along with the optional membrane anchor. Suitable solvents include chloroform, tetrahydrofurane, dimethylfurane, dimethyltetrahydrofurane, methanol and/or ethanol. Once mixed, the solvent is then removed, preferably under vacuum, to produce a dried mixture comprising, and preferably consisting of, the the mixed phospholipids and cholesterol (generally in the form of a thin layer on the bottom of the mixing vessel). Any solutes (active agents) to be trapped or contained in the liposomes are then dissolved or dispersed in an aqueous solvent system, which is then added to the dried mixture. The lipid film is then dispersed into the aqueous solvent system. The liposomes self-assemble and form around the solutes dissolved or dispersed in the solvent system, entrapping the solutes therein. The liposomes are then separated from the unentrapped solutes and solvent system using any suitable method to yield liposomes comprising active agents contained therein. The polymer is then attached or incorporated into the liposome membrane in a solvent system, as described above, and then crosslinked to yield the polymer-caged liposomes. An exemplary depiction of this process is shown in FIG. 2.

Those skilled in the art will appreciate that the dispersion step is important in terms of controlling the liposome characteristics (e.g., size, lamellarity, dispersity, etc.). Depending upon the dispersion method, multilamellar liposomes, large unilamellar liposomes, or small unilamellar liposomes result. Dispersion methods are known in the art and include mechanical dispersion (e.g., hand shaking, passive non-shaking, sonication, freeze-drying, microemulsification, freeze-thaw, membrane extrusion, etc.), solvent dispersion (e.g., ethanol injection, ether injection), and/or detergent solubilization. Combinations of dispersion methods can also be used. In a preferred method, the hydrated mixture is preferably mechanically mixed via vortexing and/or sonication to sufficiently suspend the lipid/cholesterol mixture in the solvent system. The suspension is then preferably subjected to a series of freeze-thaw cycles, followed by purification and separation of the prepared liposomes from the unentrapped solutes and solvent system. Preferably, liposomes used according to the invention have a high degree of monodispersity.

The liposomes are preferably prepared in a hypertonic (i.e., highly concentrated) solvent system, so that the resulting liposomes are intrinsically unstable in hypotonic or isotonic environments, such as physiological environments. Physiological environments include in vivo environments, such as in the bloodstream, interstitial fluid, and intracellular matrix, or in vitro such as in biological fluids collected from a subject, including blood and/or urine. Thus, the liposomes are preferably hypertonic and contain a higher concentration of solutes (have a greater effective osmole concentration) compared to the external physiological environment, such that water from the external environment will have a tendency to cross the semi-permeable lipid membrane to dilute the internal solutes and bring the system into equilibrium; however, this will also cause the osmotic pressure in the liposomes to increase, such that the liposomes will eventually swell and burst, releasing their contents. Advantageously, the crosslinked, polymeric coating will stabilize the liposomes by providing significant osmotic pressure resistance, preventing them from bursting and releasing their contents until the coating is degraded by the proteases in the vicinity of the target tissue. This swelling also facilitates (and can even enhance the rate of) fusion of the liposomes with the target cell membranes to permit release of the liposome contents directly into the cells. Preferably, the tonicity of the interior of the liposomes is from about 1× to about 20× more than normal physiological solute concentration, more preferably from about 5× to about 10×, with about 10× being particularly preferred. The term "normal physiological solute concentration" refers to a solution of 0.90% w/v of NaCl about 300 mOsm/L or 9.0 g per liter. Less commonly, this solution is also referred to as physiological saline or isotonic saline. (Mansoor M. Amiji, Beverly J. Sandmann (2002). *Applied Physical Pharmacy* McGraw-Hill Professional. pp. 54-57. ISBN 0071350764.)

Advantageously, once the polymer-caged liposomes are formed, the solvent system can be removed, e.g., under vacuum, to yield a dried mixture of polymer-caged liposomes comprising the active agents entrapped therein. That is, the interior liquid remains inside the liposomes along with the active agent, however, the exterior moisture (i.e., solvent system) is dried off to yield a liposomal powder having an exterior moisture content of less than about 40%, more preferably less than about 20% by weight, and even more preferably less than about 10% by weight, based upon the total weight of the dried liposomes taken as 100% by weight. This advantageous feature is possible due to the unique nature of the crosslinked, polymeric cage adjacent the liposome membrane. The dried liposome mixture can be stored until use. To use, the dried polymer-caged liposomes are rehydrated using water or another aqueous carrier or excipient, as described herein, and administered to a subject or used for in vitro diagnostics.

Active agents to be delivered to the target tissue can include virtually anything suitably sized to be contained in or retained by the supramolecular assemblies described herein, including therapeutic agents, dyes, salts, oligopeptides, proteins (e.g., enzymes, ribosome-deactivating peptides (saporin or ricin)), RNA-oligimers (e.g., microRNA or small-interfering RNA) and various DNA's (e.g., cDNA, plasmid, etc.). Therapeutic agents include drugs and other therapeutic molecules (e.g., small molecule drugs and larger molecular weight drugs (i.e., greater than about 125 Da)), biologics (e.g., recombinant nucleic acids, RNA oligomers, DNA plasmids, enzymes, proteins, etc.), radioactive isotopes (e.g., alpha-emitters: radium 223, thorium 227, actinium 225, astatine 211, bismuth212, beta emitters: phosphorous 32m yttrium 90, iodine 131, samarium 153, strontium 89, gamma emitters: technetium 99 and indum 111, x-ray emitters: iodine 125), poisons, toxins (e.g., saporin or ricin), and combinations thereof.

The term "dyes" as used herein, includes organic and inorganic dyes, as well as fluorophores and phosphophores. Self-quenching dyes are particularly preferred for use in imaging and detection. Such dyes, when provided at a suitably high concentration will form stable homocomplexes that change the absorbance profile of the dye and quench the fluorescence of the dye while in proximity to each other (e.g., such as when contained in the liposomes). Thus, the emission spectrum of the dye is only detectable once the dyes are released from the supramolecular assembly. Sufficient dye concentrations for self-quenching are dependent upon the dye, but can be determined experimentally by those skilled in the art. Exemplary concentrations for particularly preferred dyes are described herein. Suitable organic dyes are selected from the group consisting of coumarins, pyrene, cyanines, benzenes, N-methylcarbazole, erythrosin B, N-acetyl-L-tryptophanamide, 2,5-diphenyloxazole, rubrene, and N-(3-sulfopropyl)acridinium. Specific examples of preferred coumarins include 7-aminocoumarin, 7-dialkylamino coumarin, and coumarin 153. Examples of preferred benzenes include 1,4-bis(5-phenyloxazol-2-yl)benzene and 1,4-diphenylbenzene. Examples of preferred cyanines include oxacyanines, thiacyanines, indocyanins, merocyanines, and carbocyanines. Other exemplary cyanines include ECL Plus, ECF, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, CypHer5, Dye-33, Cy7, Cy7.5, Cy5.0, Cy5.5, Cy3Cy5 ET, Cy3B, Cy3.0, Cy3.5, Cy2, CBQCA, NIR1, NIR2, NIR3, NIR4, NIR820, SNIR1, SNIR2, SNIR4, Merocyanine 540, Pinacyanol-Iodide, 1,1-Diethyl-4,4-carbocyanine iodide, Stains All, Dye-1041, or Dye-304.

Suitable inorganic dyes are selected from the group consisting of metalated and non-metalated porphyrins, phthalocyanines, chlorins (e.g., chlorophyll A and B), and metalated chromophores. Preferred porphyrins are selected from the group consisting of tetra carboxy-phenyl-porphyrin (TCPP) and Zn-TCPP. Preferred metalated chromophores are selected from the group consisting of ruthenium polypyridyl complexes, osmium polypyridyl complexes, rhodium polypyridyl complexes, 3-(1-methylbenzoimidazol-2-y0-7-(diethylamino)-coumarin complexes of iridium(III), and 3-(benzothiazol-2-yl)-7-(diethylamino)-coumarin complexes with iridium(III).

Suitable fluorophores and phosphophores are selected from the group consisting of phosphorescent dyes, fluoresceines (e.g. carboxyfluorescein, calcein), rhodamines (e.g., rhodamine B, rhodamine 6G), and anthracenes (e.g., 9-cyanoanthracene, 9,10-diphenylanthracene, 1-Chloro-9,10-bis(phenyl-ethynyl)anthracene).

To prepare liposomes for imaging, the dye concentration in the liposome formation solution is preferably from about 5 to about 200 mg dye per g of lipid used to form the liposome, and more preferably from about 5 to about 100 mg dye per g of lipid used to form the liposome. For in vitro diagnostics, the dye concentration in the liposome formation solution is preferably from about 10 to about 200 mg per g of lipid used to form the liposome, and more preferably from about 50 to about 100 mg per g of lipid used to form the liposome.

It will be appreciated that multiple dyes could be used to detect various protease activity. For example, one set of supramolecular assemblies can be prepared using one dye and a selected protease consensus sequence and a second set of supramolecular assemblies can be prepared with another dye and another type of sequence, and so on. Thus, the supramolecular assemblies can be used to measure and specifically identify the activity of several different proteases simultaneously, depending upon the emission spectrum detected. It will be appreciated that for imaging and detection, some of the dyes may need to be excited using an external excitation source at the appropriate wavelength to generate emission from the dye. In such cases, all of the dyes used in the supramolecular assembly can be excited simultaneously, or the dyes can be individually excited.

Figure 3:
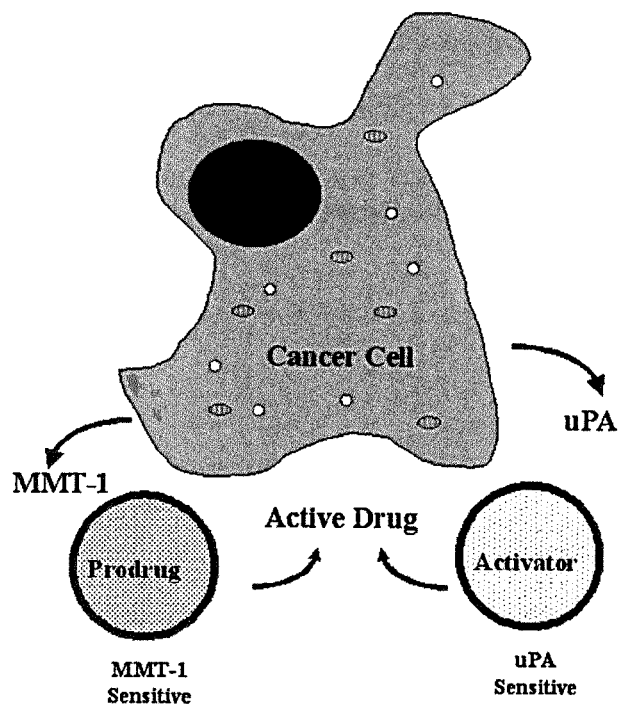
FIG. 3 is a schematic illustrating activation of a supramolecular assembly having three levels of specificity according to an embodiment of the invention.

In addition, combinations of active agents could be used. For example, one supramolecular assembly could include a prodrug and another supramolecular assembly could include an activator, providing the system with three levels of specificity to the target tissue (FIG. 3). Combinations of dyes and therapeutic agents can also be used (either in the same assembly or in different assemblies administered together).

For in vivo detection, imaging, and/or treatment, the supramolecular assemblies are administered to a subject as a diagnostic and/or therapeutic composition. Preferably, for therapeutic or theranostic applications, a therapeutically-effective amount of supramolecular assemblies is administered to a subject. As used herein, a "therapeutically effective" amount refers to the amount of the supramolecular assemblies that will elicit the biological or medical response of a tissue, system, animal, or human that is being sought by a researcher or clinician, and in particular elicit some desired therapeutic effect. For example, in one or more embodiments, a therapeutically effective amount of the supramolecular assemblies is an amount that releases sufficient active agents to damage, kill, or otherwise destroy the cancerous tissue. One of skill in the art recognizes that an amount maybe considered therapeutically effective even if the condition is not totally eradicated but improved partially. The supramolecular assemblies can be injected directly into the target tissue, or can be administered systemically. Advantageously, even when administered systemically, the supramolecular assemblies preferentially accumulate in the cancerous tissue, and preferably actively integrate in the cancerous tissue, as opposed to surrounding healthy tissue. The supramolecular assemblies can be administered using any suitable method including oral, intravenous (i.v.), intraperitoneal (i.p.), intramuscular (i.m.), intratumoral (i.t.), or intraarterial (i.a.) administration. Diagnostic and/or therapeutic compositions comprising (consisting essentially or even conssiting of) the supramolecular assemblies can thus be prepared in numerous forms.

Preferably, the supramolecular assemblies are first dispersed in a pharmaceutically-acceptable carrier or excipient before being administered to the subject. Thus, in a further aspect of the invention, there is provided a composition comprising the supramolecular assemblies dispersed or dissolved in a pharmaceutically-acceptable carrier or excipient. As used herein, the term "pharmaceutically-acceptable" means not biologically or otherwise undesirable, in that it can be administered to a subject without excessive toxicity, irritation, or allergic response, and does not cause any undesirable biological effects or interact in a deleterious manner with any of the other components of the composition in which it is contained. A pharmaceutically-acceptable carrier or excipient would naturally be selected to minimize any degradation of the supramolecular assemblies and/or active agents and to minimize any adverse side effects in the subject, as would be well known to one of skill in the art. Pharmaceutically-acceptable ingredients include those acceptable for veterinary use as well as human pharmaceutical use. Exemplary carriers and excipients include aqueous solutions such as normal (n.) saline (~0.9% NaCl), phosphate buffered saline (PBS), and/or sterile water (DAW). Solids and solid dispersions can also be used using dry carriers, such as lactose or other sugars, polysaccharides, starches, cellulosics, and the like. Hydrogels can also be used to deliver the assemblies. The compositions can be provided as solutions, capsules, tablets, and the like. For liposomes, the composition preferably comprises less than about 10% by weight liposomes, more preferably from about 1% to about 10% by weight liposomes, and more preferably from about 3% to about 5% by weight liposomes, based upon the total weight of the composition taken as 100% by weight.

In one or more embodiments, a targeting moiety can be attached to the supramolecular assembly to direct the assembly to, and cause it to accumulate in and near, the target tissue, even when administered systemically. Targeting moieties include tumor-homing peptides, as well as biotin, folic acid, or antibodies. For example, in the case of cancer, when tumor-homing peptides are used, direct injection into the cancerous tissue is not necessary. This aspect enhances the natural affinity of liposomes for cancerous tissue. The additional advantage to systemic administration of the supramolecular assemblies is that cancerous tissue that has not yet even been identified can be identified and treated. Examples of suitable tumor-homing sequences, which can be coupled using any suitable method (e.g., amide, CDI, etc.) are listed in the table below.

TABLE V

Tumor-homing peptide sequences

| Name or Acronym | Sequence | Binding site |
| --- | --- | --- |
| iRGD | CRGDKGPDC (SEQ ID NO: 48) | Tumor endothel. |
| F3 | KDEPQRRSARLSAKPAPPKPEPKPKKAPAKK (SEQ ID NO: 49) | Nucleolin, endothel., cells |
| LyP-1 | CGNKRTRGC (SEQ ID NO: 50) | Tumor lymphatic |
| TFR targeting | HAIYPRH (SEQ ID NO: 51) | Transferrin receptor (non transferring binding part) |
| KDR binder | ATWLPPR (SEQ ID NO: 52) | Angiogenic vessels |
| VEGFR binder | RRKRRR (SEQ ID NO: 53) | Angiogenic vessels |
| Glu-Oct6 | EEEAAGRKRKKRT (SEQ ID NO: 54) | Glutamate receptor e.g., psma |
| pHLIP | AEQ NPIYWARXADWL FTTPLLLLDLAALLVDADEGT, where X = 3,5 diiodotyrosine (SEQ ID NO: 55) | pH dependant |
| YALA | WEAALAEALAEALAXHLAALAEALEAL AA, where X = 3,5 diiodotyrosine (SEQ ID NO: 56) | pH sensitive; delivers across cell at pH 6.7 |
| CD133 binding | APSPMIW (SEQ ID NO: 57) | |
| CD133 binding | LQNAPRS (SEQ ID NO: 58) | |
| CLT1 | CGLIIQKNEC (SEQ ID NO: 59) | Clots in tumors |
| CLT2 | CNAGESSKNC (SEQ ID NO: 60) | Clots in tumors |
| | CREKA (SEQ ID NO: 61) | Fibrin clots |
| | CGKRK (SEQ ID NO: 62) | Heparan sulfate |
| | CGSLVRC (SEQ ID NO: 63) | Tumor vasc. |
| | CPGPEGAGC (SEQ ID NO: 64) | Tumor vasc. |
| | CDTRL (SEQ ID NO: 65) | Tumor vasc. |
| | RRPYIL (SEQ ID NO: 66) | Neurotensin receptor |
| | EDYELMDLLAYL (SEQ ID NO: 67) | |
| | ATWLPPR (SEQ ID NO: 68) | VEGF receptor; Tumor vasc. |
| | CGGKLKSQLVKRK (SEQ ID NO: 69) | HA |
| | CGGKNGRYSISR (SEQ ID NO: 70) | HA |
| | CGGRDGTRYVQKGEYR (SEQ ID NO: 71) | HA |
| | CGGAHWQFNALTVR (SEQ ID NO: 72) | HA |
| TAT | GRKKRRQRRRPQC (SEQ ID NO: 73) | |

Tumor-homing peptides can also be attached to the active agents to be delivered to the target tissue. This ensures that the active agents, once released from the supramolecular assembly, will not be carried away from the target tissue, but will remain and be taken up by the tissue (if they haven't already). It will be appreciated that other types of targeting moieties with affinities for tissues other than cancer can also be used to direct the supramolecular assemblies to those target tissues.

Figure 4:
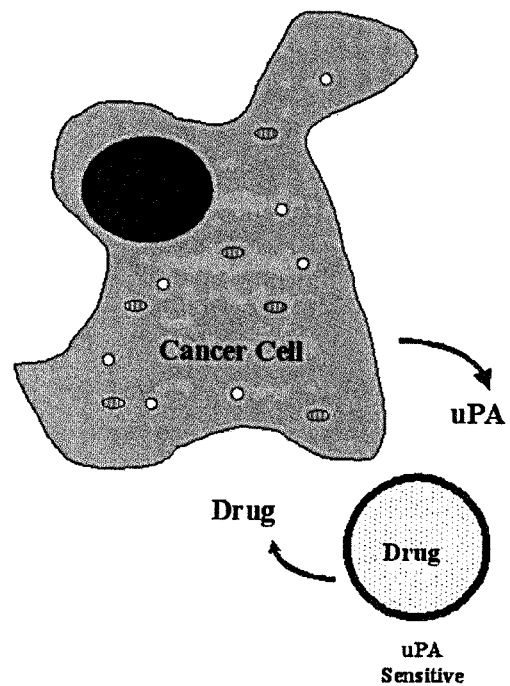
FIG. 4 is a schematic illustrating activation of a supramolecular assembly according to one embodiment of the invention by uPA to release the active agent (drug) from inside the liposome.
Figure 5:
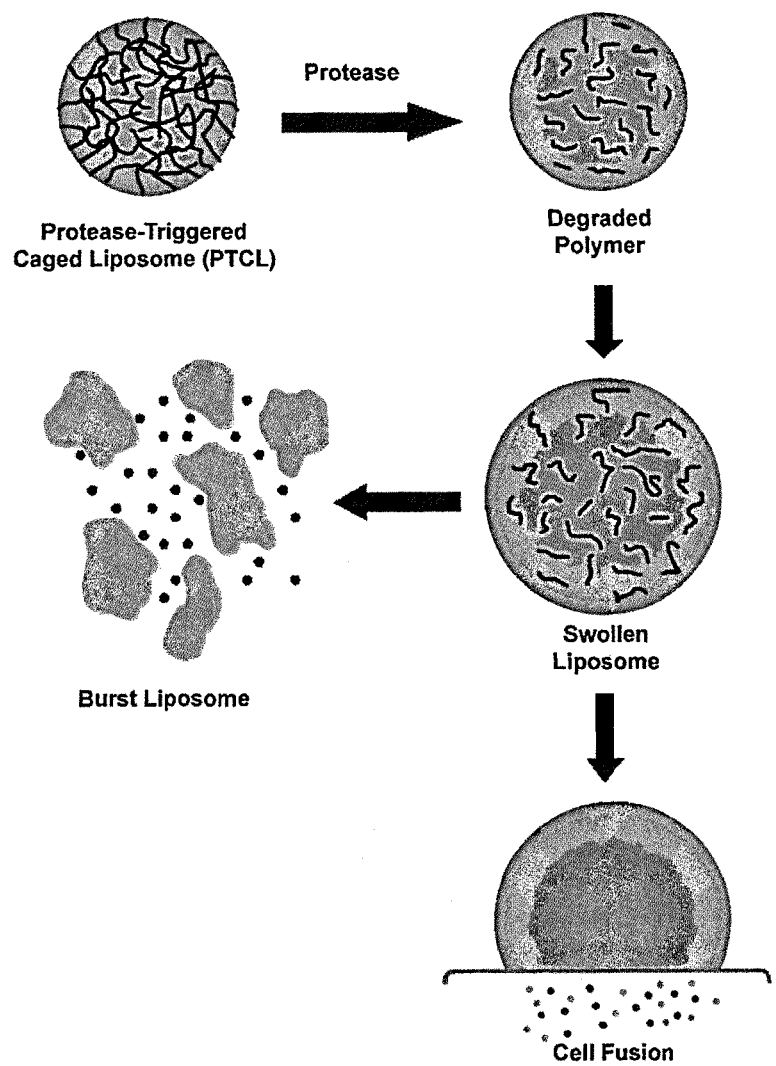
FIG. 5 is a schematic illustrating the mechanism of release of the liposome contents according to various embodiments of the invention.

Once the supramolecular assembly is in the vicinity of the cancerous tissue, the cancer-associated proteases will degrade the peptide linkages in the assembly and "activate" the assembly, as illustrated in FIG. 4. For example, in the case of liposomes, the crosslinked, polymeric coating will be degraded causing the liposomes to swell and burst to release their contents and/or fuse with the target cells to release their contents directly into the cell. This general process is depicted in FIG. 5. It will be appreciated that methods of detecting protease activity will depend upon the particular mechanism of the entrapped active agent selected for use in the invention. For example, in one or more embodiments, detection and imaging of cancerous tissue can be accomplished by detecting the emission spectrum of previously-entrapped dyes using conventional equipment. In some cases, excitation can be directed to the region of interest using an energy source selected from the group consisting of a polychromatic light source, laser, and laser diode to excite the dyes and permit their detection. In other embodiments, a change in the conductance of the tissue due to the release of the hypertonic liposomal interior can be detected with electrodes.

Regardless of the embodiment, the detected protease activity can be used to diagnose cancer stages. For example, if urokinase activity is found by the supramolecular assay, then a supramolecular assembly employing a consensus sequence for matrilysin (MMP-7) can be administered. If matrilysin activity is detected, the prognosis is for angiogenesis or metastasis. For confirmation, a supramolecular assembly comprising a consensus sequence for collagenase (MMP-1) can then be administered. If the assay is negative, the prognosis is for angiogenesis. If the assay is positive, the prognosis is for metastasis. The identified tissue can then either be excised or treated.

For in vitro detection, the supramolecular assemblies may be used to detect protease activity in a sample comprising a biological fluid, such as urine or blood of a subject. In one aspect, the biological sample is collected from the subject and physically mixed with the supramolecular assay. The protease in the sample cleaves the peptide linkages activating the supramolecular assembly, as described above. For example, the emission spectrum of self-quenched dyes can be detected once the dyes are released from the assembly. Likewise, the change in conductance in the sample due to the release of the hypertonic interior of liposome assemblies can be detected via electrodes.

Figure 6:
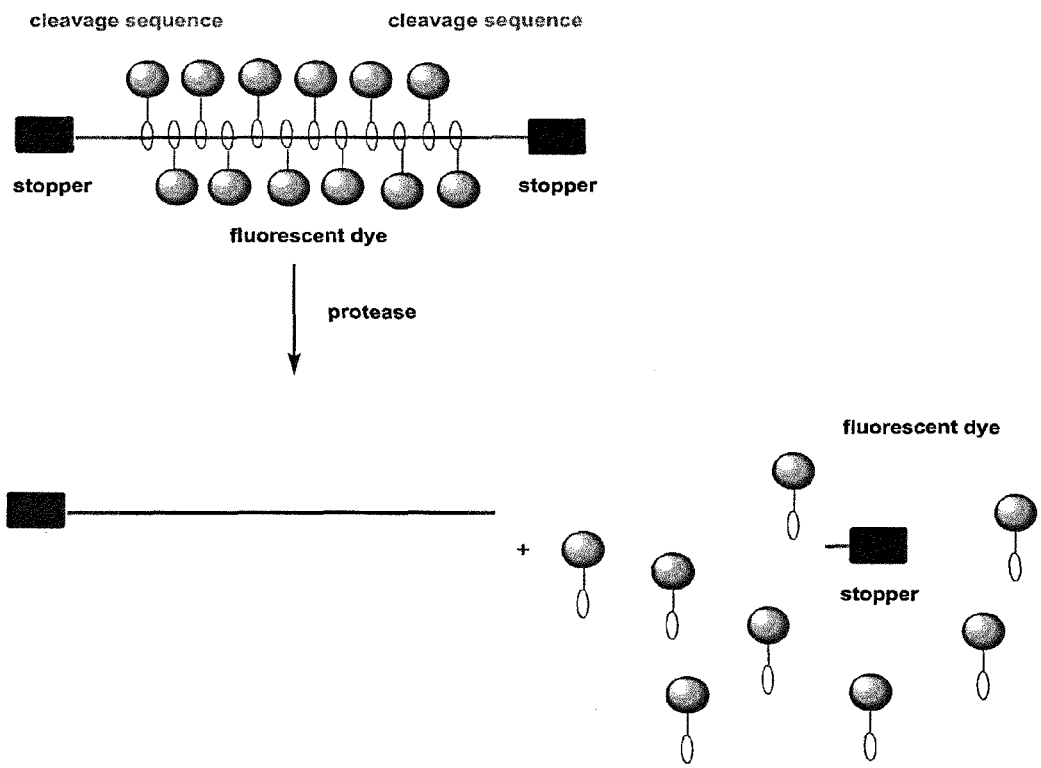
FIG. 6 is a schematic illustrating an embodiment of the invention utilizing a rotaxane supramolecular assembly.

Although the invention is described primarily with respect to liposomes, other supramolecular assemblies for use in the invention include cathenanes and rotaxanes. For example, cathenanes are mechanically-interlocked structures, generally comprising two or more interlocked macrocycles (similar to a chain-link). Based upon this architecture, two or more dyes can be linked together, with a peptide linkage (comprising a protease consensus sequence) forming part of the linkage. Due to the proximity of the dyes, their fluorescence is quenched. When degraded by the enzyme, the linkage is broken releasing or unlinking the dyes from each other at which point the emission spectrum of the dyes can be detected. Additional molecules could form part of the cathenane structure, including any of the active agents described herein. Rotaxanes are also mechanically-interlocked structures, generally comprising a dumbbell-shaped molecule threaded through one or more macrocyles with "stoppers" at each end. These stoppers are larger than the interior diameter of the macrocycle, thus preventing dissociation of the two physically-interlocked molecules. Based upon this architecture, dyes can be attached to the macrocycles and a peptide linkage (comprising a protease consensus sequence) can form part of the dumbbell-shaped molecule. When the enzyme cleaves the consensus sequence, the stopper is broken off and the macrocycles can be unthreaded or released. The emission spectrum of the previously self-quenched dyes can then be detected once they are released. This process is depicted in FIG. 6.

It will be appreciated by those skilled in the art upon review of the present disclosure that the supramolecular assays can be modified for use with diseases or conditions other than cancer, and specifically any other disease having specifically-associated proteases or otherwise associated with protease activity (i.e., disease-associated proteolytic activities), such as Alzheimer's disease and HIV. For example, HIV protease is a retroviral aspartyl protease that is essential for the lifecycle of HIV, and has a cleavage sequence of ARVL-AEAM (SEQ ID NO:82)

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

The invention described herein is discussed primarily with respect human-based therapies; however, it will be appreciated that the treatment can be applied for clinical research or therapeutic treatment to any suitable animal, including, without limitation, dogs, cats, and other pets, as well as, rodents, primates, horses, cattle, etc. Additional advantages of the invention will be apparent to those in the art upon review of the disclosure herein and the working examples below.

EXAMPLES

The following examples set forth methods in accordance with the invention. It is to be understood, however, that these examples are provided by way of illustration and nothing therein should be taken as a limitation upon the overall scope of the invention.

Example 1

Materials and Methods

1. Materials

All lipids obtained for liposome synthesis were of greater than 99% purity. 1,2-dipalmitoyl-sn-glycero-3-phosphocholine (DOPC) was purchased from Avanti Polar Lipids, Inc. (Alabaster, Ala.). 1,2-dioleoyl-sn-glycero-3-phosphocholine (DPPC) was purchased from Sigma Life Science. Cholesterol was purchased from Pfaltz and Bauer (Waterbury, Conn.). Lipids were dissolved in chloroform upon receipt and stored at $-20°$ C. to prevent degradation or absorption of water.

10× HEPES buffered saline (10× HBS) was prepared as 0.012M 4-(2-hydroxyethyl)-1-piperazineethanesulfonic acid (HEPES), 1.36M sodium chloride, and 0.045M potassium chloride. HEPES (4-(2-hydroxyethyl)-1-piperazineethane-sulfonic acid, >99.5% purity) was purchased from Sigma Life Science. Sodium chloride and potassium chloride (>99% purity) were purchased from Fisher Scientific. 5(6)-carboxy-fluorescein (CF, >99% pure) was purchased from Sigma Life Science and was stored at $-20°$ C. upon receipt.

All peptides were purchased from GenScript (Piscataway, N.J.). 3-(ethyliminomethyleneamino)-N,N-dimethyl-propan-1-amine hydrochloride (EDC.HCl) was purchased from Sigma Life Science. 3-(ethyliminomethylene-amino)-N,N-dimethyl-propan-1-amine methyliodide (EDC.MeI) was purchased from MP Biomedicals (Solon, Ohio). Hydroxybenzotriazole (HOBt) was purchased from Fisher Scientific. Both peptides and all coupling reagents were stored at 4° C. upon receipt. Sodium polyacrylate (average mass 5100 Da) was purchased from Aldrich.

2. Analysis Methods a. Liposome Concentration

Liposome concentration was assayed by determining the phospholipid concentration of the suspension using the Stewart Assay, adapted from Lasch, et. al. (In *Liposomes: A Prac-*

Figure 7:
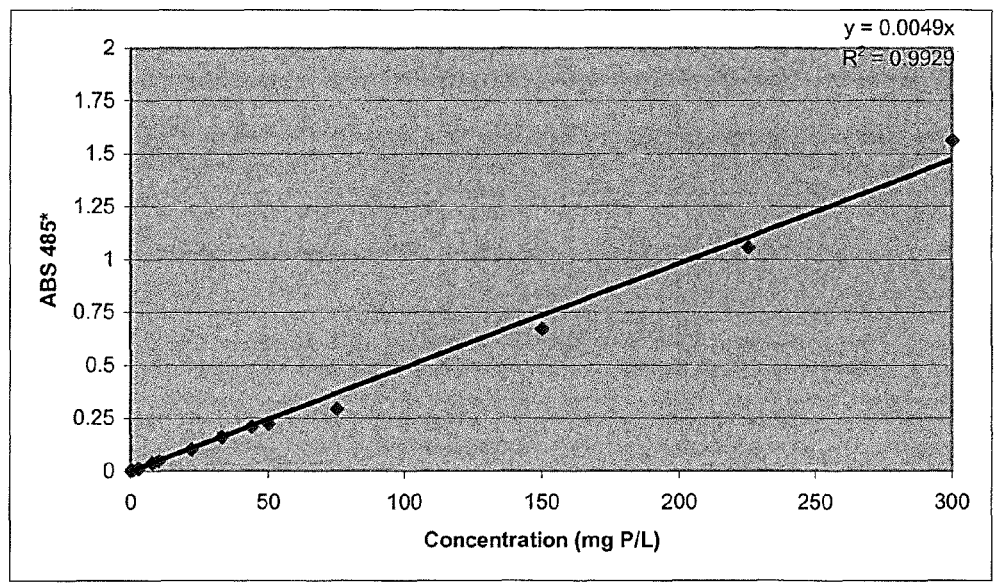
FIG. 7 is a graph of the Stewart Assay Standards from Example 1.

*tical Approach*, pp. 3-30 (2003)). Standards were prepared with 0, 2.5, 5, 7.5, 10, 11, 22, 33, 44, 50, 75, 150, 225, and 300 mg Phosphorous/L with DPPC in 1× HBS. Iron (III) thiocyanate ion was prepared from 27.03 g (0.1 mol) $FeCl_3$ and 30.4 g (0.045 mol) $NH_4SCN$ and diluted to 1 L in water to give 0.1 M $Fe(SCN)(H_2O)_5^{2+}$. Samples were prepared by adding 100 µL of liposomes prepared below, or Standard to 2 mL of the $Fe(SCN)(H_2O)_5^{2+}$ solution and 2 mL of chloroform. The mixtures were then vortexed vigorously for 1 minute and centrifuged at 2000 RPM for 10 minutes to separate the organic and aqueous layers. The lower organic layer was then removed and 725 µL of the organic layer was diluted to 1.45 mL with chloroform. The absorbance at 480 nm and 690 nm was taken. Absorbance of the $Fe(SCN)(H_2O)_5^{2+}$ complex was taken at 480 nm and to construct a better curve, the absorbance was corrected by subtracting out background absorbance of the sample as measured at 690 nm. The value $ABS_{480}-ABS_{690}$ was plotted against the standard curve to determine phospholipid concentration. The curve of $ABS_{480}$-$ABS_{690}$ versus concentration was linear over the entire concentration range (FIG. 7).

b. Liposome Sizing

Once the liposome concentration was found, liposomes were diluted to 1 mg P/L in isotonic buffer. The liposome suspension was allowed to stabilize to room temperature and dynamic light scattering (DLS) measurements were taken with a Brookhaven ZetaPlus Particle Size Analyzer.

c. Carboxyfluorescein Concentration

A percent encapsulation procedure was adapted from Lasch et. al. In order to determine percent encapsulation, 100 µL of the liposome suspension was added to 100 µL of 5M Brij-58. The solutions were mixed well and then diluted to 2 mL. Serial dilutions were made until the absorbance at 480 nm was less than one. The absorbance at 480 nm and 690 nm were then measured. The concentration of carboxyfluorescein was determined by the $ABS_{480}$-$ABS_{690}$ as compared to a standard curve.

d Carboxyfluorescein Release Assay i. Pressure Sensitive Carboxyfluorescein Release Liposomes were prepared as described below in 10× HBS. Various dilutions of HBS were then made by diluting 10× HBS with 0.012 M HEPES Buffer to make the solutions have the desired pressures against 10× HBS. The desired samples were then diluted so that the sample contained 2 µmol carboxyfluorescein in 2 mL for each sample. The diluted samples were incubated at 37.5° C. for the desired time and then fluorescence measurements were taken to determine percent release. Carboxyfluorescein was excited at 450 nm and the fluorescence was recorded from 470 nm to 620 nm. Total fluorescence was determined by summing the fluorescence from 470 nm to 620 nm. Curves of total fluorescence verses pressure were fitted using a logistic function:

$$F(\Pi) = \frac{A}{B + Ce^{-D\Pi+E}}$$

where $\Pi$ is the difference in osmotic pressure and A, B, C, D, and E are fitting constants. The fluorescence verses pressure curves were then compared to determine the difference in pressure sensitivity of various liposome preparations.

ii. Urokinase Sensitive Carboxyfluorescein Release

Using the results from the pressure sensitivity studies, the ideal osmotic pressure was determined for various liposome preparations. Liposomes were prepared as below in a concentration of HBS that would give the ideal osmotic pressure for that preparation versus 1× HBS ($\Pi_{n\times\ HBS}-\Pi_{1\times\ HBS}$=ideal osmotic pressure or $\Pi_{1\times\ HBS}$+ideal osmotic pressure= $\Pi_{n\times\ HBS}$). These liposome preparations were then diluted into HBS with various amounts of uPA so that the final concentration of HBS was 1× and the final content of carboxyfluorescein was 2 µmol in 2 mL. The diluted samples were incubated at 37.5° C. for the desired time and then fluorescence measurements were taken to determine percent release. Carboxyfluorescein was excited at 450 nm and the fluorescence was recorded from 470 nm to 620 nm. Total fluorescence was determined by summing the fluorescence from 470 nm to 620 nm.

Example 2

Synthesis of Cholesterol-Tagged, Protease-Sensitive Polyacrylic Acid

1. Acid Functionalized Cholesterol 1.15 g of cholesterol (3 mmol, 1 eq.) were dissolved in 30 mL of THF along with 0.72 g NaH (30 mmol, 10 eq.), and the reaction was stirred one hour. At the end of one hour, 10 mL of diethyl ether were added and the reaction was stirred for 1.5 hours. After stirring, 1.76 g of tertiary butyl 2-bromoacetate (9 mmol, 3 eq.) were added to the solution, and the solution was refluxed for 15 hours. After refluxing, 20 mL of water were added and the product was extracted with 3×25 mL diethyl ether. After extracting, the ether was evaporated off, and the sample was dissolved in 10:1 hexane:ethylacetate (vol/vol) and run over a 0.5 in.×15 in. silica gel column. The product eluted after 40 mL. NMR was taken to confirm product.

To deprotect the acid group, 3 mL of formic acid (79.5 mmol, 26.5 eq.) were added to the product isolated above with 7 mL of diethyl ether. The solution was refluxed for 2 hours and then the diethyl ether and formic acid were evaporated. NMR was taken to confirm product.

2. Amine Functionalized Polyacrylic Acid 5 g of sodium polyacrylate (5100 Da average weight, 1 equivalent) and 0.38 mL 2-(2-chloroethyl)oxirane (5 eq.) were dissolved in 20 mL of dry DMF. The mixture was stirred for 72 hours at room temperature and then 1 mL of 18M $NH_4OH$ (18 eq.) was added dropwise to the mixture. The solution was then stirred another 24 hours at room temperature and then rotovapped to dryness. Once dry, the powder was put under high vacuum for 72 hours to remove any remaining solvent. The resulting white powder was stored under nitrogen.

3. Condensation 2.5 mg (1 eq.) of the acid-derivatized cholesterol were dissolved in 500 µL it dry DMF and cooled to 0° C. Next, 1.7 mg (1 eq.) of EDC.HCl was added, and the solution was stirred at 0° C. for 30 minutes. 1 mg (1.33 eq.) of HOBt was then added, and the solution was stirred at room temperature for three hours. 4 mg (1 eq.) of the peptide GSGRSAGC (SEQ ID NO: 20; synthetic, >80% pure) were added to the mixture, and the solution was stirred overnight to give the cholesterol-peptide complex (not purified).

Figure 8:
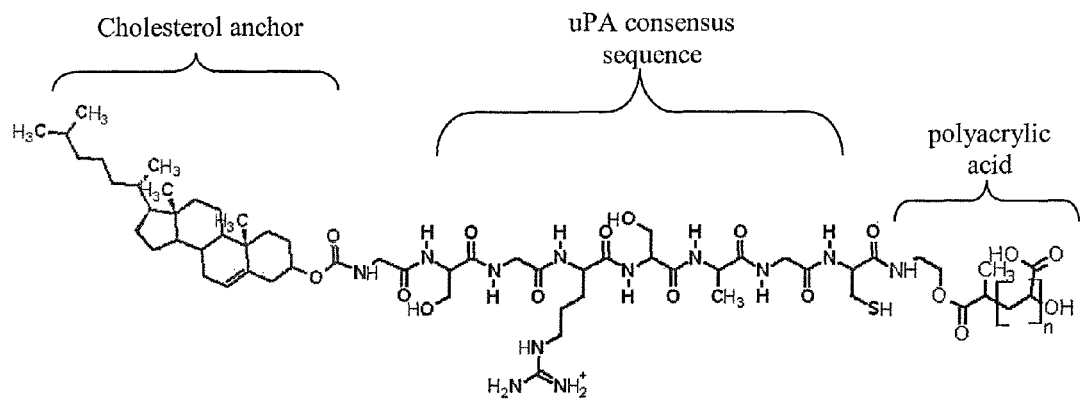
FIG. 8 shows the structure of polymer for the crosslinked, polymeric cage synthesized in Example 2.

After 24 hours, the mixture was again cooled to 0° C. 1.7 mg (1 eq.) of EDC.HCl were added, and the solution was stirred at 0° C. for 30 minutes. 1 mg (1.33 eq.) of HOBt was then added, and the solution was stirred at room temperature for three hours. Next, 29 mg (1 eq.) amine functionalized polyacrylic acid were added to the mixture, and the mixture was stirred overnight. The mixture was then rotovapped to dryness and the resulting powder was put under high vacuum for 72 hours to remove any solvent remaining. The synthesized block copolymer is shown in FIG. 8.

Example 3

Liposome Preparation

1. Bare Liposomes

For the general method of preparing the bare liposomes (BLs), DPPC, or DPPC and DOPC (various ratios) were dissolved in chloroform along with cholesterol (various ratios). The solution was vortexed for 30 seconds to insure even distribution of the lipids. The chloroform was then evaporated off at 50° C. under blowing air. Once the lipid film was dry, it was placed under high vacuum for 1 hour to remove any remain chloroform.

After drying, the lipid film was hydrated with PBS or n× HBS (prepared by diluting 10× HBS) with or without 100 mM carboxyfluorescein. The hydrated film was vortexed for 3 minutes, sonicated for 1 minute, and then vortexed again for two minutes to suspend the lipid film in the HBS. The suspension was then put through ten freeze-thaw cycles, 8 minutes/cycle (4 cold/4 hot) with the high temperature being 50° C. and the low temperature being −80° C.

After the last freeze-thaw cycle, the suspension was warmed to 50° C. The suspension was then forced through two polycarbonate membranes with 200 nm pores using an Eastern Scientific, Inc. mechanical extruder. After passing through the membranes ten times, the liposome preparation was purified from the unentrapped analytes by passing through a 15 cm×1 cm Sephadex G-50 gel filtration column. The cloudy fraction that came out with the void volume was collected. Liposome preparation was verified by dynamic light scattering of the resulting suspension. The suspension was stored at 4° C. until use.

BLs were initially prepared with 5.2 mg DPPC (55.4 mol %) and 2.1 mg Cholesterol (44.6 mol %). The lipids were dissolved in 300 µL chloroform and dried under argon at 50° C. The lipids were then hydrated in 300 µL of 1× PBS (1× Phosphate Buffered Saline, 0.136 M NaCl, 0.0045 M KCl, 0.012 M $PO_4^{3-}$ buffered to pH 7.4). The liposomes were then diluted to 10% of the concentration post-preparation in 1× PBS and dynamic light scattering measurements were taken to verify liposome preparation. Four separate samples were measured with a mean diameter of 136.72 nm and a standard deviation of 0.82 nm (0.60%) indicating that liposomes were successfully prepared by this method. The very low standard deviation across samples indicated that the liposomes were very monodisperse.

TABLE

Dynamic Light Scattering Results: Bare Liposome Synthesis

|   | Correlation Time (ms) | Diameter (nm) |
|---|---|---|
| 1 | 0.8023 | 137.73 |
| 2 | 0.79227 | 136.01 |
| 3 | 0.79839 | 137.06 |
| 4 | 0.79275 | 136.09 |
| Mean | 0.79642 | 136.72 |
| St. Dev. | 0.00480 | 0.82 |
| % St. Dev. | 0.60% | 0.60% |

2. Polymer Incorporated Liposomes

The general method for preparing polymer incorporated liposomes (PILs) follows. Protease sensitive polyacrylic acid from Example 1 (various amounts) was added to BLs that were synthesized in n× HBS with or without 100 mM carboxyfluorescein. The mixture was heated to 37.5° C. and rocked overnight. The PILs were then separated from unincorporated polymer by passing over a 15 cm×1 cm Sephadex G-50 gel filtration column. The cloudy fraction that comes out with the void volume was collected. PILs preparation were verified by dynamic light scattering (DLS), as discussed in more detail below. The suspensions were stored at 4° C. until needed.

PILs were initially prepared by adding BLs (constituting 2 µmol of DPPC (1 eq.)) to 20 µL of the block copolymer at 0.2 mg/µL (4 mg, 0.32 eq.), and diluting to 600 µL with 10× HBS. A control batch was also made by adding BLs to 20 µL 10× HBS and diluting to 600 µL with 10× HBS. Three preparations of the sample and the control were made. The mixtures were heated to 37.5° C. and rocked overnight. The PILs were then purified and collected, and then stored in suspension until use.

After taking concentration measurements, the preparations were diluted to 1 mg phosphorous/L and DLS measurements were taken. Each sample was sampled four times for DLS measurement to confirm that the polymer integrating into the liposome increased the hydrodynamic diameter because due to added size and drag to the liposome.

TABLE

Polymer Incorporated Liposome DLS Measurements.

| Sample | Measurement 1 | 2 | 3 | 4 | Mean | St Dev | % St Dev |
|---|---|---|---|---|---|---|---|
| Control 1 | 112.55 | 111.76 | 113.38 | 117.30 | 113.75 | 2.46 | 2.16% |
| Control 2 | 114.06 | 114.37 | 108.70 | 114.42 | 112.89 | 2.80 | 2.48% |
| Control 3 | 107.32 | 113.34 | 113.17 | 110.48 | 111.08 | 2.83 | 2.54% |
| Sample 1 | 116.03 | 118.80 | 115.48 | 115.73 | 116.51 | 1.54 | 1.32% |
| Sample 2 | 116.03 | 110.92 | 113.83 | 121.69 | 115.62 | 4.56 | 3.94% |
| Sample 3 | 113.25 | 113.38 | 111.46 | 116.56 | 113.66 | 2.12 | 1.87% |

TABLE

PIL DLS Summary

| Sample | Mean | St Dev | % St Dev |
|---|---|---|---|
| PIL Control | 112.57 | 2.70 | 2.40% |
| PIL Sample | 115.26 | 3.01 | 2.61% |

Figure 9:
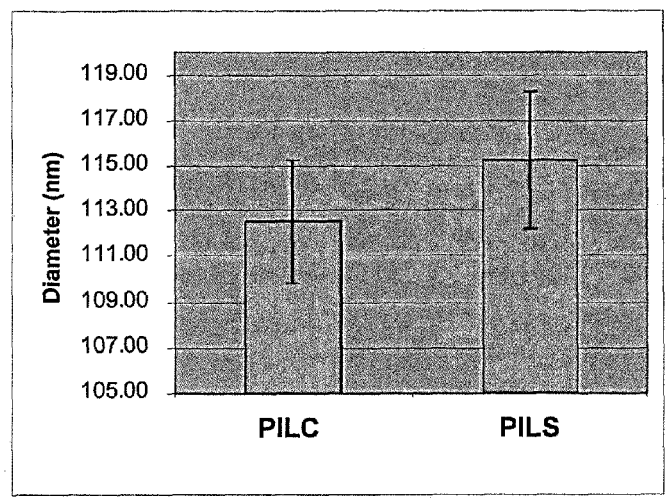
FIG. 9 shows the results of the DLS measurements for the control (C) and sample (S) PILs from Example 3.

As can be seen in FIG. 9, the sample containing the polymer did register slightly larger than the control (p=0.03), indicating that polymer was successfully integrated into the liposome membrane.

3. Polymer Caged Liposomes

A general method for preparing the polymer caged liposomes (PCLs), was as follows. PILs were heated to 37.5° C. One equivalent (eq.) of EDC.MeI (in relation to the polyacrylic acid residues, assuming 100% incorporation) was added to the suspension and the suspension was rocked for two hours at 37.5° C. The crosslinker was then added to the suspension (various ratios to polyacrylic acid residues), and the suspension was rocked at 37.5° C. overnight. The PCLs were separated from reagents by passing over a 15 cm×1 cm Sephadex G-50 gel filtration column. The cloudy fraction that came out with the void volume was collected. PCL preparation was verified by DLS, as described in more detail below. The suspension was stored at 4° C. until needed.

a. PCLs with Consensus Sequence Crosslinkers

PCLs were initially prepared using a short peptide sequence, GSGRSAKG (SEQ ID NO: 21; synthetic, >80% pure), that contained two amines (the N-terminal amine and the lysine amine) and the uPA consensus sequence between them (GSGRSAGC, SEQ ID NO: 20) as the crosslinker. This was used so that uPA would be able to cleave both the polymer and the crosslinks to more fully degrade the polymer cage. PILs constituting 640 nmol DPPC (1 eq.) were added to 5.8 mg EDC.MeI (19.5 µmol, 30 eq.), and then incubated 2 hours at 37.5° C. Next, 20 uL of the peptide crosslinker at 40 mg/mL (36 nmol, 0.056 eq., 34% crosslinking assuming 100% reaction) were added, and the preparation was rocked at 37.5° C. overnight. A control batch was also made by adding PILs constituting 640 nmol DPPC (1 eq.) to 5.8 mg EDC.MeI (19.5 µmol, 30 eq.) and incubating 2 at 37.5° C. After incubating, 20 uL of 1× HBS were added, and the preparation was incubated overnight at 37.5° C. Three preparations of the sample and the control were made. The resulting PCLs were separated from reagents, collected, and stored as described above.

After taking concentration measurements, the preparations were diluted to 1 mg phosphorous/L and DLS measurements were taken. Each sample was sampled four times for DLS measurements to confirm that crosslinking increased the hydrodynamic radius of the liposomes because it increases the rigidity of the polymer cage, increasing both size and drag.

Figure 10:
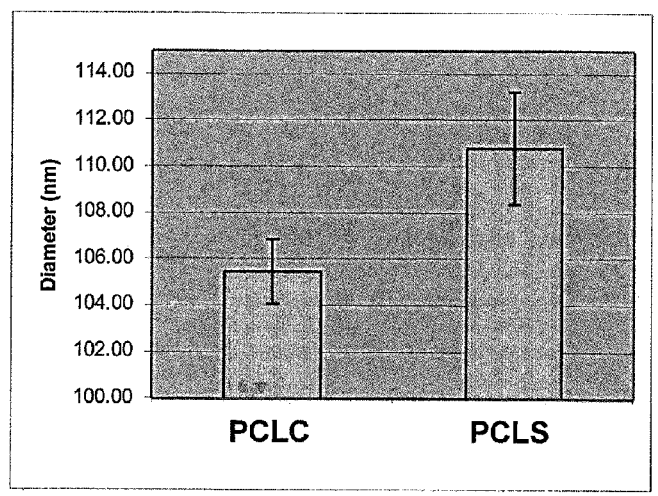
FIG. 10 shows the results of the DLS measurements for the control (C) and sample (S) PCLs from Example 3.

As can be seen in FIG. 10, the crosslinking did register substantially larger than the control (p<0.0001), indicating that the PCLs were successfully prepared.

b. PCLs With Ethylenediamine Crosslinkers

To increase the resistance of the PCLs to osmotic pressure PCLs were also synthesized using ethylenediamine instead of the short peptide sequence as the crosslinker. BLs were synthesized as above using 27.5 mg DPPC (37.5 µmol, 47.5 mol %), 3.1 mg DOPC (3.9 µmol, 5.0 mol %), and 14.5 mg cholesterol (37.5 µmol, 47.5 mol %) hydrated in 10× HBS with 100 mM carboxyfluorescein. BLs constituting (4 µmol DPPC+DOPC (1 eq.)) were added to either 25 nmol (0.006 eq., average 9 nm between polymers), 53 nmol (0.013 eq., average 6 nm between polymers), or 212 nmol (0.053 eq., average 3 nm between polymers) of the synthesized polymer and diluted to 600 µL. These were designated low (L), medium (M), or high (H) samples, respectively.

After incubating overnight to prepare the PILs, EDC.MeI and ethylenediamine were added without a purification step (one-pot procedure) in order to increase yield. To the low sample, either 146 nmol (0.036 eq., 50% crosslinking), 219 nmol (0.055 eq., 75% crosslinking), or 292 nmol (0.073 eq., 100% crosslinking) of ethylenediamine were added along with EDC.MeI at 1500:1 EDC:ethylenediamine. These were designated L50, L75, and L100, respectively. To the medium sample, either 313 nmol (0.078 eq., 50% crosslinking), 470 nmol (0.117 eq., 75% crosslinking), or 626 nmol (0.157 eq., 100% crosslinking) of ethylenediamine were added along with with EDC.MeI at 1500:1 EDC:ethylenediamine. These were designated M50, M75, and M100 respectively. To the high sample, either 1,250 nmol (0.313 eq., 50% crosslinking), 1,880 nmol (0.470 eq., 75% crosslinking), or 2,500 nmol (0.626 eq., 100% crosslinking) of ethylenediamine were added along with with EDC.MeI at 1500:1 EDC:ethylenediamine. These were designated H50, H75, and H100, respectively.

Figure 11:
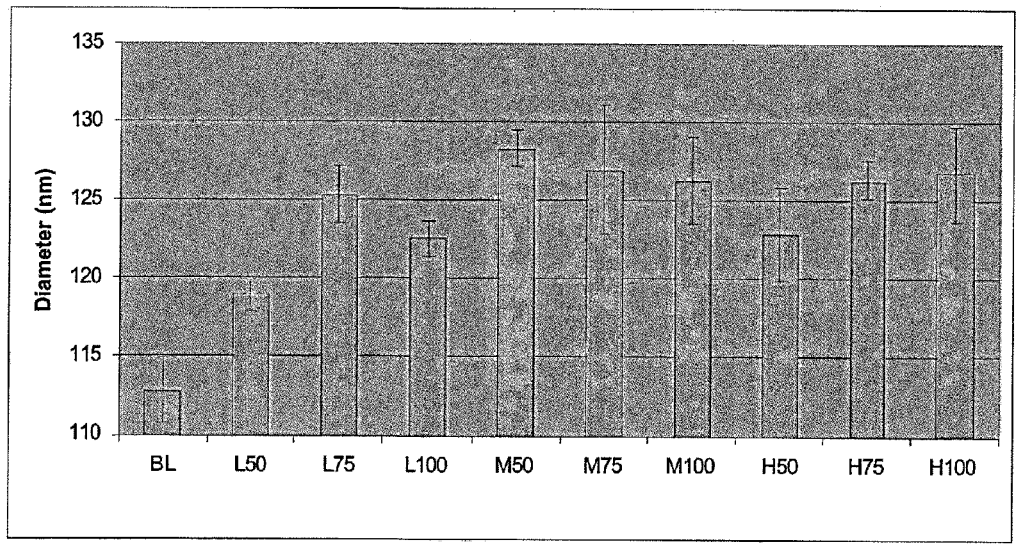
FIG. 11 shows the results of the DLS measurements for the PCLs synthesized using ethylenediamine crosslinked PCLs from Example 3.

As can be seen in FIG. 11, each of the PCLs showed an increase in average diameter verses the control (BLs). The values ranged from a minimum of +6.1 nm for L50, to +15.5 nm for M50. P values were calculated for each sample verses the control and the values can be seen in table 2.4.7. All P values were less than 0.01, indicating that the PCLs were successfully prepared.

TABLE

Polymer Caged Liposome DLS Measurements

| Sample | Measurement 1 | 2 | 3 | 4 | Mean | St Dev | % St Dev |
|---|---|---|---|---|---|---|---|
| Control 1 | 104.15 | 103.13 | 104.77 | 105.03 | 104.27 | 0.84 | 0.81% |
| Control 2 | 104.98 | 107.08 | 106.05 | 107.20 | 106.33 | 1.04 | 0.97% |
| Control 3 | 107.44 | 105.99 | 106.09 | 103.77 | 105.82 | 1.52 | 1.44% |
| Sample 1 | 112.16 | 110.67 | 113.24 | 114.06 | 112.53 | 1.47 | 1.30% |
| Sample 2 | 113.85 | 107.53 | 107.18 | 111.42 | 110.00 | 3.21 | 2.92% |
| Sample 3 | 107.87 | 109.26 | 110.65 | 111.77 | 109.89 | 1.69 | 1.54% |

TABLE

PCL DLS Summary

| Sample | Mean | St Dev | % St Dev |
|---|---|---|---|
| PCL C | 105.47 | 1.40 | 1.33% |
| PCL S | 110.81 | 2.41 | 2.17% |

TABLE

Ethylenediamine Crosslinked PCL DLS Measurements

| | Mean | St Dev | P value vs BL |
|---|---|---|---|
| BL | 112.8 | 2.1 | — |
| L50 | 118.9 | 1 | 0.0063 |
| L75 | 125.3 | 1.8 | 0.0001 |

TABLE-continued

Ethylenediamine Crosslinked
PCL DLS Measurements

|  | Mean | St Dev | P value vs BL |
|---|---|---|---|
| L100 | 122.6 | 1.1 | 0.0004 |
| M50 | 128.3 | 1.1 | <0.0001 |
| M75 | 126.9 | 4.1 | 0.0036 |
| M100 | 126.3 | 2.7 | 0.0002 |
| H50 | 122.9 | 3 | 0.0027 |
| H75 | 126.3 | 1.2 | 0.0001 |
| H100 | 126.7 | 3 | 0.0006 |

Each sample was compared to other samples in its set (sets being all the L samples, M samples, or H samples, and then also all the 50 samples, all the 75 samples and all the 100 samples) and p values were calculated using two sample t-tests. The p values can be seen in the Table below. With low amounts of integrated polymer (average 9 nm between polymers), adding more crosslinker made a significant difference in the size (although the 75% crosslinking was on the verge of not being significantly different from the 100% crosslinking). With medium and high amounts of integrated polymer (average 6 nm and 3 nm respectively), adding different amounts of crosslinker made no significant difference in size. This would indicate that at low polymer integration levels, the polymer probably has high mobility along the chain and can lay flat against the liposome reducing added size and drag. Therefore, adding rigidity through crosslinking makes a significant difference in the measured size of the liposomes, up to the point where the system is 100% crosslinked. For medium-to-high polymer integration levels, because of the close packing, the polymer probably has less mobility along the chain and cannot lay flat against the liposome. Therefore, adding rigidity through crosslinking makes little difference to the measured size of the liposomes.

No significant trends were seen across the 50, 75, or 100% crosslinking groups. This may indicate that the amount of crosslinking is a larger factor in the measured size of liposomes than the amount of integrated polymer. The polymer has a certain length fully stretched and the liposomes have a certain radius. At concentrations where the integrated polymer extends all the way around the liposome, the new radius should be the initial radius plus the length of the polymer. How rigid the polymer is going to be the main factor in how large the measured diameter is, so crosslinking amount ends up being more important than polymer density.

TABLE

T-test P Values within Each Subgroup

|  | L50 | L75 | L100 |
|---|---|---|---|
| L50 | * | 0.0016 | 0.0025 |
| L75 | 0.0016 | * | 0.0507 |
| L100 | 0.0025 | 0.0507 | * |

|  | M50 | M75 | M100 |
|---|---|---|---|
| M50 | * | 0.5566 | 0.2420 |
| M75 | 0.5566 | * | 0.8166 |
| M100 | 0.2420 | 0.8166 | * |

|  | H50 | H75 | H100 |
|---|---|---|---|
| H50 | * | 0.1031 | 0.1234 |
| H75 | 0.1031 | * | 0.8166 |
| H100 | 0.1234 | 0.8166 | * |

TABLE-continued

T-test P Values within Each Subgroup

|  | L50 | M50 | H50 |
|---|---|---|---|
| L50 | * | <0.0001 | 0.0647 |
| M50 | <0.0001 | * | 0.0278 |
| H50 | 0.0647 | 0.0278 | * |

|  | L75 | M75 | H75 |
|---|---|---|---|
| L75 | * | 0.5143 | 0.3977 |
| M75 | 0.5143 | * | 0.7927 |
| H75 | 0.3977 | 0.7927 | * |

|  | L100 | M100 | H100 |
|---|---|---|---|
| L100 | * | 0.0641 | 0.0622 |
| M100 | 0.0641 | * | 0.8494 |
| H100 | 0.0622 | 0.8494 | * |

Example 4

Osmotic Pressure Resistance

1. Initial Tests

Figure 12:
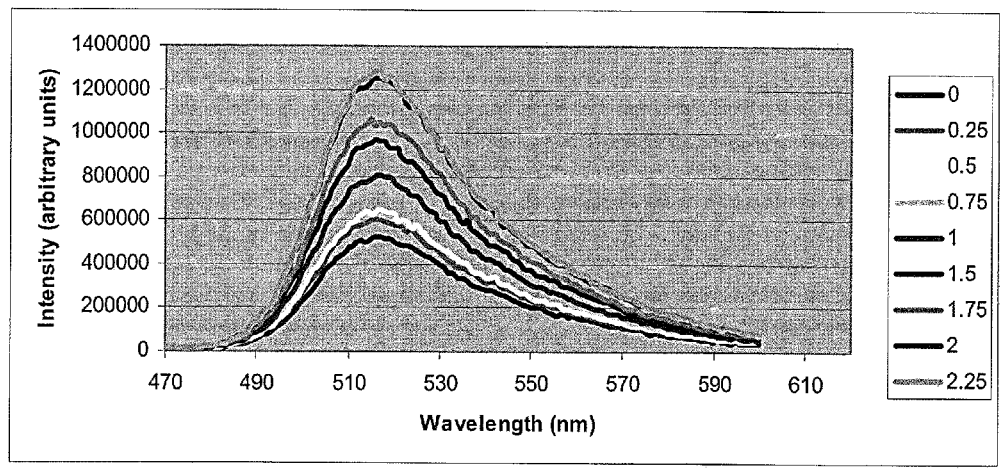
FIG. 12 shows the results of the fluorescent intensity of BLs with different interior tonicities from Example 4.
Figure 13:
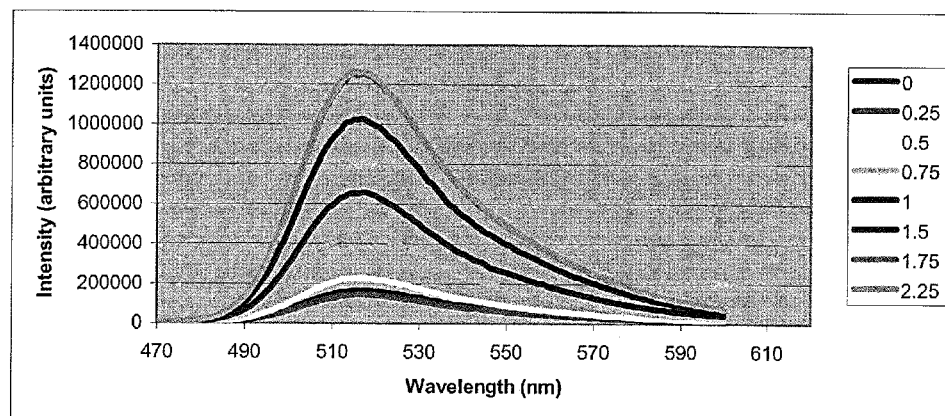
FIG. 13 shows the results of the fluorescent intensity of PCLs with different interior tonicities from Example 4.

Liposomes were prepared as described above. After incubating and purifying, both the sample (PILs and PCLs with consensus sequence crosslinkers) and the control (BLs) were diluted to a final tonicity of 5× HBS which induces 33.81 atm of osmotic pressure inside the liposomes (caused by the difference in tonicity of the solution trapped inside the liposome (10×) verses the tonicity of the of the solution outside the liposome (5×)). The solutions were incubated overnight at 37.5° C. and fluorescent intensity was measured as described above, as shown in FIG. 12 and FIG. 13.

Visual inspection of the samples indicated that neither the BLs nor the PCLs had leaked any of their contents. Leakage and subsequent dilution of carboxyfluorescein caused a noticable visual change in the color of the solution. The concentrated carboxyfluorescein inside the liposomes is a dark red color, and at low concentrations of liposomes appears orange. Upon leaking and dilution of the carboxyfluorescein, the solution turns bright fluorescent green. The initial hypothesis of this experiment was that a much smaller osmotic pressure would cause the BLs to leak nearly all of their contents, so this result was unexpected.

Taking the equation $\Delta P_{min}=(3\Gamma/R_0)(\gamma/\Gamma R_0)^{2/3}$, and average values for $\Gamma(0.1-1 \text{ J/m}^2)$ and $\gamma(0.02-0.2 \text{ nJ})$, and the radius (68.36 nm) of the mean diameter measured above (136.72 nm), the minimum osmotic pressure needed for leaking should be as low as 0.89 atm or as high as 8.9 atm, four to forty times lower than the actual applied pressure. Assuming that the values of $\Gamma$ and $\gamma$ are closely related (being measurements of the cohesive force between the lipid molecules), to get a liposome at this radius that would resist over 33 atm of osmotic pressure, the values of $\Gamma$ and $\gamma$ must be raised 4 times to 4 J/m² and 0.8 nJ, values much higher than reported average values for biological membranes.

To further explore these extremely pressure resistant liposomes, the liposomes were diluted to a final concentration of 5× HBS and 1M Brij-58 (a strong detergent used to disrupt the membrane). Visual inspection of this solution also showed no leakage of carboxyfluorescein from the membranes (no change from orange to green).

For the following tests, an unsaturated phospholipid (DOPC) was added to decrease the elasticity of the membrane and increase the water permeability.

2. Peptide Crosslinker+DOPC

BLs were prepared as described above using 27.5 mg DPPC (37.5 µmol, 51.5 mol %), 2.7 mg DOPC (3.4 µmol, 4.7 mol %), and 12.3 mg cholesterol (31.8 µmol, 43.8 mol %) hydrated in 10× HBS+100 mM carboxyfluorescein. The BLs (constituting 2 µmol of DPPC (1 eq.)) were added to 20 µL of the prepared polymer at 200 mg/mL (4 mg, 0.32 eq.), and diluted to 600 µL with 10× HBS. A control batch was also made by adding the BLs to 20 µL 10× HBS and diluting to 600 µL with 10× HBS. The integrated polymers were then crosslinked. PILs constituting 640 nmol DPPC+DOPC (1 eq.) were added to 5.8 mg EDC.MeI (19.5 µmol, 30 eq.) and incubated 2 hours at 37.5° C. After incubating, 20 µL of crosslinker at 40 mg/mL (36 nmol, 0.056 eq., 34% crosslinking assuming 100% reaction) was added and the preparation was incubated overnight at 37.5° C.

The preparation was purified as describe above, and the concentration of carboxyfluorescein in the PCLs and the BLs was measured, as described above. Both the sample and the control were diluted to 4 µM carboxyfluorescein and a final tonicity of either 10×, 9.75×, 9.5×, 9.25×, 9×, 8.5×, 8.25×, 8×, or 7.75× HBS (the solutions were marked by the difference in concentration (0, 0.25, 0.5, 0.75, 1, 1.5, 1.75, 2, and 2.25 respectively). The osmotic pressure against the 10× HBS inside the liposomes was calculated as 0, 1.69, 3.38, 5.07, 6.76, 10.14, 11.83, 13.52, and 15.21 atm, respectively. The solutions were incubated overnight at 37.5° C. and fluorescent intensity was measured as described above, as shown in FIG. 12 and FIG. 13.

Figure 14:
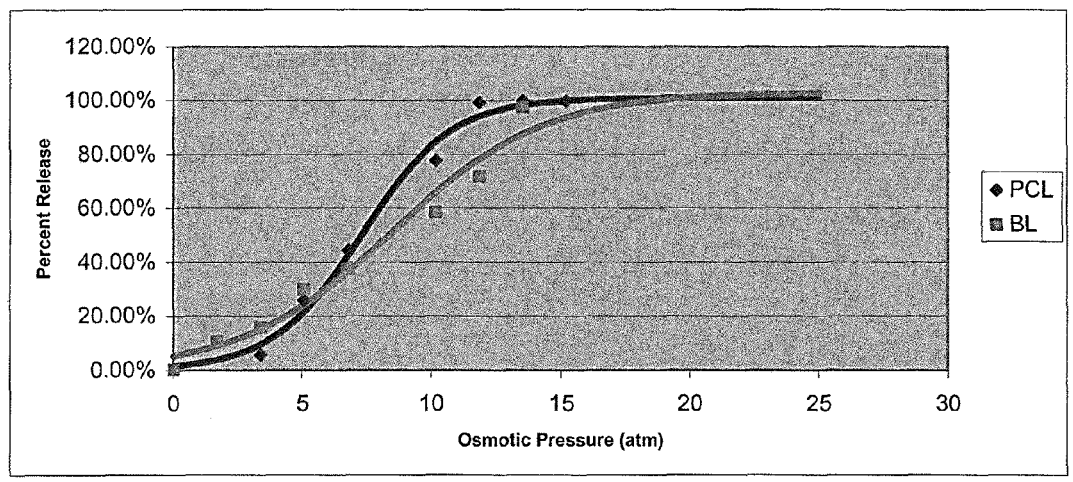
FIG. 14 is a graph of the fitting curve for % release versus osmotic pressure for BLs and PCLs from Example 4.

The total fluorescent intensity was scaled to a maximum of 100% and the percent release (which equals the scaled fluorescence values) was plotted against the osmotic pressure and the fitting constants were calculated (FIG. 14). The difference in percent release as a function of pressure was calculated by subtracting the percent release curve of the BLs from the percent release curve of the PCLs. The zero value line of the BL curve minus the PCL curve is also shown (FIG. 15).

Figure 15:
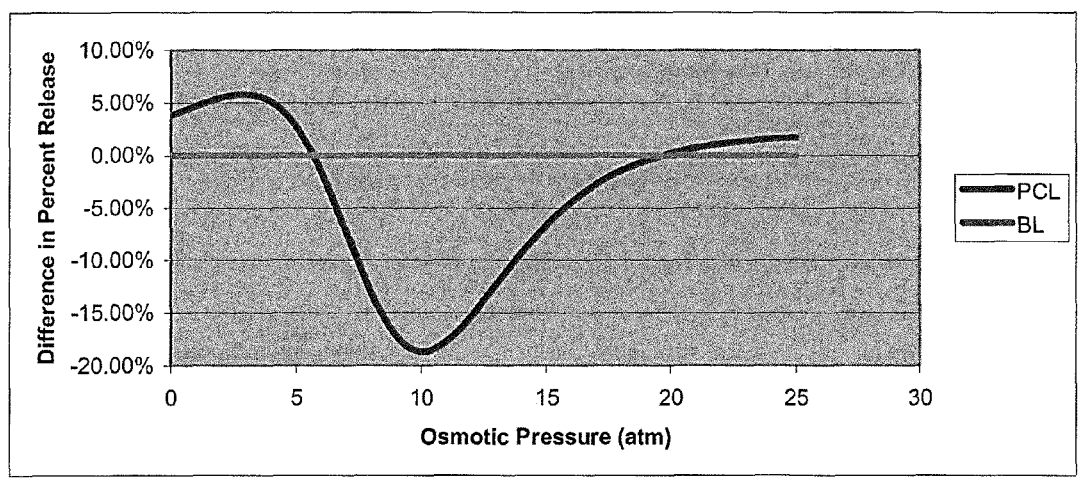
FIG. 15 is a graph of the difference in % release versus osmotic pressure from Example 4.

As can be seen in FIGS. 14-15, there is very little difference in the percent release at any osmotic pressure between the PCLs and the BLs. Ideally a large change would be seen in the pressure resistance of the PCLs that would show itself as a rightward shift in the fitting curve. Thus at intermediate pressures, a substantial difference in the percent release of the carboxyfluorescein would be seen.

TABLE

Fitting Constants for %
Release verses Osmotic Pressure

| | BL | PCL |
|---|---|---|
| A | 2.9171 | 2.6778 |
| B | 2.8325 | 2.6524 |
| C | 228.4391 | 228.4444 |
| D | −0.3448 | −0.5774 |
| E | −1.4654 | −0.2378 |
| $R^2$ | 0.99998953 | 0.99999502 |

The maximum pressure the polymer cage can withstand can be estimated from the fitting curves (FIG. 14). BLs should start to release their entrapped contents at $\Delta P_{min}$. $\Delta P_{min}$ can be estimated from the graph, and for most reliable results, the half maximum (when the carboxyflourescein is 50% released) is the best point for estimating. In the same way, the PCLs should start to release their entrapped contents at $\Delta P_{min}+P_{ext}$, or the pressure needed to break the liposome membrane plus the pressure needed to overcome the polymer shell. Again, this can be estimated from the graph as osmotic pressure at the half maximum of the polymer caged liposome release curve. $P_{ext}$ (the added maximum pressure resistance from the polymer cage) can be calculated by subtracting the osmotic pressure at half height of the bare liposome curve from the osmotic pressure at half height of the bare liposome curve. For this system, the osmotic pressure at half maximum for the BLs is 13.17 atm; the osmotic pressure at half height for the PCLs is 12.16 atm. Subtracting the two gives a maximum added pressure resistance from the polymer cage as −1.01 atm, or no significant added pressure resistance.

3. Ethylenediamine Crosslinkers

Additional PCLs were synthesized using ethylenediamine crosslinkers as follows. BLs were prepared as described above using 27.5 mg DPPC (37.5 µmol, 51.5 mol %), 2.1 mg DOPC (2.67 µmol, 3.7 mol %), and 12.6 mg cholesterol (32.6 µmol, 44.8 mol %) in 10× HBS with 100 mM carboxyfluorescein. The BLs (constituting 3 µmol of DPPC (1 eq.)) were added to either 15 µL (3 mg, 0.17 eq.), 30 µL (6 mg, 0.34 eq.), or 45 µL (9 mg, 0.50 eq.) of the prepared polymer at 200 mg/mL, and diluted to 4004 with 10× HBS. The resulting PILs, after incubating and purifying were added to either 46.5 µL (700 nmol, crosslinking percent depends on sample) or 70 µL (1000 nmol, crosslinking percent depends on sample) 1% ethylenediamine. This resulted in the following samples:

TABLE

Polymer Equivalents and Crosslinking in Samples

| Sample | Polymer Equivalents | Crosslinking % |
|---|---|---|
| 1 | 17% | 80% |
| 2 | 17% | 120% |
| 3 | 34% | 40% |
| 4 | 34% | 60% |
| 5 | 50% | 27% |
| 6 | 50% | 40% |

Figure 16:
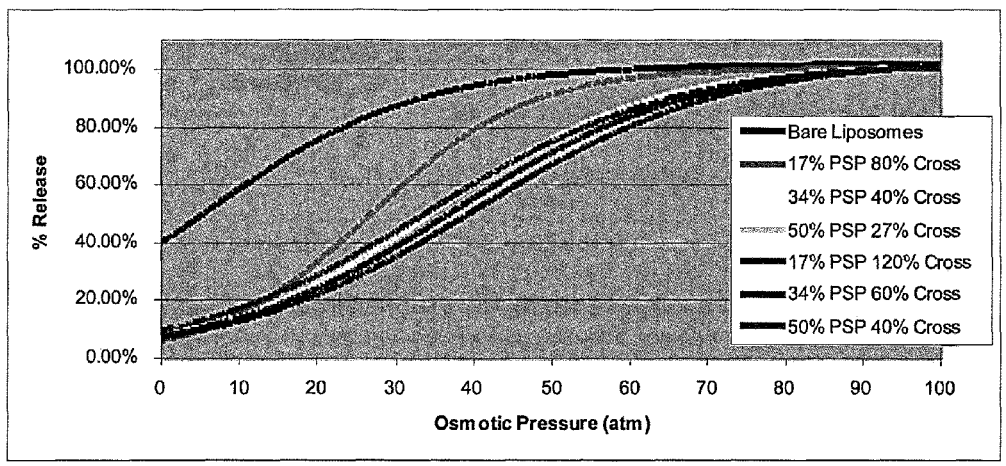
FIG. 16 is another graph of the fitting curve for % release versus osmotic pressure for BLs and PCLs from Example 4.

The additional PCLs synthesized above using ethylenediamine crosslinkers (Samples 1-6) were analyzed. After purification, the concentration of carboxyfluorescein in the PCLs and the BLs was measured. Both the samples and the control were diluted to 4 µM carboxyfluorescein and a final tonicity of either 10×, 9.75×, 9.5×, 9×, 8.5×, 7.5×, or 5× HBS (the solutions were marked by the difference in concentration (0, 0.25, 0.5, 1, 1.5, 2.5, and 5, respectively). The osmotic pressure against the 10×HBS inside the liposomes was 0, 1.69, 3.38, 6.76, 10.14, 16.90, and 33.81 atm, respectively. The solutions were incubated overnight at 37.5 ° C. and fluorescent intensity was measured. A summary graph of the fluorescent intensity and percent release verses osmotic pressure for all samples is shown in FIG. 16.

TABLE

Fitting Constants

|   | BL | 1 | 2 | 3 | 4 | 5 | 6 |
|---|---|---|---|---|---|---|---|
| A | 11.0279 | 10.8532 | 10.9297 | 10.9988 | 10.9737 | 11.0182 | 10.9708 |
| B | 10.8009 | 10.7729 | 10.7139 | 10.6431 | 10.6710 | 10.6194 | 10.7066 |
| C | 236.3898 | 236.3994 | 236.3986 | 236.3986 | 236.3985 | 236.3987 | 236.3973 |
| D | −0.0741 | −0.1000 | −0.0719 | −0.0648 | −0.0663 | −0.0634 | −0.0648 |
| E | −2.6624 | −0.4018 | −0.5928 | −0.5911 | −0.6161 | −0.5540 | −0.8823 |
| $R^2$ | 0.9999989 | 0.9999992 | 0.9999994 | 0.9999992 | 0.9999998 | 0.9999989 | 0.9999999 |

As can be seen in FIG. 16, the PCLs' curves shifted substantially to the right. This indicated that the polymer cage did add substantial resistance to osmotically-induced leakage. Again, the amount of added resistance to pressure ($P_{Max\ ext}$) can be estimated by subtracting the pressure at half maximum of the BLs ($P_{Half\ Max}$) from the $P_{Half\ Max}$ of the PCLs. The $P_{Max\ ext}$ and the $P_{Half Max}$ are shown in the table below.

TABLE

Maximum Added Pressure Resistance

| Sample | $P_{Half Max}$ (atm) | $P_{Max\ ext}$ (atm) |
|---|---|---|
| BL | 5.20 | 0.00 |
| 1 | 26.70 | 21.50 |
| 2 | 34.25 | 29.05 |
| 3 | 37.75 | 32.55 |
| 4 | 36.60 | 31.40 |
| 5 | 39.10 | 33.90 |
| 6 | 33.40 | 28.20 |

Figure 17:
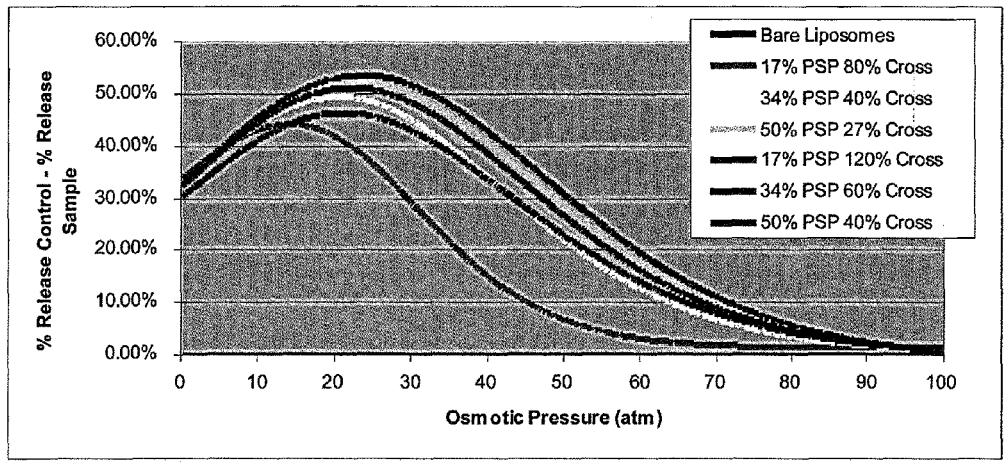
FIG. 17 is another graph of the difference in % release versus osmotic pressure from Example 4.

The $P_{Max\ ext}$ calculations represent a horizontal line across FIG. 16. When a protease degrades the polymer shell or cage, the osmotic pressure stays the same (isobaric) but the liposome looks more like a bare liposome post-degredation than a PCL. This means that the liposome should release its contents after the polymer cage has been degraded. The isobaric difference in release between the BLs and the PCLs can be calculated for each sample by subtracting the percent release curve for BLs from the percent release curve for the sample. The isobaric difference curves are shown in FIG. 17. The isobaric difference represents the maximum amount of entrapped solute that can be released by protease degredation, so higher values are preferential.

Sample 4 (0.34 eq. polymer, 60% crosslinking) showed the greatest difference in % release with a maximum % release of 53.84% at 23.5 atm. Sample 5 (0.50 eq. polymer, 40% crosslinking) did not show a substantially large difference. The smallest difference in % release was sample 1 (0.17 eq. polymer, 80% crosslinking), which may be due to low amount of polymer.

Figure 18:
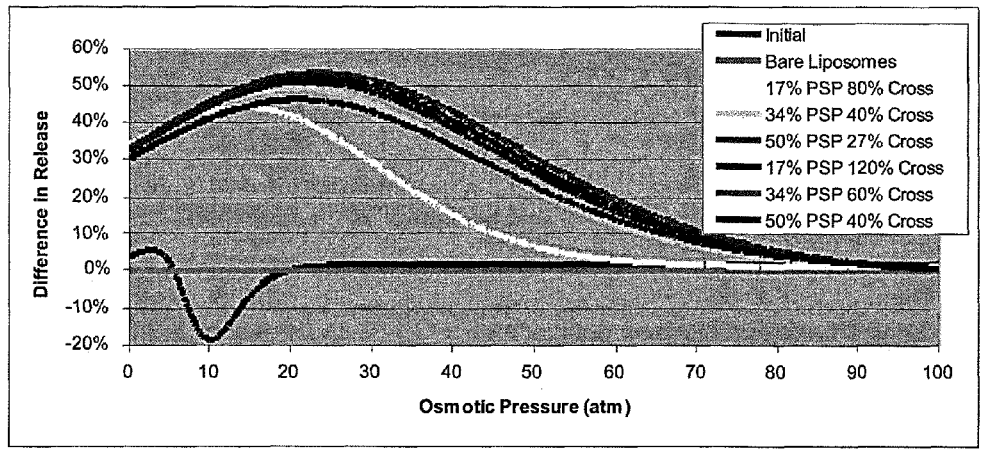
FIG. 18 is graph comparing FIG. 15 and FIG. 17.

To show the increase in effectiveness of the ethylenediamine compared to the peptide crosslinker, FIG. 15 was overlaid on FIG. 17 and is shown in FIG. 18. Ethylenediamine as a crosslinker dramatically increased the $P_{Max\ ext}$, lending credence to the theory that the earlier PCLs with peptide crosslinker was simply not tight enough to keep the liposome from swelling and bursting.

Example 5

Kinetics of Liposome Swelling

Although the swelling of the liposomes and the subsequent release of contents should be very fast in the presence of large osmotic pressures, this swelling and releasing is a transient state. This means that the liposome will swell, form pores, release some contents, and then the pores will seal again. If the pressure gradient is not minimized enough to prevent swelling the process starts again. Thus, even though each swelling and releasing process is very quick, it is concievable that the total release of contents may happen over a much longer time period.

To determine how quickly the contents of the liposomes are released in response to osmotic pressure BLs were prepared as described above using 27.5 mg DPPC (37.5 µmol, 51.5 mol %), 2.1 mg DOPC (2.67 µmol, 3.7 mol %), and 12.6 mg cholesterol (32.6 µmol, 44.8 mol %) in 10× HBS with 100 mM carboxyfluorescein. The BLs (constituting 3 µmol of DPPC (1 eq.)) were added to 30 µL (6 mg, 0.34 eq.) of the block copolymer at 200 mg/mL, and diluted to 400 µL with 10× HBS. The resulting PILs, after incubation and purification, were added to 70 µL 1% ethylenediamine (1000 nmol, 60% crosslinking) to produce the PCLs.

Next, the concentration of carboxyfluorescein in the PCLs and the BLs was measured as described above. Both the sample and the control were diluted to 4 µM carboxyfluorescein and a final tonicity of either 10×, 9.5×, 9×, 8×, 7×, 6×, or 5× HBS (the solutions were marked by the difference in concentration (0, 0.5, 1, 2, 3, 4, and 5, respectively). The osmotic pressure against the 10× HBS inside the liposomes was 0, 3.38, 6.76, 13.52, 20.28, 27.04, and 33.81 atm, respectively. The solutions were incubated at 37.5° C., and fluorescent intensity was measured at time 0 (15 min), 2 hours, 5 hours, 24 hours, 47 hours, and 71 hours, as described above. Fluorescent intensity and percent release verses osmotic pressure can be seen in the summary graph compiling all of the calculated curves in FIG. 19 for the BLs and FIG. 20 for the PCLs.

Figure 19:
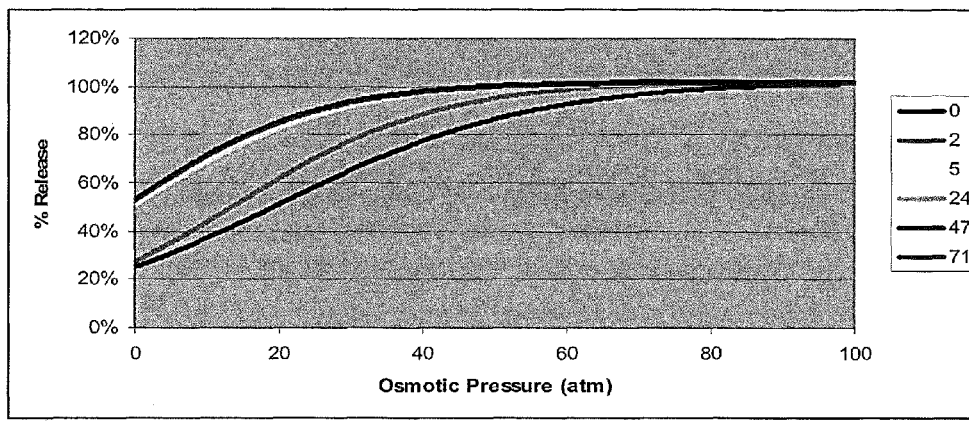
FIG. 19 is a graph of the fitting curve for % release versus osmotic pressure for BLs from Example 5.
Figure 20:
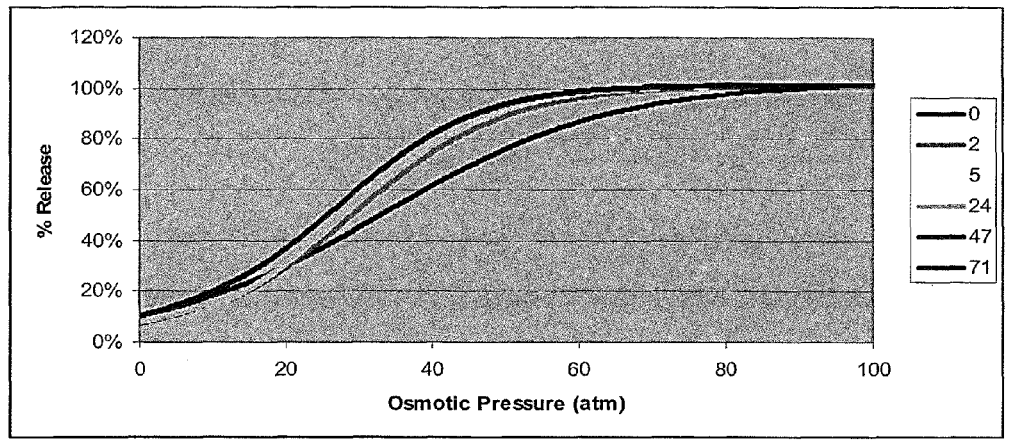
FIG. 20 is a graph of the fitting curve for % release versus osmotic pressure for PCLs from Example 5.

As can be seen from FIG. 19, it takes more than 2 hours but less than 5 hours for the BLs to reach osmotic equilibrium (no more increase in % release). In FIG. 20, the PCLs take more than 15 minutes but less than 2 hours to reach osmotic equilibrium. In the BLs, the osmotic pressure causes the liposome to swell and form pores, releasing some of the contents and the pores close again. This continues to happen over time, and each time it happens, the osmotic pressure goes down. As the osmotic pressure goes down, the speed of pore formation also slows down. Thus the BLs will take some time to reach equilibrium because their progress towards equilibrium is slowed. At higher pressures, the liposomes will reach equilibrium faster and at lower pressures the liposomes will reach equilibrium slower because of less initial rate, which can be seen in the curve at 2 hours. On the other hand, PCLs start out the same. They swell for a moment and release a little bit of their contents. They would continue in the bare liposome trend of swell, pore, release, close, repeat, but they quickly expand into the polymer cage and are trapped. Thus the point of equilibrium is not equalizing the osmotic pressure inside and out, but rather running into the polymer cage. Since the time it takes to expand into the polymer cage is much less than the time it takes to release all of the contents, the PCLs reach "equilibrium" much faster. The difference in percent release at each pressure and time can be calculated again by subtracting the sample curve from the control curve at the same time. Because of the difference in rate of how quickly the bare liposome reach equilibrium at high and low pressures, the difference graph not only grows larger over time but also moves to the left (to lower osmotic pressures).

Figure 21:
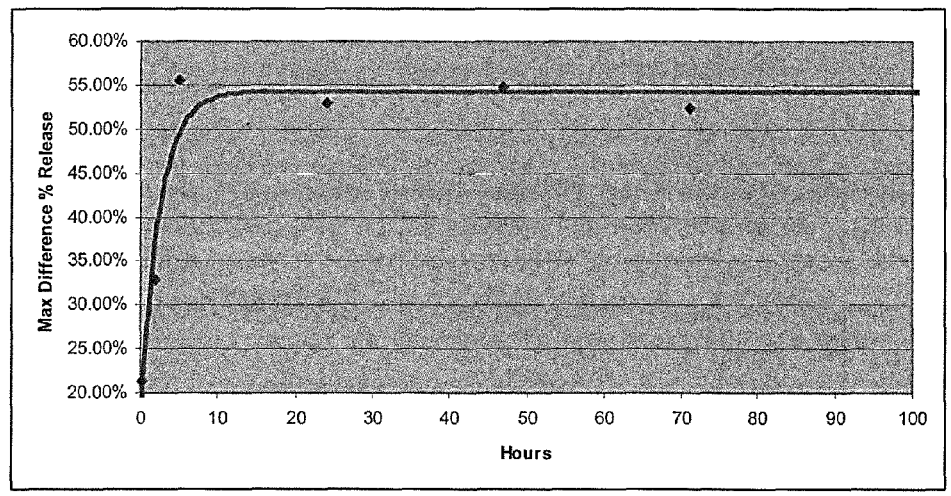
FIG. 21 is a graph of the maximum difference in release versus time from Example 5.
Figure 22:
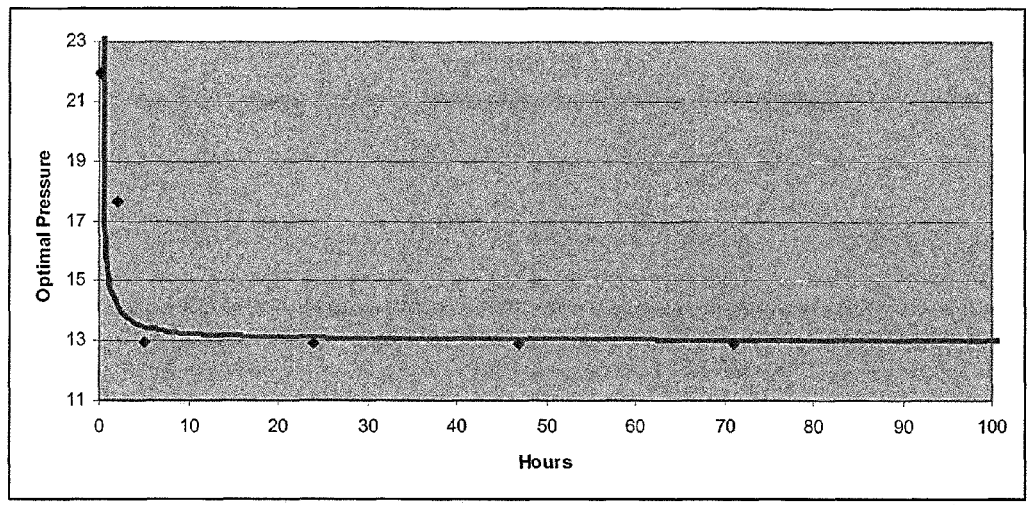
FIG. 22 is a graph of the optimal pressure for release versus time from Example 5.

The change in both of the variables (maximum difference in release and pressure at maximum difference in release) can be graphed verses time. These are shown in FIGS. 21-22.

Because of the time that it takes for the liposomes to reach osmotic equilibrium, all further fluorescence measurements were taken at least 16 hours after starting the experiment to ensure that both the BLs and the PCLs had reached osmotic equilibrium but remained within the tested window for stability of results (results stay stable for at least three days, the maximum testing period).

Example 6

Membrane Concentration

In order to maximize the pressure resistance of the PCLs, the composition of the membrane was examined. The membrane consists of three parts: DPPC, cholesterol, and DOPC. The concentrations of DOPC and cholesterol in the membrane were changed to determine their effect on $P_{Max\ ext}$.

1. Oleic Acid Content

To determine how oleic acid concentration affects $P_{Max\ ext}$, BLs were prepared as described above using:
1. 27.5 mg DPPC (37.5 μmol, 51.5 mol %), 2.1 mg DOPC (2.67 μmol, 3.7 mol %), and 12.6 mg cholesterol (32.6 μmol, 44.8 mol %);
2. 28 mg DPPC (38.1 μmol, 52.6 mol %), 1.4 mg DOPC (1.78 mol, 2.5 mol %) and 12.6 mg cholesterol (44.9 mol %); or
3. 28.5 mg DPPC (38.8 μmol, 53.7 mol %), 0.7 mg DOPC (0.89 μmol, 1.2 mol %) and 12.6 mg cholesterol (45.1 mol %), each in 10× HBS with 100 mM carboxyfluorescein. The BLs (constituting 3 μmol of DPPC (1 eq.)) were added to 30 μL (6 mg, 0.34 eq.) of the prepared polymer at 200 mg/mL, and diluted to 400 μL with 10× HBS. The resulting PILs, after incubation and purification were added to 70 μL 1% ethylenediamine (1000 nmol, 60% crosslinking), followed by incubation and purification, to prepare the PCLs.

Figure 23:
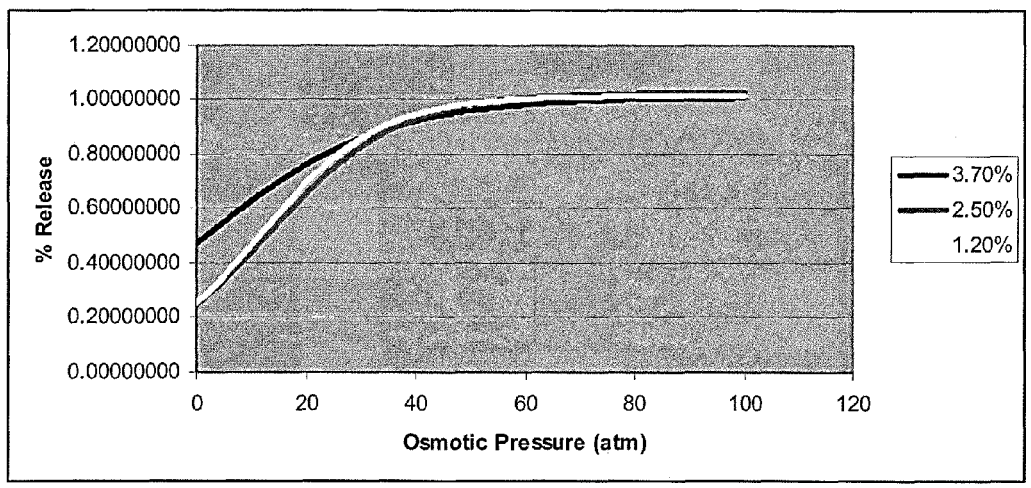
FIG. 23 is a graph of the fitting curve for % release versus osmotic pressure for BLs with different oleic acid contents from Example 6.
Figure 24:
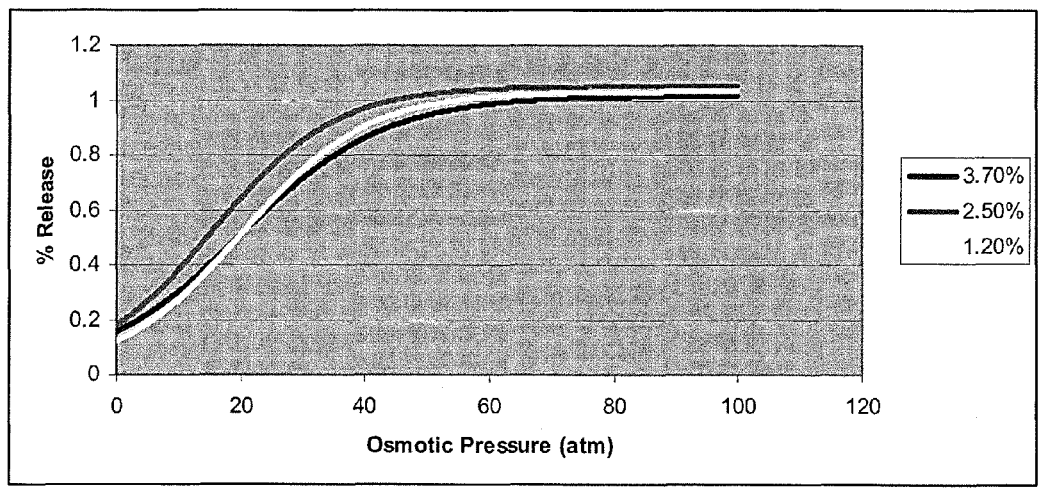
FIG. 24 is a graph of the fitting curve for % release versus osmotic pressure for PCLs with different oleic acid contents from Example 6.

The concentration of carboxyfluorescein in the PCLs and the BLs was measured as described above. Both the sample and the control were diluted to 4 μM carboxyfluorescein and a final tonicity of either 10×, 9.5×, 9×, 8×, 7×, 6×, or 5×HBS (the solutions were marked by the difference in concentration (0, 0.5, 1, 2, 3, 4, and 5, respectively). The osmotic pressure against the 10× HBS inside the liposomes was 0, 3.38, 6.76, 13.52, 20.28, 27.04, and 33.81 atm respectively. The solutions were incubated at 37.5 ° C. overnight and fluorescent intensity was measured as described above. Fluorescent intensity and percent release verses osmotic pressure can be seen in the summary graph compiling all of the calculated curves in FIG. 23 for the BLs and FIG. 24 for the PCLs.

Figure 25:
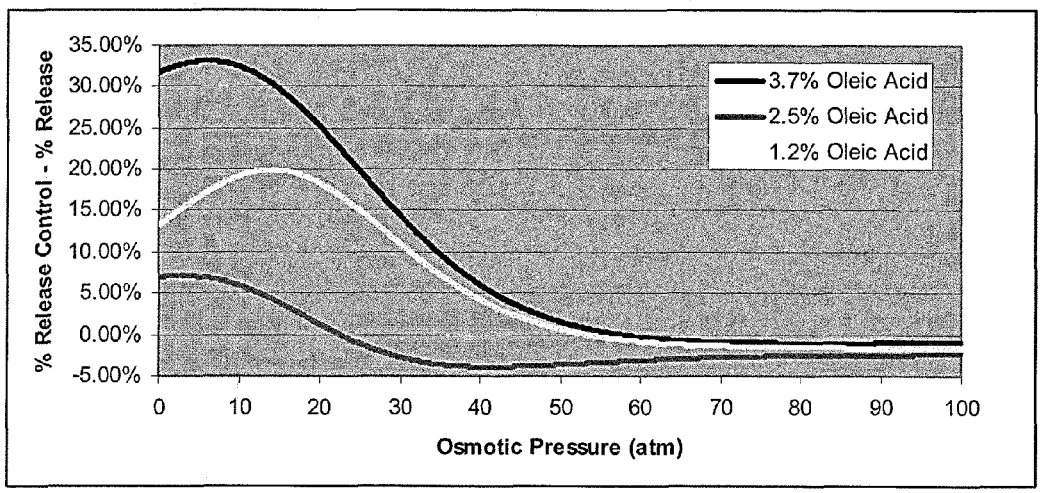
FIG. 25 is a graph of the difference in % release versus osmotic pressure at various oleic acid contents from Example 6.

The results indicate that lower concentrations of DOPC lowered the percent release at lower osmotic pressures. FIG. 25. This is consistent with the earlier findings that DOPC is necessary to allow water permeability and reduce membrane elasticity. As the amount of DOPC is lowered, the pressure needed to cause effective pressure in the membrane becomes larger, making the lower pressures reduce their percent release. Lowering the concentration of DOPC did not affect the percent release of the PCLs significantly. This also fits into earlier findings. The PCLs are not dependent on membrane elasticity as the main pressure resistance. Thus, changing the elasticity and water permeability of the membrane does not significantly change the percent release.

2. Cholesterol Content

To determine how cholesterol concentration affects $P_{Max\ ext}$, BLs were prepared as described above using:
1. 27.5 mg DPPC (37.5 μmol, 51.5 mol %), 2.1 mg DOPC (2.67 μmol, 3.7 mol %), and 12.6 mg cholesterol (32.6 μmol, 44.8 mol %); or
2. 27.5 mg DPPC (38.1 μmol, 74.6 mol %), 2.1 mg DOPC (1.78 μmol, 5.3 mol %) and 3.9 mg cholesterol (10.1 μmol, 20.1 mol %), each in 10× HBS with 100 mM carboxyfluorescein. The BLs (constituting 3 μmol of DPPC (1 eq.)) were added to 30 μL (6 mg, 0.34 eq.) of the prepared polymer at 200 mg/mL, and diluted to 400 μL with 10× HBS. The resulting PILs, after incubating and purifying, were added to 70 μL 1% ethylenediamine (1000 nmol, 60% crosslinking), followed by incubation and purification as described, to yield the PCLs.

The concentration of carboxyfluorescein in the PCLs and the BLs was measured as described above. Both the sample and the control were diluted to 4 μM carboxyfluorescein and a final tonicity of either 10×, 9.5×, 9×, 8×, 7×, 6×, or 5× HBS (the solutions were marked by the difference in concentration (0, 0.5, 1, 2, 3, 4, and 5, respectively). The osmotic pressure against the 10x HBS inside the liposomes was 0, 3.38, 6.76, 13.52, 20.28, 27.04, and 33.81 atm, respectively. The solutions were incubated at 37.5 ° C. overnight and fluorescent intensity was measured as described above. Fluorescent intensity and percent release verses osmotic pressure can be seen in the summary graph compiling all of the calculated curves in FIG. 26 for the BLs and FIG. 27 for the PCLs.

Figure 26:
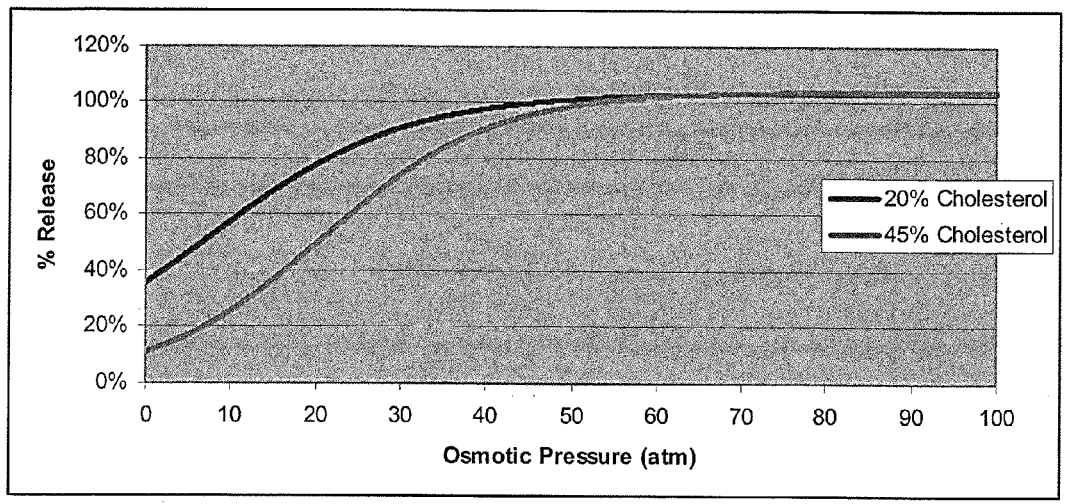
FIG. 26 is a graph of the fitting curve for % release versus osmotic pressure for BLs with different cholesterol contents from Example 6.
Figure 27:
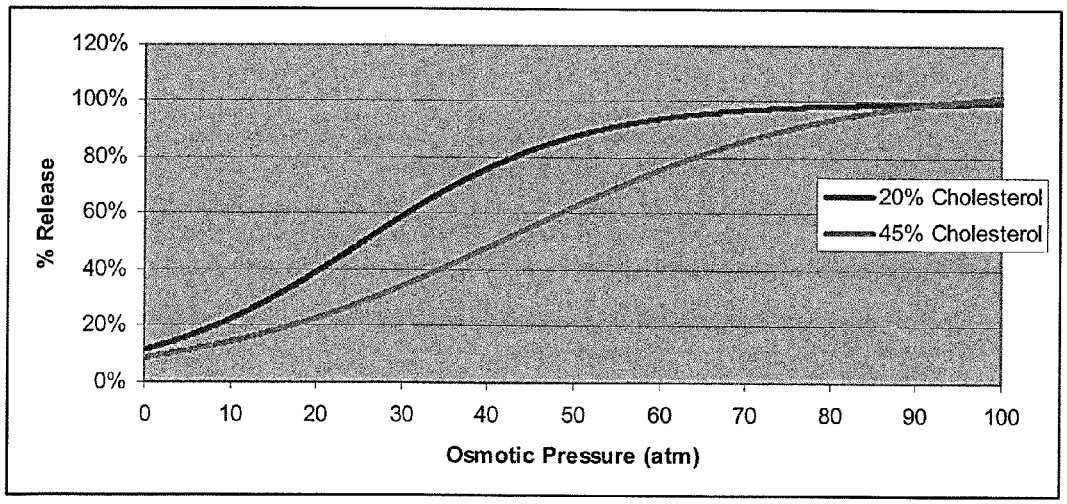
FIG. 27 is a graph of the fitting curve for % release versus osmotic pressure for PCLs with different cholesterol contents from Example 6.

Since the cholesterol level was already nearly saturated only lower concentrations of cholesterol were tested. As can be seen in FIGS. 26-27, lowering the cholesterol level shifts $P_{Half\ Max}$ of both the BLs and the PCLs to the left. The change is approximately the same for both BLs and PCLs, so the $P_{Max\ ext}$ value does not change. The optimal osmotic pressure does shift to the left, though. $P_{Half\ Max}$, $P_{Max\ ext}$ and optimal pressure values are shown in the table below.

TABLE $P_{Half\ Max}$, $P_{Max\ ext}$ and Optimal Pressure

|  | 20% Chol | 45% Chol |
|---|---|---|
| BL | 6.55 | 20.2 |
| PCL | 25.5 | 41.4 |
| $P_{max\ ext}$ | 18.95 | 21.2 |
| Opt P | 17.95 | 37.25 |

Taking these results with the results above for differences in oleic acid concentration, the activities of cholesterol and oleic acid can be determined. Oleic acid concentration affects only the BLs and not the PCLs. Cholesterol concentration affects both BLs and PCLs. On the other hand, water permeability will affect both BLs and PCLs approximately the same because decreased water permeability reduces the effective osmotic pressure of the system. Reducing the effective osmotic pressure will increase $P_{Half\ Max}$ for both BLs and PCLs.

Figure 28:
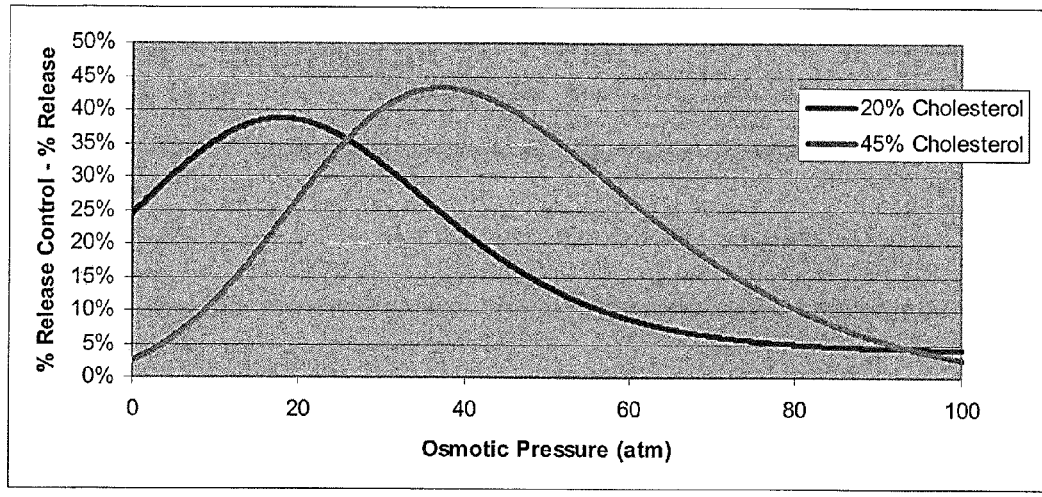
FIG. 28 is a graph of the difference in % release versus osmotic pressure at various cholesterol contents from Example 6.

The isobaric difference in release can also be calculated for the different cholesterol concentrations and is shown in FIG. 28. As would be expected from the $P_{Half\,Max}$ and $P_{Max\,ext}$ values, the maximum difference in release is not much different between low and high concentrations of cholesterol in the membrane. The pressure at the maximum difference does shift to the right with increasing cholesterol concentration, though.

Example 7

Revisiting Polymer Content and Concentration

In Example 4.3, several different polymer contents and crosslinking % were tried using an ethylenediamine crosslinker. The polymer content tested spanned a wide range of equivalence values verses the lipid content, but did not span a wide range of distances between polymer molecules. In fact, 0.017 eq. of polymer equals an average of 5.3 nm between polymers in the membrane, 0.034 eq. of polymer equals an average of 3.7 nm, and 0.050 eq. of polymer equals an average of 3.1 nm between polymers. Since the polymer, fully stretched, is nearly 12 nm long, these values allow substantial, if not excessive overlap. To see if a less overlap (and thus a polymer that was already more stretched out) would increase the isobaric difference between BLs and PCLs and/or $P_{Max\,ext}$, polymer equivalents were added to BLs so that there would be, on average, either 3 nm, 6 nm, or 9 nm between the polymers (increasing the range tested by 50%).

Also, because the diamine crosslinker was chosen as an equivalent to lipid content and not as an equivalent to acrylic acid residue concentration, somewhat random (and sometimes irrational) percent crosslinking was calculated for the liposomes. To more methodically determine ideal percent crosslinking, the amount of crosslinker was chosen as an equivalent to acrylic acid residue content at either 25% (50% crosslinking because each crosslinker crosslinks two residues), 37.5% (75% crosslinking), or 50% (100% crosslinking).

BLs were synthesized as described above using 27.5 mg DPPC (37.5 μmol, 47.5 mol %), 3.1 mg DOPC (3.9 μmol, 5.0 mol %), and 14.5 mg cholesterol (37.5 μmol, 47.5 mol %) hydrated in 10× HBS with 100 mM carboxyfluorescein. The BLs (constituting 4 μmol DPPC+DOPC (1 eq.) were added to either 25 nmol (0.006 eq., average 9 nm between polymers), 53 nmol (0.013 eq., average 6 nm between polymers), or 212 nmol (0.053 eq., average 3 nm between polymers) of the synthesized block copolymer, and then diluted to 600 μL. These were designated low (L), medium (M), or high (H) samples, respectively.

After incubating overnight to prepare PILs, EDC.MeI and ethylenediamine were added without a purification step (one-pot procedure) in order to increase yield. To the low sample, either 146 nmol (0.036 eq., 50% crosslinking), 219 nmol (0.055 eq., 75% crosslinking), or 292 nmol (0.073 eq., 100% crosslinking) were added along with EDC.MeI at 1500:1 EDC:ethylenediamine. These were designated L50, L75, and L100 respectively. To the medium sample, either 313 nmol (0.078 eq., 50% crosslinking), 470 nmol (0.117 eq., 75% crosslinking), or 626 nmol (0.157 eq., 100% crosslinking) of ethylenediamine were added along with with EDC.MeI at 1500:1 EDC:ethylenediamine. These were designated M50, M75, and M100, respectively. To the high sample either 1250 nmol (0.313 eq., 50% crosslinking), 1880 nmol (0.470 eq., 75% crosslinking), 2500 nmol (0.626 eq., 100% crosslinking) of ethylenediamine were added along with with EDC.MeI at 1500:1 EDC:ethylenediamine. These were designated HSO, H75 and H100, respectively.

Figure 29:
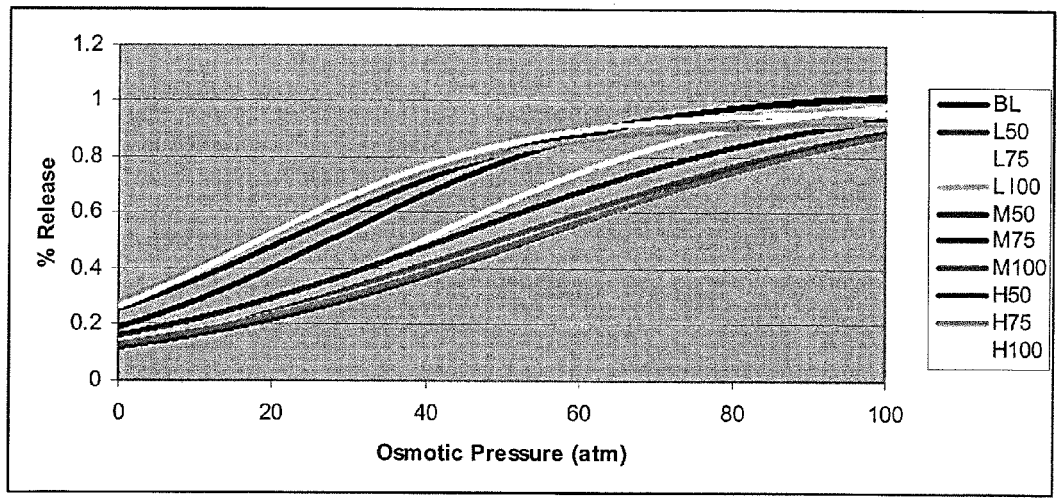
FIG. 29 is a summary graph compiling all of the calculated curves for fluorescent intensity and percent release verses osmotic pressure from Example 7.
Figure 30:
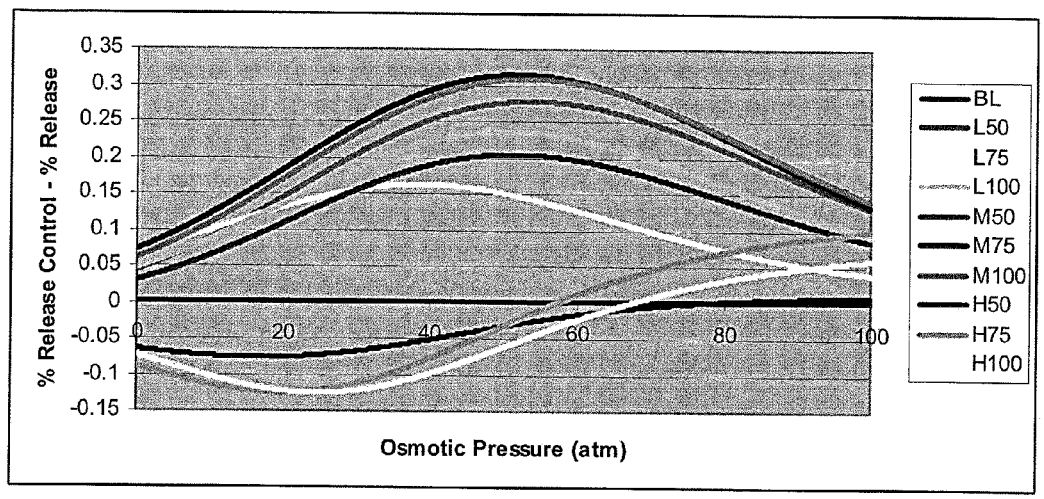
FIG. 30 is a summary graph of the calculated curves for the difference in % release versus osmotic pressure from Example 7.

After incubation and purification, the concentration of carboxyfluorescein in the PCLs and the BLs were measured. Both the sample and the control were diluted to 4 μM carboxyfluorescein and a final tonicity of either 10×, 9.5×, 9×, 8×, 7×, 6×, 5×, 3×, 1×, or 0.5× HBS (the solutions were marked by the difference in concentration (0, 0.5, 1, 2, 3, 4, 5, 7, 9, and 9.5, respectively). The osmotic pressure against the 10× HBS inside the liposomes was 0, 3.38, 6.76, 13.52, 20.28, 27.05, 33.81, 47.33, 60.85, and 64.23 atm, respectively. The solutions were incubated at 37.5° C. overnight and fluorescent intensity was measured. Fluorescent intensity and percent release verses osmotic pressure can be seen in the summary graph compiling all of the calculated curves in FIG. 29 and the isobaric difference curves are shown in FIG. 30.

The top six values for maximum difference in percent release verses control were all from samples with spacing farther apart (lower percent polymer) than the original Samples 1-6. This would indicate that having less overlap between the polymers is a good thing. This is a reasonable result, because polymers that start out more stretched out are going to have less expansivity than loose polymers (and polymers that have to stretch farther to crosslink will be more stretched out). Thus, the membrane will expand less due to osmotic pressure before interacting with the polymer cage and will thus release less of the liposomal contents in the expansion process. The drawback could be a weaker polymer cage, but the data does not support this. The lower polymer integration level liposomes start out at low osmotic pressures with lower leakage and continue to be lower when the osmotic pressure is raised. There does seem to be a drop off in polymer cage strength in the very low integration levels (spacing average 9 nm apart).

TABLE $P_{Half\,Max}$ and $P_{Max\,ext}$ Values

|  | $P_{Half\,Max}$ | $P_{Max\,ext}$ | Area Under Difference Curve |
| --- | --- | --- | --- |
| BL | 27.3 | 0 | 0 |
| L50 | 49.25 | 21.95 | 393 |
| L75 | 39.5 | 12.2 | 222 |
| L100 | 45.35 | 18.05 | 331 |
| M50 | 42.1 | 14.8 | 282 |
| M75 | 53.2 | 25.9 | 451 |
| M100 | 52.55 | 25.25 | 441 |
| H50 | 21.65 | −5.65 | −68 |
| H70 | 17.85 | −9.45 | −48 |
| H100 | 18.15 | −9.15 | −90 |

The very high concentration of polymer (average spacing 3 nm apart) actually shows very little difference from BLs. This is probably due to a very large expansivity of the polymer cage before it will resist osmotic pressure. Although the polymer cage is well crosslinked, since the polymer is very close together, it can be stretched apart a little bit before the crosslinking is truly tight. In very high concentrations of polymer, the expansivity appears to be greater than the maximum membrane expansivity, so the liposomes will leak out all of their contents before the polymer shell will provide resistance to osmotic pressure.

Thus, the optimal spacing between polymers appears to be between 5 and 6 nm on average (1.3%-1.9% polymer). If the spacing is too tight, the liposome can be only slowly activated by proteases cleaving their respective consensus sequence. If the spacing is less tight, the liposome will be prone to leaking its payload prior to enzymatic activation. These values of polymer integration have consistently had the highest isobaric pressure differences and the highest $P_{Max\,ext}$ values. The optimal value of crosslinking seems to depend strongly on polymer integration level. At higher integrations, less crosslinking seems to be preferred, while at lower integrations, more crosslinking seems to be preferred.

Example 8

Urokinase Release of Contents

1. Initial Test

BLs were prepared using 27.5 mg DPPC (37.5 µmol, 51.5 mol %), 2.1 mg DOPC (2.67 µmol, 3.7 mol %), and 12.6 mg cholesterol (32.6 µmol, 44.8 mol %) in 4.75× HBS with 100 mM carboxyfluorescein. The BLs (constituting 3 µmol of DPPC (1 eq.)) were added to 30 µL (6 mg, 0.34 eq.) of the prepared polymer at 200 mg/mL and diluted to 400 µL with 4.75× HBS. The resulting PILs, after incubating and purifying were added to 70 µL 1% ethylenediamine (1000 nmol, 40% crosslinking). This is the same as Sample 4 from Example 4.3 except in 4.75× HBS instead of 10× HBS. The liposomes were purified as described above to yield the PCLs.

Figure 31:
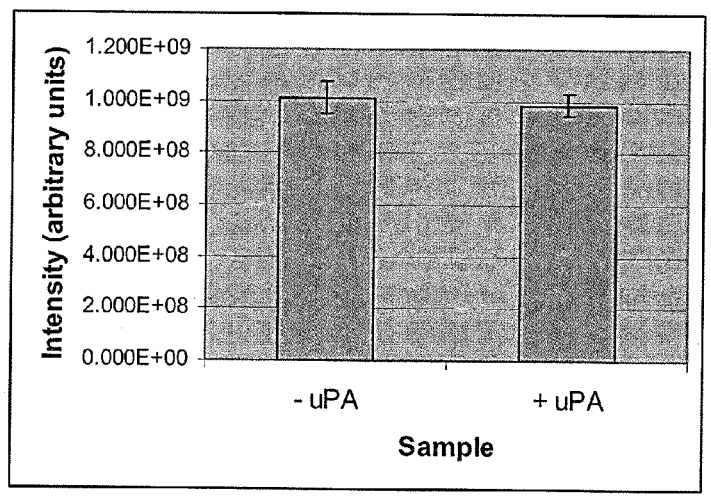
FIG. 31 is a graph of the calculated average total fluorescent intensity for each sample in the first test of Example 8.

The concentration of carboxyfluorescein in the PCLs was measured as described above. The liposomes were diluted to 4 µM carboxyfluorescein and a final tonicity of 4.75× HBS and the sample had either no uPA added or 25 µg/mL uPA added. The osmotic pressure against the 4.75× HBS inside the liposomes was 25 atm. The solutions were incubated overnight at 37.5° C. and fluorescent intensity was measured as described above. Fluorescent intensity can be seen in the summary graph showing average total fluorescent intensity in FIG. 31.

The results show there was very little difference between the no uPA sample and the uPA sample, indicating that the polymer caged liposome did not have the desired sensitivity to uPA (p=0.5173). It was hypothesized that the liposomes were either not sensitive to uPA or the uPA that was used was not active for some reason.

2. Second Test

The experiment was repeated using a fresh batch of uPA. BLs were synthesized using 27.5 mg DPPC (37.5 µmol, 47.5 mol %), 3.1 mg DOPC (3.9 µmol, 5.0 mol %), and 14.5 mg cholesterol (37.5 µmol, 47.5 mol %) hydrated in 8× HBS with 100 mM carboxyfluorescein. The BLs (constituting 4 mol DPPC+DOPC (1 eq.)) were added to 53 nmol (.013 eq., average 6 nm between polymers)) of the synthesized polymer and diluted to 600 µL.

After incubating overnight to prepare PILs, EDC.MeI and ethylenediamine were added without a purification step (one-pot procedure) in order to increase yield. To the PILs, 470 nmol (0.117 eq., 75% crosslinking) of ethylenediamine were added along with with EDC.MeI at 1500:1 EDC:ethylenediamine to produce the PCLs.

Figure 32:
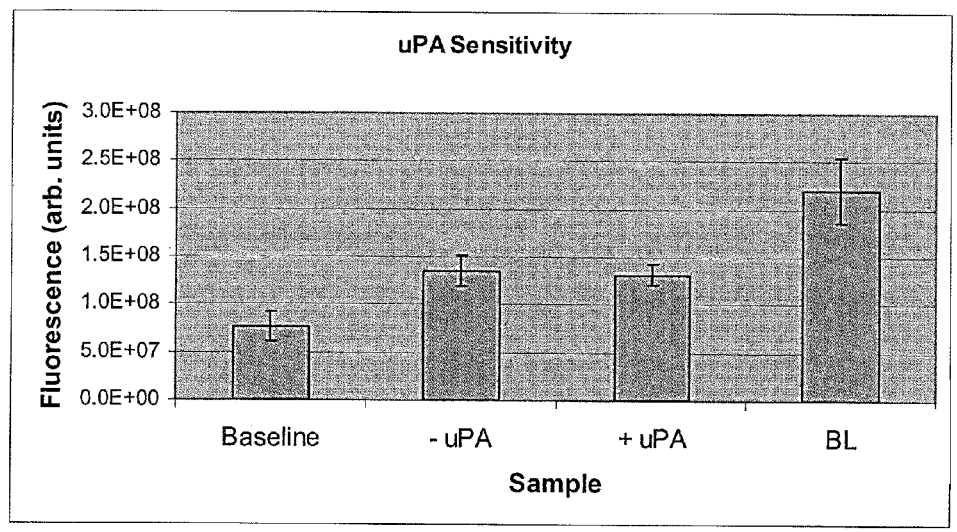
FIG. 32 is a graph of the calculated average total fluorescent intensity for additional samples in the second test of Example 8.

After incubating and purifying, the concentration of carboxyfluorescein in the PCLs and the BLs were measured as described above. Both the BLs and PCLs were diluted to 4 µM carboxyfluorescein and a final tonicity of 1× HBS without uPA (for a positive and negative control). PCLs were also diluted to 4 µM carboxyfluorescein and a final tonicity of 1× HBS with 25 µg/mL uPA (as the sample). Finally, PCLs were also diluted to 4 µM carboxyfluorescein and a final tonicity of 8× HBS without uPA (as a baseline value). The osmotic pressure in 1× HBS against the 8× HBS inside the liposomes was 47.33 atm (8× verses 8× is 0 atm). The solutions were incubated at 37.5° C. overnight and fluorescent intensity was measured. Fluorescent intensity can be seen in the summary graph showing average total fluorescent intensity in FIG. 32. T-test P values for each comparison are given in the table below.

TABLE

| t test | Base vs −uPA | Base vs +uPA | − uPA vs +uPA | Base vs BL | −uPA vs BL | +uPA vs BL |
|---|---|---|---|---|---|---|
| T-test P Values | | | | | | |
| p value | <0.0001 | 0.0001 | 0.6617 | 0.0001 | 0.0009 | 0.0009 |
| Significant | Yes | Yes | No | Yes | Yes | Yes |

As expected, the −uPA value was somewhat above baseline, indicating a small amount of leakage with osmotic stress but significantly lower than the BL at the same osmotic pressure. The most important result is the comparison of the +uPA and −uPA samples. They show very little difference in total intensity and the p value is 0.6617 between the two, indicating that they are not different. Thus, the PCLs still did not have the desired sensitivity to uPA, despite the use of a fresh batch of uPA.

3. Third Test

Figure 33:
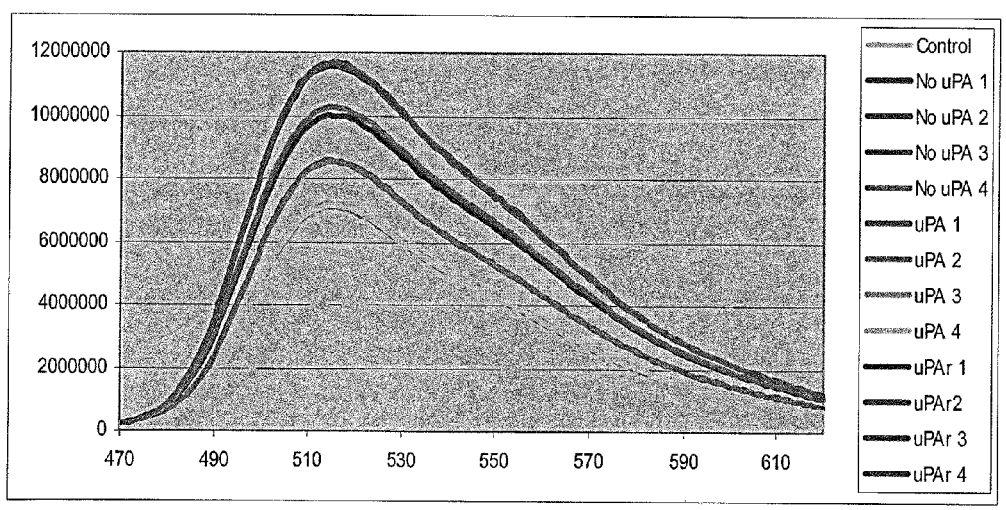
FIG. 33 shows the fluorescent intensities for the various samples from the third test in Example 8.

It was hypothesized that there was nothing wrong with the uPA of either batch, except that it had become denatured during storage. To test this last possibility, the same liposomes were prepared as in the second test above. The same fluorescent test samples were prepared as well, with the exception of the baseline sample (which was considered unnecessary). Thus there was a −uPA sample as a negative control, a BL sample as a positive control, and a +uPA sample as the test sample. A fourth sample was also introduced that had renatured uPA in it. A sample of uPA was renatured by heating to 90° C. for 5 minutes and then cooling to room temperature and repeating twice. This sample of uPA was also used to make a +uPA sample, so that there were two +uPA samples one with non-renatured uPA and one with renatured uPA. Fluorescent intensities can be seen in FIG. 33 and a summary graph of total fluorescent intensity can be seen in FIG. 34 and p values can be seen in the table below.

TABLE

| t test | No uPA/ uPA | No uPA/uPA RN | uPA/uPA RN | uPA RN/ BL | uPA/ BL | No uPA/ BL |
|---|---|---|---|---|---|---|
| T-Test P Values | | | | | | |
| p value | 0.3426 | 0.0071 | 0.0203 | 0.0888 | 0.0032 | 0.0093 |
| Significant | No | Yes | Yes | No | Yes | Yes |

Figure 34:
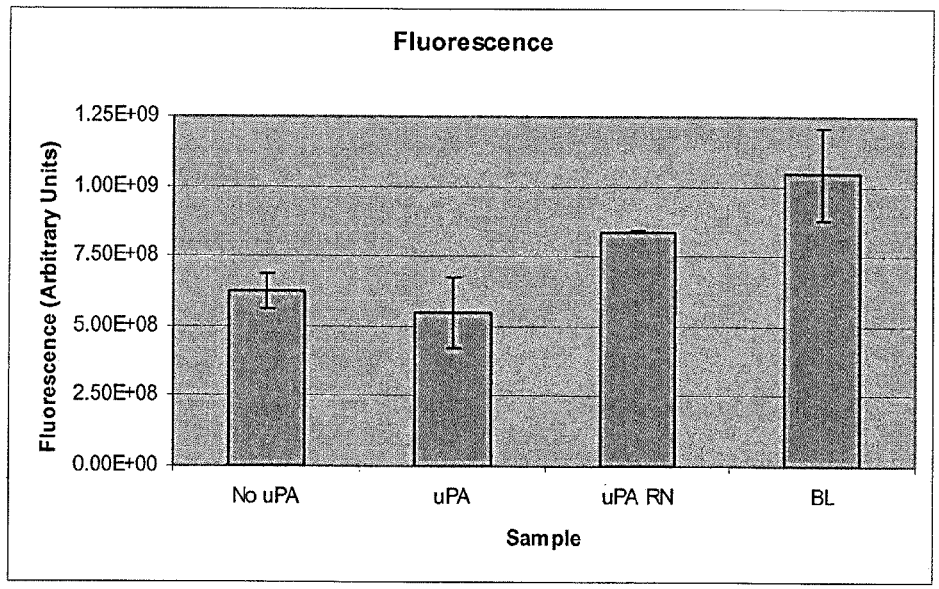
FIG. 34 is a graph of the calculated average total fluorescent intensity for each sample in the third test of Example 8.

As can be seen in FIG. 34, there is a difference between the uPA and uPA renatured sample, indicating that the uPA used in previous studies was, in fact, denatured. More importantly, there is a difference between the no uPA sample and the uPA sample with the uPA sample being significantly higher (p value 0.0071). The PCLs were sensitive to the renatured uPA and released their contents in response to uPA activity, as intended.

Example 9

Detecting Protease Activity Via Current

Figure 35:
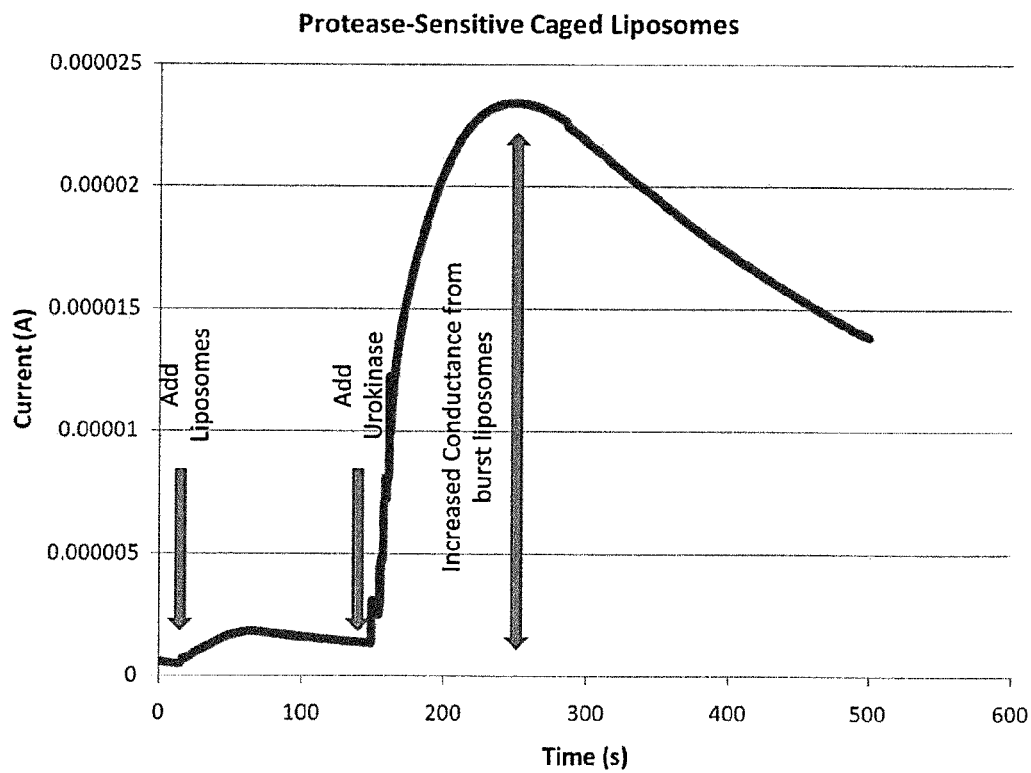
FIG. 35 is a graph of the detected change in conductance (current vs. time plot) when PCLs were degraded by urokinase in the buffer and burst to release their contents from Example 9.

Hypertonic polymer-caged liposomes were synthesized as described above using uPA consensus sequences and $MgSO_4$ (in varying concentrations ranging from 5× to 10×) as the solute to be encapsulated. The liposomes had a diameter of 120 nm, as determined by DLS. It was hypothesized that upon cleavage of the uPA consensus sequence, the liposomes would swell and burst, releasing their contents, which would increase the specific conductance of the aqueous system (such as blood and urine), in which the protease activity is to be measured. The results are shown in FIG. 35. The liposomes (5% percent by weight in $H_2O$) were added to 2 mL of bidistilled water at t=20 seconds, and the current (A) was measured as between two electrodes on an electrochemical workstation/analyzer (CH Instruments, Model 650B Series) at 25° C. The addition of the liposomes caused a small increase in the observed current. After this increase leveled off (at t=135 s), $10^{-11}$ mol of urokinase was then added in 50 µL of PBS. A significant increase in conductance was observed due to the release of $Mg^{2+}$ and $SO_4^{2-}$ from the liposomes' hydrophilic interior. The graph shows the current vs. time plot (E=−0.80V vs. Ag/AgCl). The results indicate that this supramolecular assay would be useful for detecting protease activity in any biological fluid and tissue samples (e.g., after surgery), with results available within less than 5 minutes. This is a substantial improvement in current state of the art. Detection could also be carried out in vivo using a set of microelectrodes after a solution of liposomes in water has been applied to the surface of the living tissue.

Example 10

Alternative Synthesis of Crosslinked Polymer Cage

Cholesterol, which serves as a membrane anchor in liposomes, was reacted with tert.-butyl-2-bromoacetate in DMF in the presence of trimethylamine or potassium carbonate. Quantitative reaction to the cholesterolester was observed. The protective group was then removed using 10% of conc. HCL in toluene (homologous carboxylic acids (n=2-6) would also work).

Scheme 1

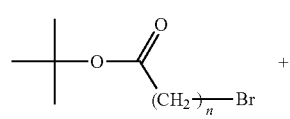

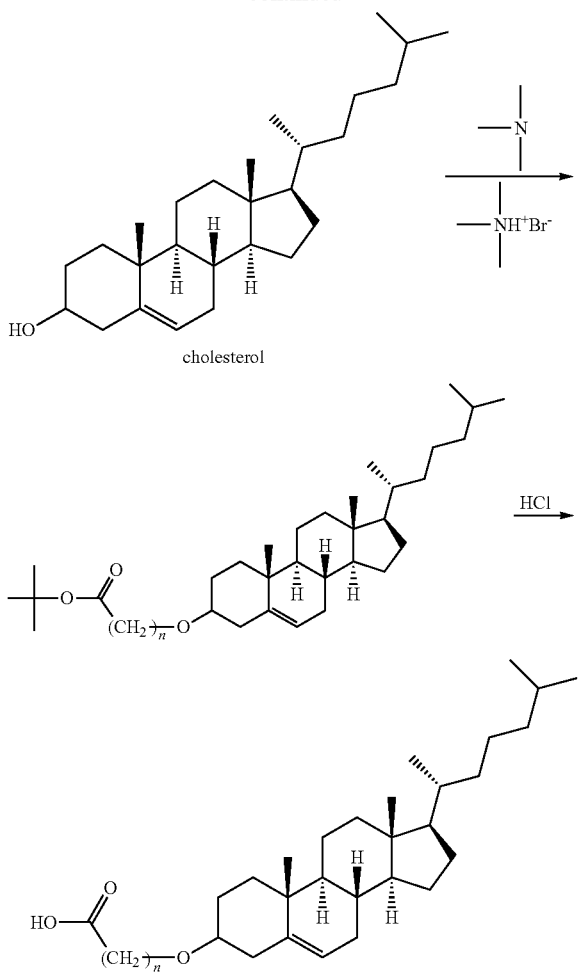

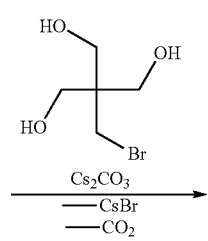

The reaction product from Scheme 1 was then reacted with 2-(bromomethyl)-2-(hydroxymethyl)propane-1,3-diol, using cesium carbonate in anhydrous DMF. Again, the reaction was quantitative (>95% after removal of DMF in vacuum and descending column chromatography on silica using $CH_2Cl_2$/MeOH 95/5 (v/v)).

Scheme 2

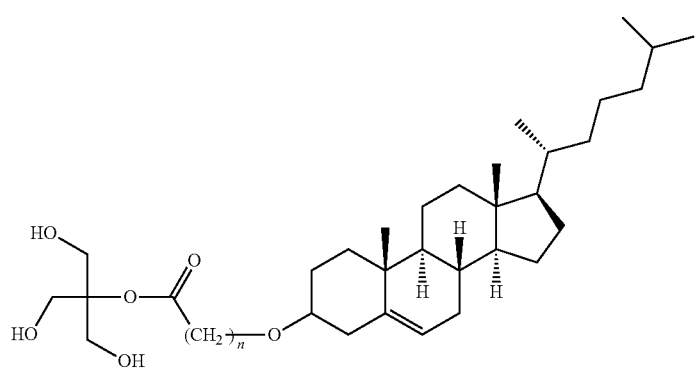

The reaction product from Scheme 2 was then linked to the chosen cleavage sequence (all protease-cleavage sequences possible) using EDC/HBTU (O-(benzotriazol-1-yl)-N,N,N', N'-tetramethyluroniumhexafluorophosphate) coupling in THF, with one cleavage sequence on each —OH group.

The polymers can be then incorporated into the bare liposome membrane (same procedure as previously described), followed by crosslinking the the cleavage sequences using CDI (carbonyl-bis-imidazole). That is, one cleavage sequence can be linked to each OH-group, and from there to the OH-group of the next polymer.

Example 11

Measuring uPA Activity In Vitro

PCLs were prepared as in Example 3 using cyanine 7.0 as the solute to be entrapped in the liposomes, and then used to measure urokinase-plaminogen activator activity in PBS. The concentration of Cy-7.0 in the liposomes was about 10 mg per g of lipid used to form the liposomes. At high concentrations self-quenching dyes, such as cyanines will form stable homo-complexes that change the absorbance profile of the dye and quench the fluorescence. Such dyes can be used to create liposomes that will only fluoresce once the entrapped dye is released.

20 mg/ml of the prepared Cy-7.0 PCLs were added to PBS, followed by $2.5 \times 10^{-10}$ urokinase-type plasminogen activator. The fluorescence spectrum was recorded every 5 min. (at 0, 5, 10, 15, 20, 25, 30, 35, 40, 45, and 50 minutes). The highest peak was visible after 50 minutes of incubation time. All measurements were taken at pH=6.8 in phosphate buffer using 4.0 mL quartz cuvettes (Helma) using a spectrofluo-rometer (Fluoromax 2) with dual monochromators and a diode array UV/Vis absorption spectrometer (HP 8453). Fluorescence excitation was performed at 775 nm.

Figure 36:
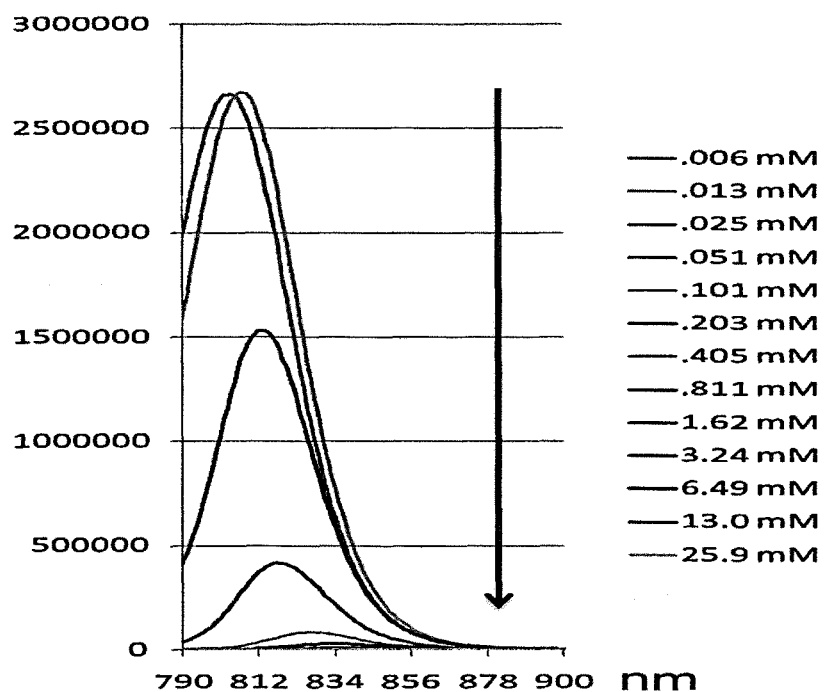
FIG. 36 is a graph of the fluorescence spectrum of cyanine 7.0 from Example 11.
Figure 37:
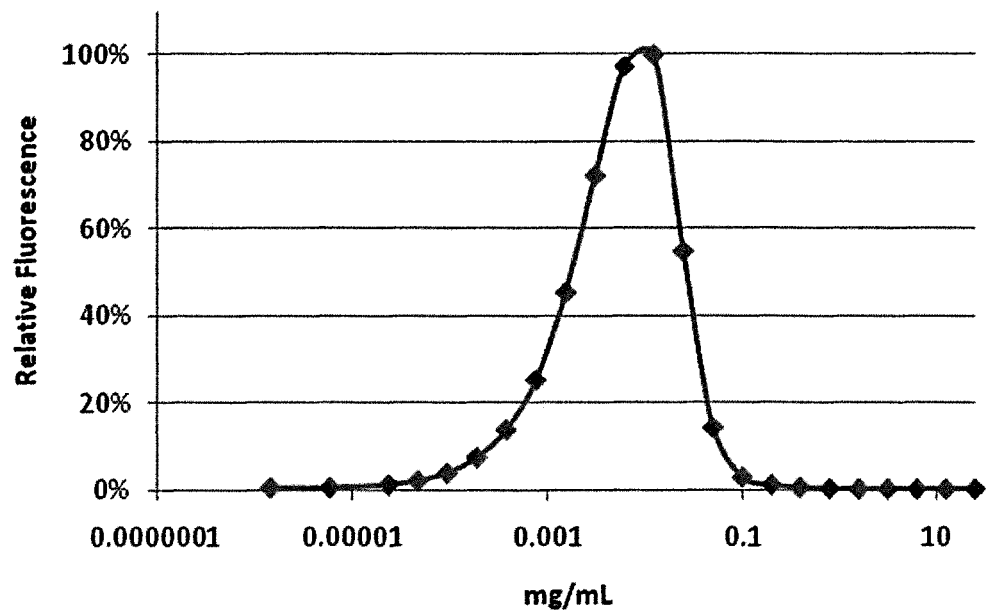
FIG. 37 is a graph of the relative fluorescence versus concentration of cyanine 7.0 from Example 11.

Due to the hypertonic nature of the liposomes, only a few cleavage sequences have to be cut by the enzyme to release the dye molecules and cause a significant increase in fluorescence, which is an improvement over previous protease-based assays. The results are shown in FIGS. 36-37.

Example 12

Protease-Sensitive TAT-Modified Cyanine 5.5 Release

TAT-linked cyanine 5.5 was synthesized from asymmetric cyanine 5.5 (bearing one 2-(hexanamido)-3-mercaptopro-panoic acid and one butane-1-sulfonic acid substituent), and cysteine-modified TAT peptide sequence (GRKKRRQR-RRPQC; SEQ ID NO: 73). TAT is a tumor-homing sequence used to ensure that the cyanine is not carried away from the cancerous tissue once released. The disulfide bond was formed by air oxidation in aerated aqueous solution, followed by dialysis and lyophilization (cutoff: 5,000).

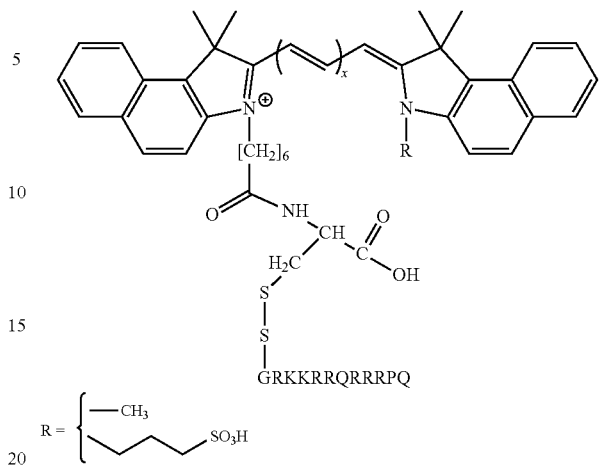

(SEQ ID NO: 73)

Cholesterol-tagged, protease-sensitive polyacrylic acids were synthesized as described in Example 2, except that a MMP-7 cleavage sequence VPLSLTMG (SEQ ID NO: 5) modified with a lysine (synthetic, >90% pure) was used instead of the uPA sequence. BLs, PILs, and PCLs were then prepared as described in Example 3 in 10× HBS, using VPLSLTMGK (SEQ ID NO: 5) as the crosslinker (added as 1 mol per 10 mols of carboxylic acid groups) and the TAT-linked cyanine 5.5 as the solute to be entrapped in the liposomes.

1. In Vitro Detection

Various dilutions of HBS were then made by diluting 10× HBS with 0.012 M HEPES Buffer to make the solutions have the desired pressures against 10× HBS (internal environment of liposomes). The desired samples were then diluted so that the sample contained 2 μmol TAT-modified cyanine 5.5 in 2 mL for each sample. The diluted samples were incubated at 37.5° C. for the desired time and then fluorescence measurements were taken to determine percent release. TAT-modified cyanine 5.5 was excited at 675 nm and the fluorescence was recorded from 685 nm to 720 nm. Total fluorescence was determined by summing the fluorescence from 685 nm to 720 nm. Curves of total fluorescence verses pressure were fitted using a logistic function:

$$F(\Pi) = \frac{A}{B + Ce^{-D\Pi + E}}$$

where Π is the difference in osmotic pressure and A, B, C, D, and E are fitting constants. The fluorescence verses pressure curves were then compared to determine the difference in pressure sensitivity of various liposome preparations.

Figure 38:
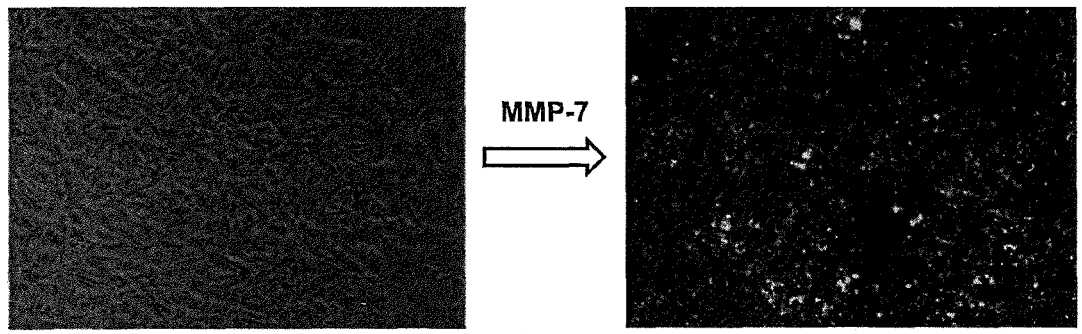
FIG. 38 shows fluorescence microscopy images of stem cells directly after adding the liposomes in PBS (left image) and after 1 hour of incubation (right image)

The PCLs containing the equivalent of 5 mM Cy-5.5 were then incubated with murine neural stem cells for 24 hours. As shown in the fluorescence microscopy images in FIG. 38, the stem cells were able to take up the PCLs. The left side shows the NSCs directly after adding the liposomes in PBS. The right image shows the NSCs after 1 hour of incubation. The bright gray shows the fluorescence from cyanine 5.5. The results indicate that the supramolecular assemblies can be used to positively identify circulating tumor stem cells (CTC's), which are known to express MMP-7.

2. In Vivo Detection

Figure 39:
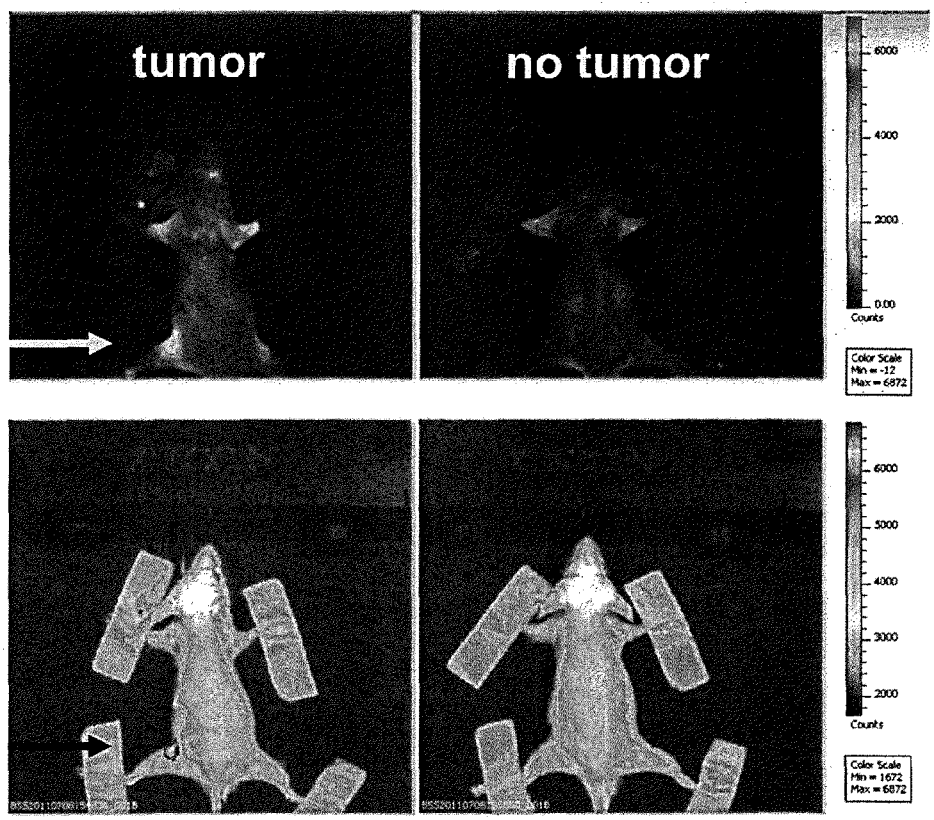
FIG. 39 shows IVIS images of transgenic mice imaged using the supramolecular assemblies, one bearing a tumor, one without an apparent tumor from Example 12.

For in vivo imaging and detection, 100 mg of the PCLs containing TAT-modified Cy-5.5 were dissolved in 1 mL of PBS, and injected in the large tail vein of two FVB-Tg(C3-1-Tag)cJeg/J transgenic mice (one bearing a tumor, one without an apparent tumor, both mice were 4 weeks old) under short anesthesia (isofluorane). The mice were kept under isofluorane while they were imaged using the IVIS equipment available in the Troyer group (10 min. in total). The images are shown in FIG. 39.

Example 13

Synthesis of Oligopeptide-Based Polymer Cage

1. Procedure

Figure 40:
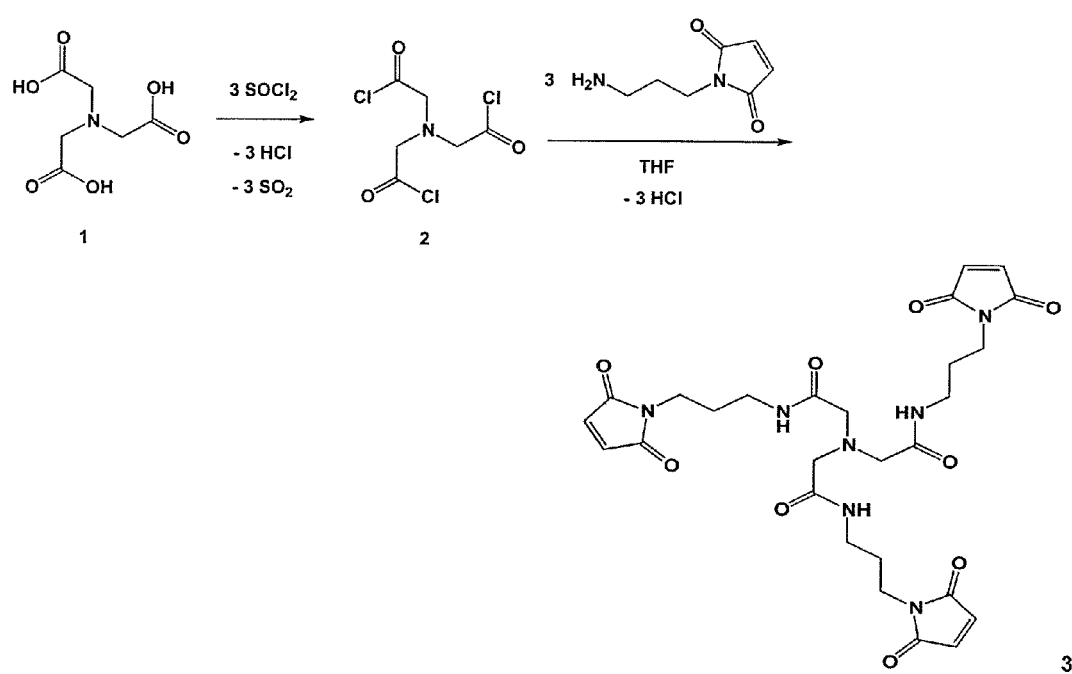
FIG. 40 illustrates the reaction mechanism for forming the tri-functional core compound in Example 13.

A tri-functional core including a spacer moiety (2,2',2"-nitrilotris(N-(3-(2,5-dioxo-2,5-dihydro-1H-pyrrol-1-yl)propyl)acetamide)) was first synthesized by treating 63 mg (0.00033 mol) of 2,2',2"-nitrilotriacetic acid (NTA) with 5 mL of thionyl chloride ($SOCl_2$) at −20° C. The mixture was allowed to warm to room temperature overnight. The remaining $SOCl_2$ was removed in high vacuum, yielding a light brown solid. Next, 0.153 mg (0.0010 mol) of 1-(3-aminopropyl)-1H-pyrrole-2,5-dione was dissolved in 20 mL of anhydrous THF and added to the solid at −20° C. The reaction mixture was purged with argon, followed by adding 0.50 g of NaH (sodium hydride) as solid. The reaction mixture was again allowed to warm to room temperature and maintained at room temperature for 5 h, followed by refluxing for 1 h. After removing the solvent in high vacuum, a brown solid was obtained. The reaction mechanism is shown in FIG. 40. Recrystallization from diethyl ether yielded 102.9 mg (0.00017 mol, 52 percent) of the tri-functional maleimide/NTC core (3).

Peptide linkages containing the consensus sequences and cholesterol anchors were then added to the core via Michael addition of the thiol-group of a cysteine residue to each of the 3 maleimide units attached to NTA in the core. The reaction was carried out in water/MeOH 1:1 under argon. The stoichiometry was exactly 3 oligopeptides to 1 core molecule. The typical concentration was $1\times10^{-4}$M core and $3\times10^{-4}$M (oligopeptides). This reaction was performed using positively charged or negatively charged amino acid sequences between respective consensus sequences and cholesterol anchors. The consensus sequence used for these experiments was DEVDG (SEQ ID NO: 74), which further included a terminal cysteine residue for reaction with the maleimide. The positively charged amino acid sequences included 20 lysine residues. The negatively charged sequences included 20 aspartic acid residues. The oligopeptides are shown in the Table below. Glutamic acid residues could be used in place of the aspartic acid residues.

TABLE

| | Oligopeptides |
|---|---|
| Type | Oligopeptide |
| + | C-DEVDG-$(K)_x$-cholesterol (SEQ ID NO:76), where x is 20 |
| − | C-DEVDG-$(D)_x$-cholesterol (SEQ ID NO:77), where x is 20 |
| − | C-DEVDG-$(E)_x$-cholesterol (SEQ ID NO:78), where x is 20 |

Figure 41:
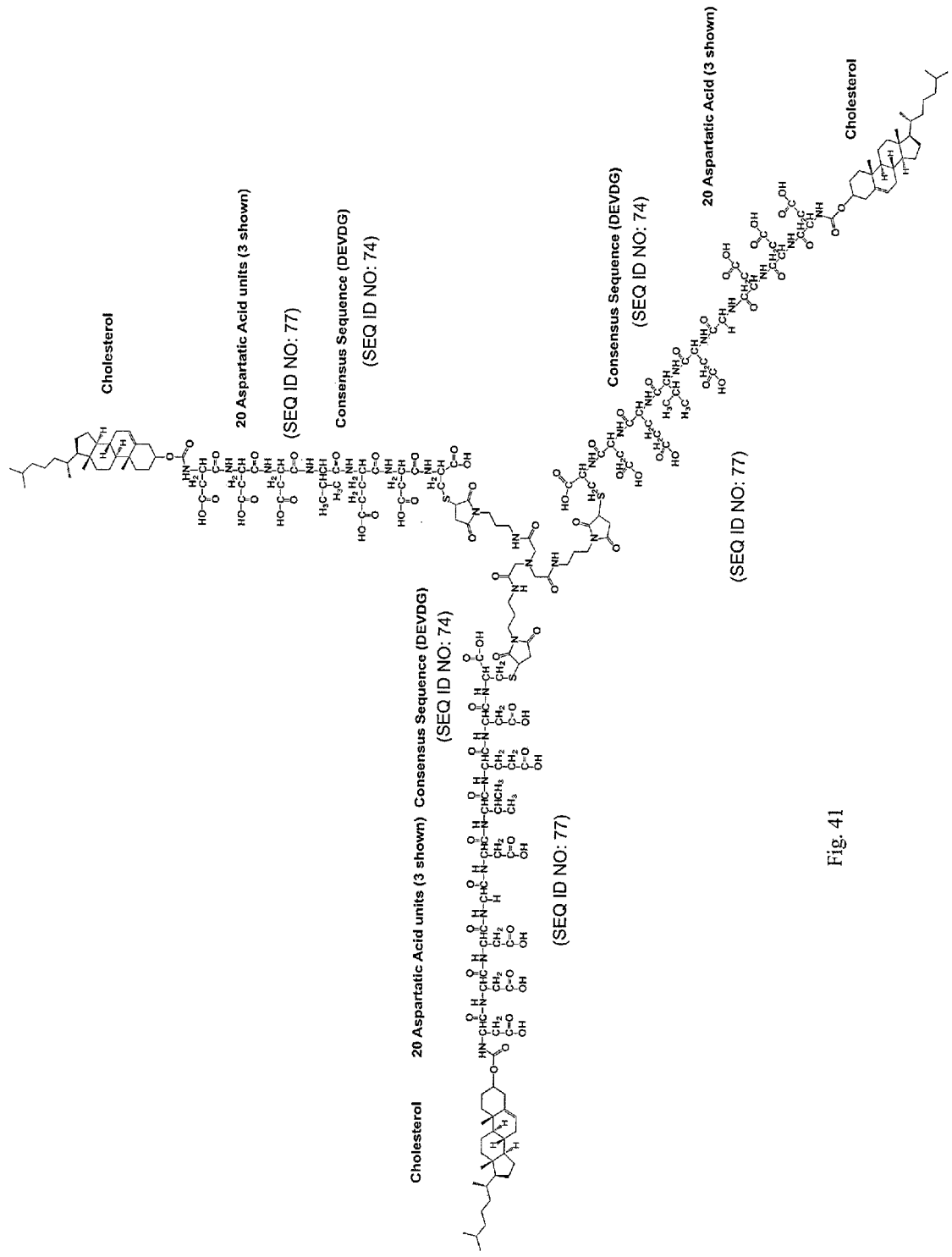
FIG. 41 depicts a negatively-charged branched oligopeptide synthesized in Example 13.
Figure 42:
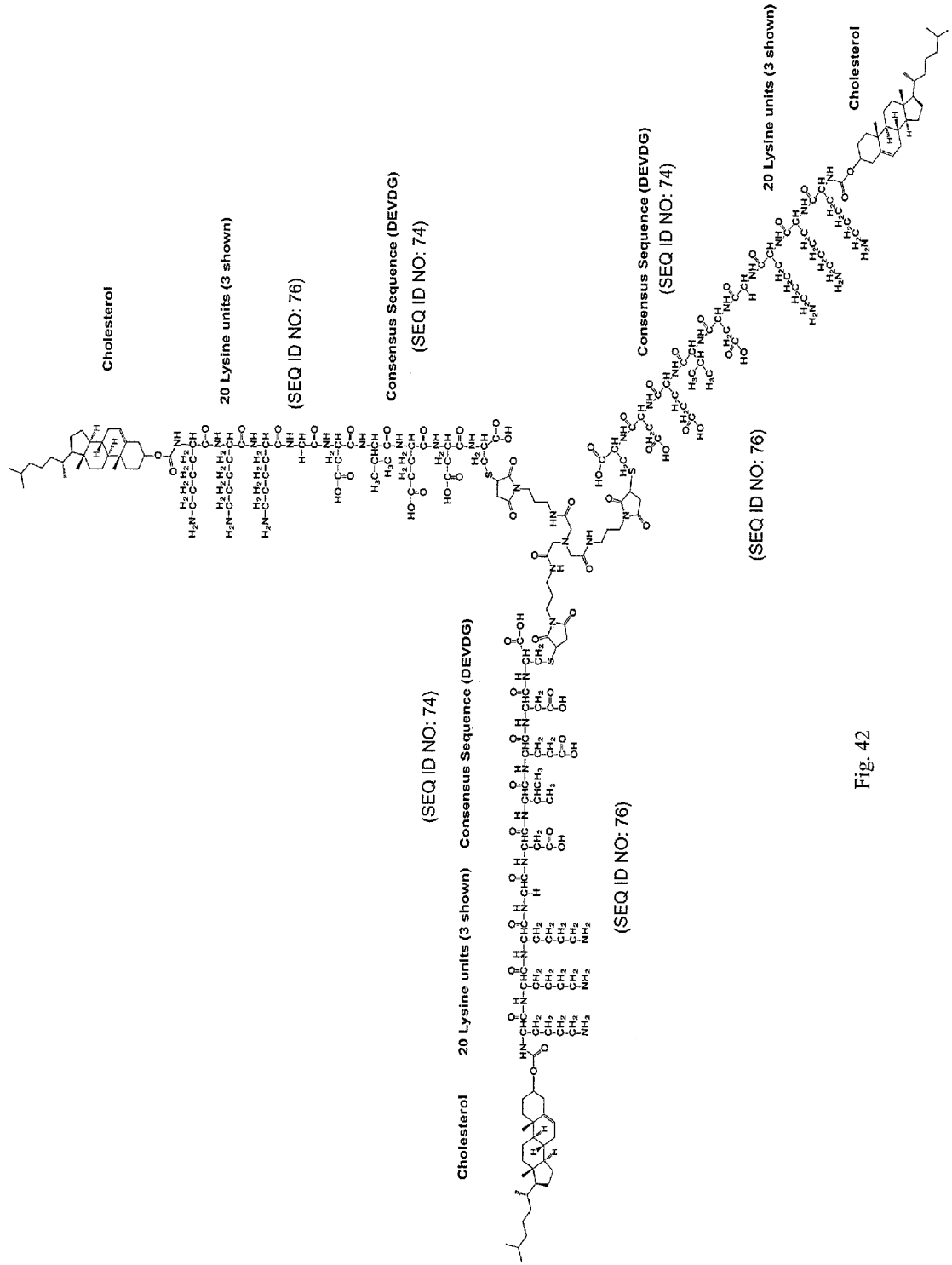
FIG. 42 depicts a positively-charged branched oligopeptide synthesized in Example 13.

The reactions were monitored by qualitative HPLC (MeOH/$H_2O$ gradients, RP18 column, UV/Vis detection). After 5 days at room temperature, the addition was 98% complete. Following lyophilization, the positively charged and negatively charged trifunctional oligopeptide cage building blocks were used without purification. The resulting oligopeptide building blocks are shown in FIGS. 41 and 42.

Figure 43:
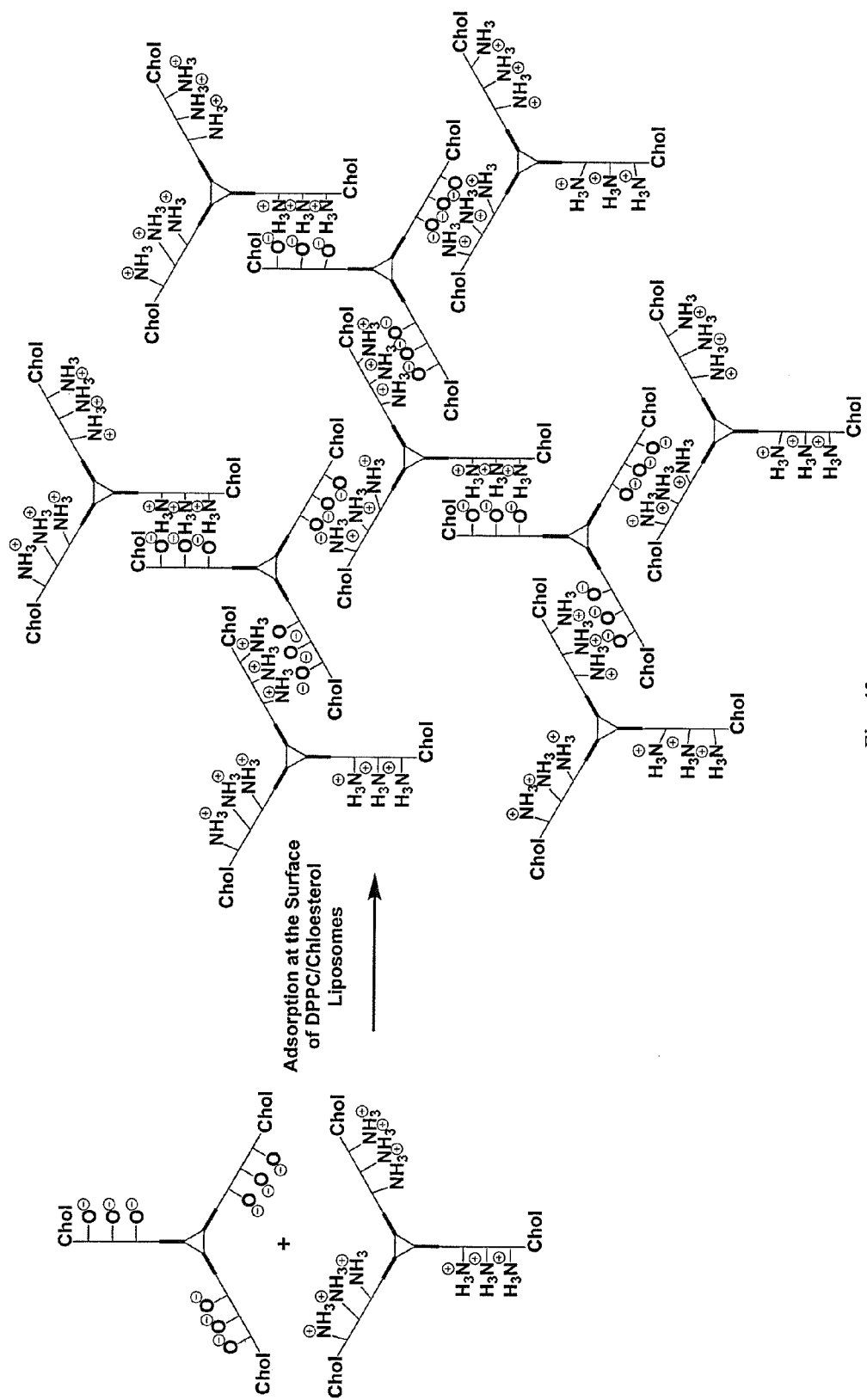
FIG. 43 is a schematic showing the association of the positively- and negatively-charged oligopeptides in Example 13.
Figure 44:
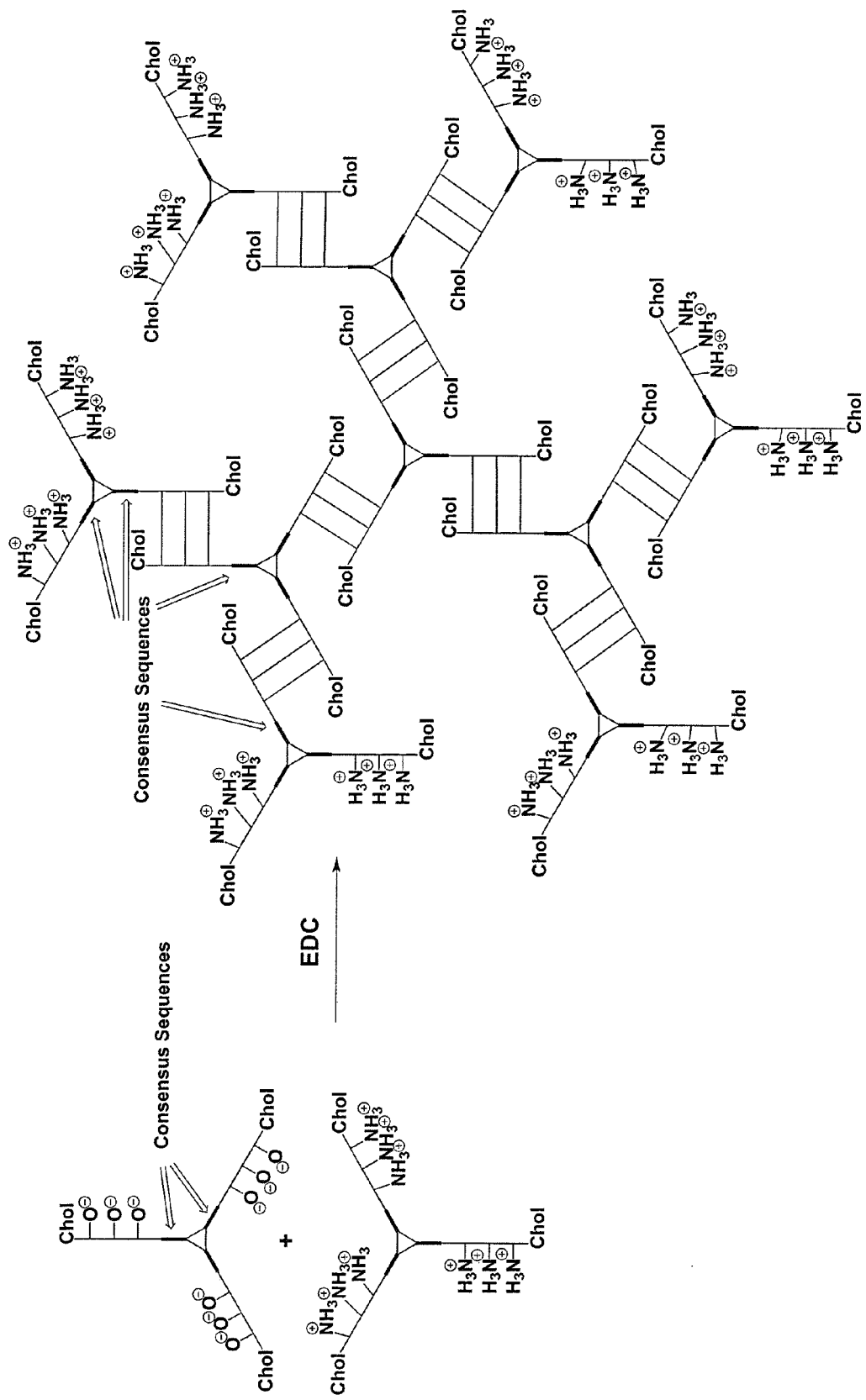
FIG. 44 is a schematic depicting the crosslinking of the branched oligopeptides in Example 13.

The oligopeptide building blocks were used to prepare protease-cleavable caged liposomes. Hypertonic (2x) DPPC/Cholesterol Liposomes were first synthesized as described above. Next, one molecule of negatively-charged Building Block 1 (BB1; FIG. 41) and one molecule of positively-charged Building Block 2 (BB2; FIG. 42) per 50 DPPC molecules of the liposomes were added to a dispersion of unilamellar DPPC/cholesterol liposomes (d=120 nm) in 1× HEPES (4-(2-hydroxyethyl)-1-piperazineethanesulfonic acid) buffer, pH=7.5. The mixture was incubated at 37° C. for 1 h. The reaction is shown in FIG. 43. Then one mole of EDC hydrochloride and 0.10 mol of hydroxytriazole per each lysine unit added (here: 60 per mole of BB2) is added as a solid in small portions during 1 h. The resulting mixture was allowed to react for 24 h at 37° C., and the reaction is shown in FIG. 44. The resulting PCCL's were then purified using a Sephadexcolumn using 1× HEPES buffer as eluent. Characterization of the PCCL's was done using Dynamic Light Scattering, and showed a monodisperse size distribution (d=133 nm, polydispersity=1.05).

2. Discussion

Figure 45:
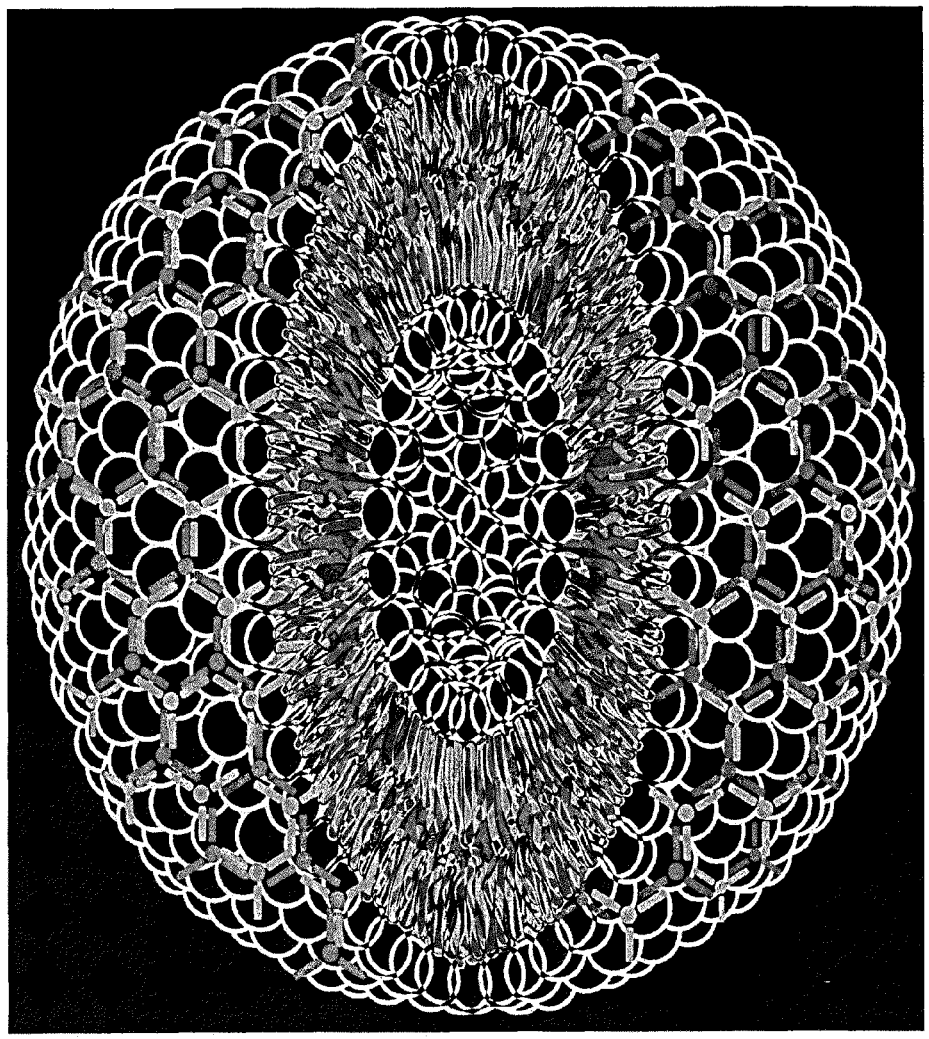
FIG. 45 is an dissected image of a caged liposome created in Example 13 showing the hexagonal geometry of the crosslinked branched oligopeptides encasing the liposome membrane.

It is known that about 5-8 kJ per mol of energy and salt bridges can be gained through the formation of salt bridges by monocations and monoanions. Assuming the lower value of 5 kJ per mol and the presence of 9-90 aminoacids with either positive or negative charges in one building block, the resulting attractive energy when forming a supramolecular network at the surface of he liposome is between 45 kJ and 450 kJ. This is large enough to force the formation of geometric hexagons at the liposome's surface. The membrane anchors that are located at the "finger-tips" of the peptide sequences ensure that the building blocks stay adsorbed at the outer phospholipid/water interface. The resulting structure is shown in FIG. 45.

As described above, the two building blocks (BB1 and BB2) assume negative and positive charges when in buffered aqueous solution (PBS or HEPES buffer, the pH range should be between 6 and 8). The different charges cause the formation of a hexagons. After the orientation of the building blocks has been completed (~1 h), the lysine and aspartate or glutamate units can be crosslinked using a suitable water-soluble crosslinking agent (e.g., EDC) in the presence of an active ester (e.g., N-hydroxysuccinimide or hydroxyl-benzotriazol), which results in a crosslinked hexagonal network or cage around the liposomes.

We claim:

1. A protease-sensitive supramolecular assembly comprising:
  a liposome comprising a membrane defining an interior space;
  a crosslinked, polymeric coating adjacent said membrane, said coating comprising a protease consensus sequence and a targeting moiety attached to said crosslinked, polymeric coating; and
  an active agent encapsulated in said liposome, wherein said active agent is dissolved or dispersed in a pharmaceutically-acceptable carrier or excipient.

2. A diagnostic and/or therapeutic composition comprising a plurality of protease-sensitive supramolecular assemblies according to claim 1, optionally dispersed in a pharmaceutically-acceptable carrier or excipient.

3. The composition of claim 2, wherein said composition is in a form suitable for oral administration to a subject.

4. A protease-sensitive supramolecular assembly comprising:
  a liposome comprising a membrane defining an interior space;
  a crosslinked, polymeric coating adjacent said membrane, said coating comprising a protease consensus sequence; and
  an active agent encapsulated in said liposome, wherein said active agent is dissolved or dispersed in a pharmaceutically-acceptable carrier or excipient, and wherein said crosslinked, polymeric coating comprises a polymer crosslinked with a crosslinking agent, said protease consensus sequence being present in said coating as part of said polymer, as part of said crosslinking agent, or a combination thereof, said polymer comprising a membrane anchor, a crosslinkable unit, and optionally a peptide linkage comprising said protease consensus sequence.

5. The supramolecular assembly of claim 4, wherein said anchor is embedded in said liposome membrane, said polymer being crosslinked with said crosslinking agent via said crosslinkable unit.

6. The supramolecular assembly of claim 4, wherein said anchor is selected from the group consisting of steroids, $C_{16}$ and higher fatty acids containing a least one double-bond, cell-penetrating peptides, and combinations thereof.

7. The supramolecular assembly of claim 4, wherein said polymer is an oligopeptide, said crosslinkable unit being between said membrane anchor and said peptide linkage in the polymer chain, wherein said crosslinkable unit comprises repeating amino acid residues having a positive or negative charge in buffered aqueous solution.

8. The supramolecular assembly of claim 4, wherein said polymer is a branched polymer comprising a core and polymer chains radiating therefrom, wherein each of said polymer chains comprises respective membrane anchors, crosslinkable units, and optional peptide linkages comprising said protease consensus sequence.

9. A diagnostic and/or therapeutic composition comprising a plurality of protease-sensitive supramolecular assemblies, wherein said protease-sensitive supramolecular assemblies comprise:
  a liposome comprising a membrane defining an interior space;
  a crosslinked, polymeric coating adjacent said membrane, said coating comprising a protease consensus sequence; and
  an active agent encapsulated in said liposome, wherein said active agent is dissolved or dispersed in a pharmaceutically-acceptable carrier or excipient,
  and wherein said composition is optionally dispersed in a pharmaceutically-acceptable carrier or excipient, and further wherein said composition is a dried composition.

10. The composition of claim 9, wherein said active agent is selected from the group consisting of therapeutic agents, dyes, salts, and combinations thereof.

11. The composition of claim 10, wherein said therapeutic agents are selected from the group consisting of therapeutic molecules, biologics, radioactive isotopes, poisons, toxins, and combinations thereof.

12. The composition of claim 10, wherein said dyes are selected from the group consisting of organic dyes, inorganic dyes, fluorophores, phosphophores, and combinations thereof.

13. The composition of claim 9, wherein said interior space is hypertonic.

14. The composition of claim 13, the tonicity of said interior space of the liposomes is from about 1x to about 20x more than normal physiological solute concentration.

15. The composition of claim 9, wherein said consensus sequence is selected from the group consisting of serine protease cleavage sequences, aspartyl protease cleavage sequences, cysteine protease cleavage sequences, metalloprotease cleaveage sequences, caspase protease sequence, and combinations thereof.

16. The composition of claim 9, wherein said consensus sequence is for a protease selected from the group consisting of urokinase, matrix metallopeptidase, cathepsin, caspase, and combinations thereof.

17. The composition of claim 9, wherein said crosslinked, polymeric coating comprises a polymer crosslinked with a crosslinking agent, said protease consensus sequence being present in said coating as part of said polymer, as part of said crosslinking agent, or a combination thereof, wherein said crosslinking agent is selected from the group consisting of amines, hydroxys, thiols, carboxylic acids, and combinations thereof.

18. A method of detecting the activity of a protease associated with a cancerous or precancerous cell or cancer stem cell in a subject, said method comprising:
contacting a sample comprising biological fluid from the subject with a diagnostic assay, said assay comprising a composition according to claim 9; and
detecting a change in said sample, wherein:
said active agent is a salt, and said change is an increase in the electrical current detected in said sample, wherein said increased current correlates to said protease activity which releases said salt from one or more of said supramolecular assemblies, or
said active agent is a dye, and said change is the appearance of an emission spectrum in said sample, wherein said emission spectrum correlates to said protease activity which releases said dye from one or more of said supramolecular assemblies.

19. A method of detecting the activity of a protease associated with a cancerous or precancerous cell or cancer stem cell in a subject, said method comprising:
administering to the subject a composition according to claim 9, wherein said active agent is a dye; and
detecting the emission spectrum of the dye, wherein said emission spectrum correlates to said protease activity which releases said dye from one or more of said supramolecular assemblies.

20. The method of claim 19, further comprising exciting said dye by exposing one or more of said supramolecular assemblies to an energy source prior to said detecting.

21. A method of treating a disease or condition associated with protease activity in a subject, said method comprising:
administering to the subject a therapeutically effective amount of a composition according to claim 9, wherein said active agent is a therapeutic agent, and wherein one or more of said supramolecular assemblies accumulate in and near said protease activity in said subject to deliver said therapeutic agent thereto.

22. The method of claim 21, wherein said therapeutic agent is selected from the group consisting of small molecule drugs, macromolecules, recombinant nucleic acids, RNA oligomers, DNA plasmids, enzymes, proteins, radium 223, thorium 227, actinium 225, astatine 211, bismuth 212, phosphorous 32, yttrium 90, iodine 131, samarium 153, strontium 89, technetium 99 and indum 111, iodine 125), poisons, saporin, ricin, prodrugs, and combinations thereof.

23. The method of claim 21, wherein said disease or condition is cancerous or precancerous tissue or cancer stem cells, said supramolecular assemblies accumulating in and near said tissue or cells to deliver said therapeutic agent thereto.

24. The method of claim 21, wherein said protease activity cleaves said consensus sequence thereby releasing said therapeutic agent from one or more of said assemblies.

\* \* \* \* \*